(12) United States Patent
Assaly et al.

(10) Patent No.: US 7,884,068 B2
(45) Date of Patent: *Feb. 8, 2011

(54) ALBUMIN-BASED COLLOID COMPOSITION HAVING AT LEAST ONE PROTECTED THIOL REGION, METHODS OF MAKING, AND METHODS OF USE

(76) Inventors: Ragheb A. Assaly, 6710 Victoria Ct., Sylvania, OH (US) 43560; J. David Dignam, 28741 Georgia Rd., Perrysburg, OH (US) 43551; Joseph I. Shapiro, 7027 Altonbrough, Toledo, OH (US) 43617

( * ) Notice: Subject to any disclaimer, the term of this patent is extended or adjusted under 35 U.S.C. 154(b) by 769 days.

This patent is subject to a terminal disclaimer.

(21) Appl. No.: 10/985,798

(22) Filed: Nov. 9, 2004

(65) Prior Publication Data

US 2005/0187139 A1    Aug. 25, 2005

(51) Int. Cl.
*A61K 38/38* (2006.01)

(52) U.S. Cl. .............................. 514/2; 514/12; 530/363
(58) Field of Classification Search ................. 424/422, 424/93.73; 514/12
See application file for complete search history.

(56) References Cited

U.S. PATENT DOCUMENTS

| | | | |
|---|---|---|---|
| 2,727,027 | A | 12/1955 | Monson et al. |
| 4,101,380 | A | 7/1978 | Rubinstein et al. |
| 4,179,337 | A | 12/1979 | Davis et al. |
| 5,324,844 | A | 6/1994 | Zalipsky |
| 5,583,114 | A | 12/1996 | Barrows et al. |
| 5,650,234 | A | 7/1997 | Dolence et al. |
| 5,704,358 | A | 1/1998 | Zikria |
| 5,714,511 | A | 2/1998 | Saavedra et al. |
| 5,733,563 | A | 3/1998 | Fortier |
| 5,756,481 | A | 5/1998 | Arnal et al. |
| 5,952,009 | A | 9/1999 | Neurath et al. |
| 6,063,764 | A | 5/2000 | Creasey et al. |
| 6,129,912 | A | 10/2000 | Hortin et al. |
| 6,344,197 | B2 | 2/2002 | Fisher et al. |

OTHER PUBLICATIONS

Cha, M-K., et al. 1996 Biochem. Biophys. Res. Comm. 222: 619-625.*
Matejtschuk, P., et al. 2000 British Journal of Anaesthesia 85(6): 887-895.*
Shewale, J.G., et al. 1984 J Biol Chem 259(8): 4947-4956.*
Palmiter, R.D., et al. 1978 PNAS 75(1): 94-98.*
Lee, H., et al. 2000 Archives Biochem Biophys 380(2): 309-318.*
Masaki, K., et al. 2000 Protein Engineering 13(1): 1-4.*
Matejtschuk, P., et al. 2000 British Journal of Anaesthesia 85(6): 887-95.*
Conley et al. Britannica Encyclopedia Blood article (21 pages), 2007.*

Wu Lin, Martin C. Garnett, Etienne Schacht, Stanley S. Davis, Lisbeth Illum, *Preparation and in vitro characterization of HAS-mPEG nanoparticles*, International Journal of Pharmaceutics, 189 (1999), pp. 161-170.
Angus, D.C., Wax, R.S., *Epidemiology of Sepsis—An Update*, Critical Care Medicine.29 (7) (2001) S109-S116.
Baue, A.E., Durham, R., Faist, E., *Systemic Inflammatory Response Syndrome (SIRS) Multiple Organ Dysfunction Syndrome (MODS), Multiple Organ Failure (MOF) Are We Winning The Battle?*, Shock. 10 (2)(1998) 79-89.
Roberts, J.S., Bratton, S.L. *Colloid volume expanders: problems, pitfalls and possibilities*, Drugs. 55(5)(1998) 621-630.
Berger, A., *Why albumin may not work* (editor's commentary). BMJ, (1998) 317:240.
Doweiko, J.P. And Nompleggi, D.J., *Interactions of Albumin and Medications*, J. Parenter. Enteral. Nutr. 15, (1991) 212-214.
Emerson, T.E., *Unique features of albumin: a brief review*, Crit Care Med. 17(7) (1989) 690-694.
Margarson, M.P., Soni, N., *Serum Albumin: touchstone or totem?* Anaesthesia, 53 (1998) 789-803.
McClelland, *Human albumin administration in critically ill patients*, BMJ, 317 (1998) 882-886.
Wilkes,M. And Navickis, R.J., *Patient survival after human albumin administration*, Ann Intern Med. 135 (2001) 149-164.
Cochrane Injuries Group Albumin Reviewers, *Human albumin administration in critically ill patients: systematic review of randomized controlled trials*, BMJ 317(1998) 235-40.
Delgado, C., Francis, G.E., and Fisher D., The uses and properties of PEG-linked proteins. Critical Reviews in Therapeutic Drug Carrier Systems. 9(3,4) (1992) 249-304.
Abuchowski, A., Van Es, T., Palozuk, N.C., and Davis. F., *Alteration of immunological properties of bovine serum albumin by covalent attachment of polyethylene glycol*, J. Biol Chem. 252(1)(1997) 3578-3581.
Kozlowski A; Charles SA; Harris JM, *Development of pegylated interferons for the treatment of chronic hepatits C*, BioDrugs 15 (2001) 419-29.
Conover, C, Malatesta, P., Lejuene, Chang, C.L., and Shorr, R.G.L., *The effects of hemodilution with polyethylene glycol bovine hemoglobin (Peg-Hb) in a conscious porcine model*, J Inves Med. 44(5)(1996) 238-246.
Conover, C.D., Lejuene, L., Shum, K., Gilbert, C., and Shorr, R.G., *Physiological effect of polyethylene glycol conjugation of stroma-free bovine hemoglobin in the conscious dog after partial exchange transfusion*, Artif Organs. 21(5)(1997)369-78.

(Continued)

*Primary Examiner*—Manjunath N Rao
*Assistant Examiner*—Marsha M Tsay
(74) *Attorney, Agent, or Firm*—Emch, Schaffer, Schaub & Porcello Co., LPA

(57) ABSTRACT

A composition comprising an albumin-based colloid composition having at least one protected thiol region, method of making the same, and method for use, including treating hypovolemic conditions such as capillary leak syndrome and shock, are disclosed.

12 Claims, 24 Drawing Sheets
(18 of 24 Drawing Sheet(s) Filed in Color)

OTHER PUBLICATIONS

Conover, C.D., Linberg, R., Lejuene, L., Nagy, M., and Shum, K.L., *PEG-hemoglobin as a resuscitation solution in the treatment of hypovolemic shock in the anesthetized rat*, Artif. Organs 23(12)(1999) 1088-1098.

Yeh, T., Parmar, J.M., Rebeyka, I.M., Lofland, G.K., Allen, E.L., Dignan, R.J., et al. *Limiting edema in neonatal cardiopulmonary bypass with narrow-range molecular weight hydroxyethyl starch*, J. Thorac Cardiovasc Surg. 104 (1992) 659-65.

Axon, R.N., Baird, M.S., Lang, J.D., Brix, A.E., Nielson, V.G., *Pentalyte Decreases Lung Injury After Aortic Occlusion-Reperfusion*, Am J. Reespir. CritCare Med. 157 (1998).

Heneka, M.T., Loschmann, P.A. Osswald, H., *Polymerized Hemoglobin Restores Cardiovascular and Kidney Function in Endotoxin-induced Shock in the Rat*, J.Clin.Invest. 99(1997) 47-54.

Zoellner, H., Hofler, M., Beckmann, R., Hufnagel, Vanyek, E., Blelek E., et al., *Serum albumin is a specific inhibitor of apoptosis in human endothelial cells*, J. Cell Science, 109 (1996) 2571-2580.

Cantin, A.M., Paquette, B., Richter, M., and Larivee, P., *Albumin-mediated regulation of cellular glutathione and nuclear factor Kappa B activation*, Am J Respir Crit Care Med, 162(2000) 1539-1546.

Assaly, R., Olson, D., Hammersely, J., Fan, P.S., Liu J., Shapiro J., Kahaleh, B., *Initial Evidence of Endothelial Cell Apoptosis as a Mechanism of Systemic Capillary Leak Syndrome*, Chest:120(2001) 1301-1308.

Quinlan, G.J., Margarson, M.P., Mumby, S., Evans, T.W., Gutteridge, J.M.C., *Administration of albumin to patients with sepsis syndrome: a possible beneficial role in plasma thiol repletion*, Clin. Sci. 95 (1998) 459-465.

Filep, J.G., Delalandre, A., Beauchamp, M., *Dual role for nitric oxide in the regulation of plasma volume and albumin escape during endotoxin shock in conscious rats*, Circ Res., 81 (1997) 840-847.

Tanford, C., Physical Chemistry of Macromolecules, John Wiley & Sons, (1961) p. 217.

Vandegriff, K.D., McCarthy, M., Rohlfs, R.J., and Winslow, R.M., *Colloid osmotic properties of modified hemoglobin: chemically cross-linked versus polyethyethylene glycol surface-conjugated*, Biophys. Chem. 69 (1997) 23-30.

Laemmli, U.K., *Cleavage of structural proteins during the assembly of the head of bacteriophage*, T4, Nature, 227 (1970) 6980-6985.

Johnson, D.E., *Applied multivariate Methods for Data Anaylsis*, Duxbury Press, (1998) page 319-121.

Bullock, J., *Characterization of Polyethelene glyol-Modified Superoxide Dismutase: Comparison of Capillary Electrophoresis and Marix-Assisted Laser Desorption/Ionization Mass Spectometry*, Anal.Chem. 68 (1996) 3258-3264.

Veronese, F.M., *Peptide and protein PEGylation: a review of problems and solutions*, Biomaterials 22 (2001) 405-417.

Nathan, C., Inducible Nitric Oxide Synthase: *What Difference Does It Make?* J.Clin.Invest., 100(10)(1997) 2417-2423.

Hubbard, J.D., Janssen, H.F., Increased microvascular permeability in canine endotoxic shock: protective effects of ibuprofen, Circ Shock 26 (1988) 169-183.

Taylor, AE, Granger DN, *Exchange of macromolecules across the microcirculation. Handbook of Physiology*, The Cardiovascular System IV, Am Physiol Soc, 4(1)11 (1984) 467-520.

Abuchowski, A., Van ES, T., Palozuk, N.C., and Davis, F., *Alteration of immunological properties of bovine serum albumin by covalent attachment of polyethylene glycol*, J Biol Chem. 252(11)(1977) 3578-3581.

Hershey, S.G. And Altura, Burton M.; Effect of Pretreatment With Aggregate Albumin on Reticuloendothelial System Activity and Survival After Experimental Shock; Proceedings of the Society for Experimental Biology and Medicine; Aug.-Sept. 1996—vol. 122, No. 4.

* cited by examiner

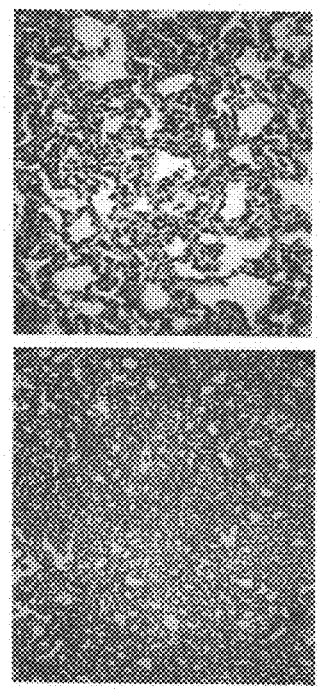
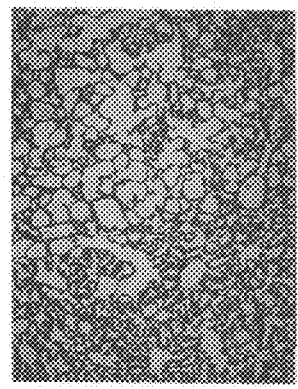
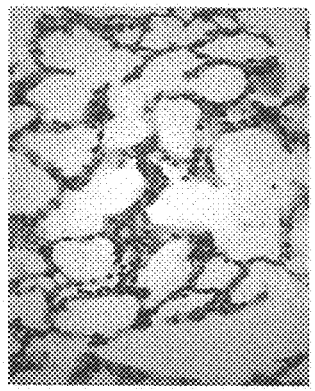
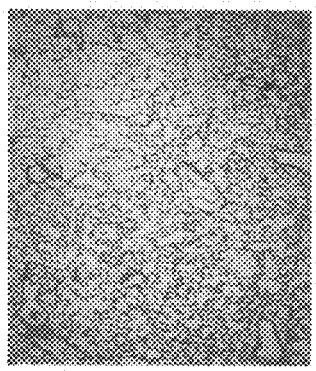
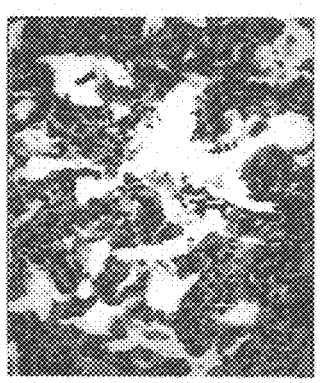
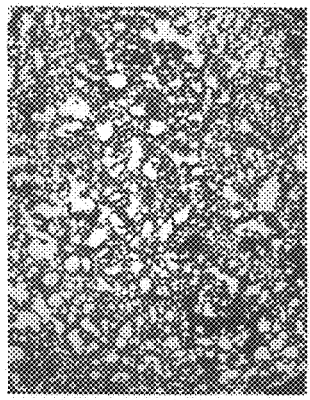
FIG. 3A  FIG. 3B  FIG. 3C  FIG. 3D

| Groups (N) | Htc Baseline | Htc Before Rx | Htc End Rx | COP Baseline | COP Before Rx | COP End Rx |
|---|---|---|---|---|---|---|
| Saline (6) | 47±18 | 38.4±21 a ** | 30.1±14 a ** | 19±0.9 | 13.8±1.2 a ** | 8.4±1.2 a ** |
| Albumin. (6) | 48±12 | 37.2±2 a** | 25.6±1 a** | 18.8±0.7 | 13.5±0.99 NS | 13.3± 2.9 NS |
| PEG-Alb (6) | 48±15 | 38.2±18 a ** | 23.1±12 a** | 19.2±0.4 | 13.92±0.93 a ** | 16.7±3.6a ** |
| P Value | NS all | NS all | b *, c ** | NS all | NS all | b **, c **, d * |
FIG. 18A
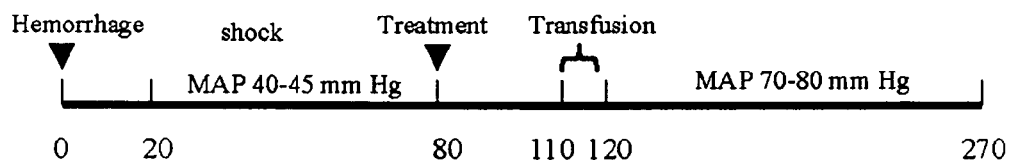
FIG. 19
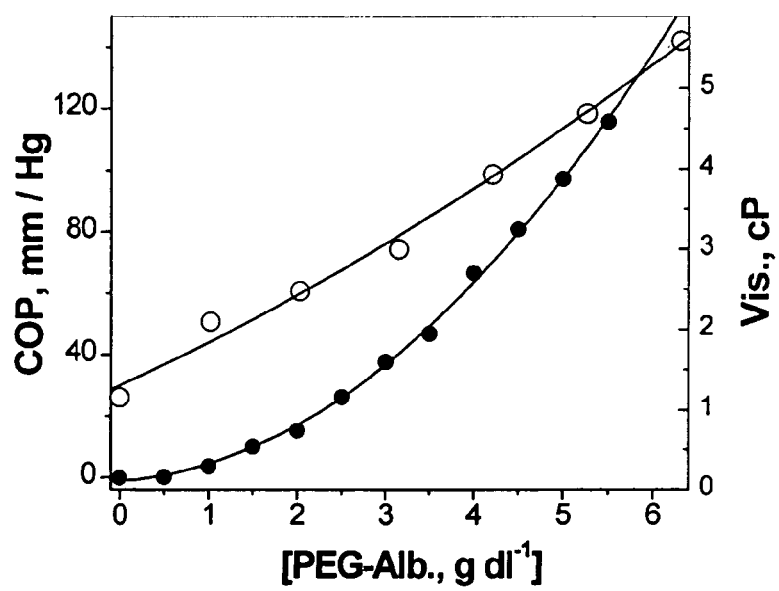
FIG. 20 ued States, 40
ALBUMIN-BASED COLLOID COMPOSITION HAVING AT LEAST ONE PROTECTED THIOL REGION, METHODS OF MAKING, AND METHODS OF USE

GOVERNMENT NOTICE

This invention was made with government support under Cooperative Agreement No. DAMD 17-97-2-7016 awarded by the U.S. Army Medical Research Acquisition Activity. The government has certain rights in the invention.

CROSS REFERENCE TO RELATED APPLICATIONS

This application claims the benefit of U.S. patent application Ser. No. 10/106,793, filed Mar. 26, 2002.

Throughout this application various publications are referenced by numerals within parenthesis. Full citations for these publications may be found at the end of this application, preceding the claims. The disclosure of these publications in their entireties are hereby incorporated by reference into this application in order to more fully describe the state of the art to which this invention pertains.

TECHNICAL FIELD

The present invention relates to the use of an albumin-based colloid composition, such as PEG-Alb, a polyethylene oxide (such as polyethylene glycol (PEG)) modified albumin, for treatment of such diverse hypovolemic conditions as shock, sepsis, bleeding and surgery.

BACKGROUND OF THE INVENTION

Massive resources have been expended on the development of potential therapies aimed at reversing the hypovolemia that is common to different manifestations of systemic inflammatory response syndrome (SIRS). Sepsis alone accounts for 750,000 cases per year in the United States, resulting in 200,000 deaths (1). This high mortality results from multi organ dysfunction (MODS), which is associated with organ edema secondary to capillary leak (CL). Patients with significant CL are typically managed by administering resuscitation fluids containing osmolytes (e.g., albumin, starches, or dextrans) in addition to vasopressors and other supportive measures.

Capillary leak, which is present in different conditions such as multiorgan dysfunction (MODS), sepsis, trauma, burn, hemorrhagic shock, post-cardiopulmonary bypass, pancreatitis and systemic capillary syndrome, causes morbidity and mortality among a large number of hospital patients. Capillary leak (CL) is a central component of MODS, secondary to severe sepsis and systemic inflammatory response syndrome (SIRS). It is characterized by increased capillary permeability resulting in interstitial edema and decreased tissue perfusion leading ultimately to organ failure and death. The leak aspect of capillary leak syndrome (CLS) is reflected in both the release of water into the interstitial space and high molecular weight components of serum which ordinarily would be retained within the capillaries.

Hypovolemic states often lead to hypoperfusion of vital organs, causing organ dysfunction and ultimately resulting in morbidity and death (2). Hypovolemia can occur either rapidly, as with hemorrhagic shock, or progressively due to an underlying disease, with both types involving a systemic inflammatory process. In hemorrhagic shock, hypovolemia occurs due to a rapid and sudden loss of intravascular volume. Upon resuscitation, an inflammatory process may be triggered in reperfused tissues (ischemia-reperfusion injury) causing endothelial cell (EC) injury and capillary leak (CL) leading to a secondary hypovolemic state. In sepsis and other diseases, systemic inflammation is triggered by the disease and in a similar sequence leads to EC injury, CL, and ultimately hypovolemic shock.

Resuscitation with plasma volume expanders remains a mainstay in treating hypovolemia, but with mixed results. The efficacy and safety of volume expanders, including both colloids (e.g., albumin and starches) and crystalloids, continue to be topics of intense research and controversy (3,4). The unpredictable effectiveness of albumin as a plasma expander may be linked to the severity of the underlying EC injury (5). Specifically, if the endothelial integrity is compromised such that albumin can readily extravasate, the leaking albumin may exacerbate the oncotic gradient favoring CL, as opposed to reversing it.

Though the biological mechanisms that induce CL syndrome are poorly understood, some evidence indicates the involvement of inflammatory cytokines. Fluid replacement with solutions of human albumin is only marginally effective since it does not stop the loss of albumin into the extravascular space. Albumin is important because it is responsible for plasma oncotic pressure as well as for retaining sodium ions in the blood.

Under normal conditions, albumin contributes to about 80% of the total blood colloid osmotic pressure (6) and is ideally sized such that it extravasates at a low physiologic rate (7). In CL patients, 5% to 20% albumin solutions are often administered to increase circulating blood volume and to augment intravascular osmotic properties. This method of retarding CL makes the tenuous assumption that albumin can maintain its normally low extravasation rate during shock. Clinical data, however, show that the efficacy of albumin is inconsistent at best (8,9). Some have even suggested that resuscitation with albumin may increase mortality in critically ill patients (10).

PEGylation has been used extensively (11,12). Modification of interferon beta-1a with polyethylene glycol prolongs its half-life, resulting in higher antiviral activity (13). There have been studies on the use of PEGylated hemoglobin (PEG-Hb) as a substitute for blood (14,15,16). Large amounts of PEG-Hb, constituting up to 80% vascular volume showed that PEG-Hb is effective in maintaining the hemodynamics and oxygen delivery in the rat (17). These studies suggest that PEG-Hb is safe even at very high doses.

Other colloids have been used to treat capillary leak conditions with varying degrees of efficacy. A variety of heterogeneous ($M_r$ weighted average: 125,000-450,000 Da) starch colloids have been proposed or are in use as substitute for albumin (18). While these compounds are less expensive and more readily available than pooled human albumin, use of starch colloids has been restricted to low doses due to safety issues that severely limit their use. In addition, the high $M_r$ (>1,000,000 Da) moieties within the heterogeneous starch colloids can alter blood rheological properties and cause coagulopathy (19). The relatively homogeneous Pentastarch ($M_r$=110,000) has been shown to attenuate lung injury in an aortic occlusion reperfusion injury model (20).

In a recent study, MAP and heart rate (HR) did not change favorably when hetastarch (HES) was given in a septic pre-treatment rat model (21). In contrast, favorable changes in MAP (increased) and HR (decreased) were observed in rats pre-treated with polymerized hemoglobin. This occurred despite the fact that, at the same molar concentrations, the colloid osmotic pressure of HES (27 mm/Hg) was higher than the polymerized hemoglobin (21 mm/Hg). Use of the latter as a routine plasma expander is however controversial and is complicated by potential side effects particularly in relation to the kidneys.

Finally, several studies have suggested that albumin has an endothelial anti-apoptotic effect by mediating regulation of cellular glutathione and nuclear Factor Kappa B activation (22,23,24). This may play a significant role in sepsis induced CL particularly in light of a recent report that linked CL in different systemic inflammatory response manifestations to endothelial cell apoptosis (25).

The available albumin today has a molecular weight of 69,000 with a very short half-life (4-6 hours) which can easily leak to the extravascular space in capillary leak conditions such as severe sepsis, pancreatitis, burn and trauma. This leaking can cause worsening edema and/or compartment syndrome. The use of pentastarch and hexastarch are of limited value since they are not for use in pediatric patients and can cause bleeding. Additionally, only 15 cc/kg can be used in patients. Further, the pentastarch and hexastarch have been shown to cause intractable pruritus (itching) after use and the effect lasted for years. In fact, some studies state that the use of albumin as a replacement or as a volume expander is counterproductive since it increases edema by drawing fluid out of the capillaries.

Therefore, there is a great need for a composition and a method to effectively prevent and/or treat hypovolemic conditions which does not have the above-described disadvantages.

In particular, it is to be noted that Hemorrhagic shock (HS) is a leading cause of death following trauma (1a-3a). Early management requires, in addition to controlling the hemorrhage, providing fluid therapy to restore tissue perfusion. The choice of initial fluid therapy can have a significant impact on the outcome. After hemorrhagic shock and resuscitation, nuclear factor-κB (NF-κB) is activated, triggering an inflammatory response, characterized by overproduction of cytokines such as TNF-α, chemokines and cell adhesion molecules which activate endothelial cells (EC), macrophages, neutrophils and other cells (4a). These activated cells (5a, 6a) generate oxidation products such as reactive oxygen species (ROS) which cause vascular damage and capillary leak (CL) (7a-10a). Oxidants and free radicals produced following reperfusion are potent inducers of apoptosis (11a), especially of the EC. Shrinkage of these cells worsens the widening of the inter-endothelial cell gaps and exacerbates the capillary leak (12a) leading to albumin loss. In this environment of oxidative stress with low levels of albumin, endothelial integrity is compromised (32a,34a,35a). Oxidation products, cytokines and vascular depletion, worsened by CL, contribute to vascular unresponsiveness to intrinsic and extrinsic pressors (10a, 13a, 14). These events are summarized in FIG. 11.

In another area of note, recent studies indicate that the type of fluid used in hemorrhagic shock resuscitation affects the physiologic response, the immune response and the systemic inflammatory state.

Crystalloids—Lactated Ringer's (LR) and artificial (synthetic) colloids activate neutrophils and up-regulate cell adhesion molecules; these effects are not seen with albumin or fresh whole blood (10a,11a). Moreover, animals resuscitated with LR or artificial colloids developed significant apoptosis, especially in the lungs and spleen (15a, 16a). Aggressive high volume resuscitation, without controlling the bleeding, can exacerbate the hemorrhage by disrupting the early formed soft thrombi, and by diluting coagulation factors (17a). Conversely, small volume resuscitation using hypertonic saline (7.5%, HTS) alone or in combination with a synthetic colloid is superior to high volume resuscitation, especially in head trauma and in patients at increased risk for developing abdominal or extremity compartment syndrome. However, adverse effects have been reported with small volume HTS used alone or in combination with a synthetic colloid, including hyperchloremic acidosis (18a), and anaphylactoid reactions linked to the colloid component (19a). Other fluids in preclinical testing, such as lactate ethyl pyruvate and ketone based fluids, show less cellular injury and better survival in hemorrhaged animals compared to LR (20a, 21a).

Colloids—The efficacy and safety of colloid plasma expanders, including albumin, are controversial (22a, 23a). Artificial colloids, including starches (24a), have been substituted for albumin in treating capillary leak conditions with varying efficacy. While less expensive and more readily available than human albumin, starch colloids are restricted to low doses because the high $M_r$ (>1,000,000) components alter blood rheological properties and cause coagulopathy (23a). In contrast to albumin, synthetic colloids activate inflammatory and apoptotic processes (25a). Albumin does not increase expression of neutrophil adhesion molecule CD-18, an important step in reperfusion injury, while artificial colloids do (26a). Albumin, which accounts for 80% of blood colloid osmotic pressure (27a), extravasates at a low physiologic rate (28a). In patients with CL, 5% or 25% albumin solutions are administered to increase blood volume and to maintain the oncotic gradient. The efficacy of albumin treatment is variable (29a) and some studies indicate that albumin resuscitation may actually increase mortality (30a). However, a recent randomized double blind controlled clinical study in New Zealand and Australia, involving more than 7000 trauma patients receiving normal saline or 5% albumin, showed no difference in 28 day mortality between the two groups (31a), (study presented by Dr S. Finfer at the 33 rd Congress of Society of Critical Care Medicine, February 2004, Orlando, Fla.).

Albumin as an anti-apoptotic and anti-inflammatory agent—In spite of the conflicting studies of the clinical efficacy of albumin resuscitation, a number of lines of evidence indicate that albumin maintains the integrity of the vascular endothelium (32a-34a) by filling hydrophilic pores of the endothelial surface layer, contributing to their stability (35a). Studies employing human tissue explants in rat skin (36a, 37a) indicate that albumin inhibits endothelial cell apoptosis. Albumin acts as a source of thiol groups (Cys-34); this effect has been demonstrated in septic patients with increases in overall thiol concentration of up to 50% following administration of 200 ml 20% albumin (38a). In vitro mechanistic studies showed that albumin exerts its endothelial anti-apoptotic effect by regulating cellular glutathione and NF-κB deactivation. Physiological concentrations of albumin inhibit TNFα induction by inhibiting NF-κB activation (39a). In a rodent model of HS, 25% albumin resuscitation diminished NF-κB translocation and cytokine-induced neutrophil chemoattractant messenger RNA concentrations (40a).

However, it is also to be noted that albumin is ineffective in hemorrhagic shock. The ineffectiveness of unmodified albumin as a plasma expander in the previous studies (27a, 29a, 30a) may be linked to the severity of the underlying endothelial cell injury. If the endothelial integrity is compromised such that albumin can readily extravasate, the leaking albumin may exacerbate the oncotic gradient favoring capillary leak (41a).

SUMMARY OF THE INVENTION

One aspect of the present invention relates to a composition comprising an albumin-based colloid composition. In one aspect, the albumin-based colloid composition is modified such that its hydrodynamic radius is sufficiently large to preclude its leaking through the capillaries while retaining its oncotic properties and its ability to bind ligands such as sodium ions, fatty acids, drugs and bilirubin. While a number of proteins have been modified with polyethylene glycol, attached through the ε-amino group of lysine, without loss of biological activity and without significant toxicity. The present invention contemplates the use of PEGylation products which expand the composition's hydrodynamic ratio to a degree such that, when administered to a patient suffering from a hypovolemic state, with a danger of developing multiorgan dysfunction (MODS) the albumin-based colloid composition reverses the hypovolemic condition.

The albumin-based colloid composition of the present invention is especially useful for volume expansion in states of shock such as severe sepsis, shock, pancreatitis, burn and trauma, thereby improving survival rates in those conditions.

The albumin-based colloid composition is also useful as a hyperosmotic agent driving, or causing, ultra filtration in peritoneal dialysis. Still other uses include, for example, use in head trauma, hyperviscosity states, patients with liver cirrhosis following parcenthesis, Leukopheresis, nutritional albumin deficiency, nephrotic syndrome, liver failure, severe hypoalbuminemic patients, and severe burn patients.

In one aspect, the present invention comprises a composition of an albumin-based colloid composition having a preferred degree of hydration. The present invention further relates to two methods to produce the albumin-based colloid composition by modifying the albumin with polyethylene oxide: one is by using N-hydroxysuccinamide esters and the other is by using cyanuric chloride derivatives. The albumin-based colloid composition of the present invention is safe and has an extended useful half-life measured at least three times that of the normal albumin in normal rats and likely more prolonged in septic rats. The albumin-based colloid composition can be synthesized using recombinant albumin which decreases its immunogenicity.

The albumin-based colloid composition has a lessened tendency to extravascate because of its larger size, thereby avoiding worsening of the hypovolemic condition such as capillary leak syndrome and clinically, edema and compartment syndrome.

In another aspect, the volume-expanding properties of the albumin—based colloid (or example, albumin with covalently attached polyethylene glycol (PEG-Alb) is a large albumin-based colloid composition which has a greater degree of hydration (13-16 times compared to albumin) and a larger hydrodynamic radius (3.4 nm vs 10 nm). The albumin-based colloid composition is less likely to enter the extra vascular space than normal albumin. Additionally, the albumin-based colloid composition retains the important physiologic functions of albumin, including roles as an osmolyte, as an antioxidant, and as a transporter of less soluble metabolites such as heme and bilirubin; the latter two features are not associated with other crystalloids and colloids.

In one aspect, the present invention relates to a composition comprising a large albumin-based colloid with a preferred degree of hydration. The composition is an albumin-based colloid and, in one embodiment, comprises a polyethylene glycol modified albumin having a hydrodynamic radius sufficiently large to preclude the molecule from leaking through a patient's capillaries. In certain embodiments, the albumin-based colloid composition has an average molecular weight of at least 128,000 daltons. The composition can comprise human albumin, bovine serum albumin, lactalbumin, or ovalbumin.

The albumin-based colloid composition has an ability to bind ligands such as sodium ions, fatty acids, bilirubin and therapeutic drugs.

In another aspect, the present invention relates to an in vivo method of preventing or treating hypovolemic conditions and its complications such as multiple organ dysfunction syndrome comprising administering a therapeutic amount of the large albumin-based colloid composition to a patient in danger of developing such conditions.

In another aspect, the present invention relates to a method for the prevention of mammalian tissue injured or at risk of injury comprising the administration of a therapeutic amount to a mammal of a composition comprising an albumin-based colloid. Example solid organs preservation before transplantation. The composition is incapable of leaking through the mammal's capillaries and is present in an amount of sufficient to protect the tissue from injury. The method is especially useful where the risk of injury is due to hypovolemia, sepsis, shock, burn, trauma, surgery, predisposition to capillary leak, hyperviscosity stress, hypoalbuminemia, and/or anoxia.

Yet another aspect of the present invention relates to a method for forming an albumin-based colloid composition which comprises modifying albumin with polyethylene oxide. The albumin is modified by using N-hydroxysuccinamide esters, or, alternatively, is modified by using cyanuric-chloride derivatives. In certain embodiments, the method includes dissolving albumin in potassium phosphate to form an albumin solution, activating methoxy polyethylene glycol with cyanuric chloride and dissolving in water to form a methoxy polyethylene glycol solution, adding the methoxy polyethylene glycol solution to the albumin solution to form a mixture, stirring the mixture for a suitable time at about room temperature, dialyzing the mixture against a phosphate buffered saline solution at about 4° C. for a suitable time, and collecting polyethylene glycol modified albumin. In certain embodiments, the ratio of a volume of the methyoxy glycol solution to a volume of the albumin solution is in the range of about 1 to about 3.

DESCRIPTION OF THE FIGURES

The patent or application file contains at least one drawing executed in color. Copies of this patent or patent application publication with color drawing(s) will be provided by the Office upon request and payment of the necessary fee.

FIGS. 3A-D show the typical histopathologic changes seen in the different treatment groups.

FIG. 5 (Left) the results are presented as $V_e/V_0$ vs $M_r$. Upward vertical arrows with numbers correspond to approximate elution positions indicated by arrows.

FIG. 6 shows SELDI Mass spectrometry of PEG-Alb and albumin.

FIG. 17a, Mild (0-1)

FIG. 18A is Table I which shows the Hematocrit (Htc) and Colloid Osmotic Pressure (COP) in Hemorrhagic Shock Rats, where Data mean±SD. *=p<0.05; **=p<0.01 where comparisons for all groups are relative to the corresponding treatment end treatment compared to before treatment values via paired t-tests; a) Before treatment and after treatment, within same group; b) Between Saline and Albumin; c) Between Saline and PEG-Alb; d) Between Albumin and PEG-Alb; (NS) not significant.

FIG. 19 shows a hemorrhagic shock model (phases I & II) where the numbers below correspond to minutes after hemorrhage.

FIG. 20 shows the dependence of colloid osmotic pressure (solid circles) and viscosity (open circles) on PEG-Alb concentration.

FIG. 30A: unfolding of unmodified human albumin monitored by CD. FIG. 30B: unfolding of mPEG5000 modified human albumin monitored by CD. Differences in scales reflect different protein concentration.

DESCRIPTION OF THE PREFERRED EMBODIMENTS

Figures 1A, 1B:
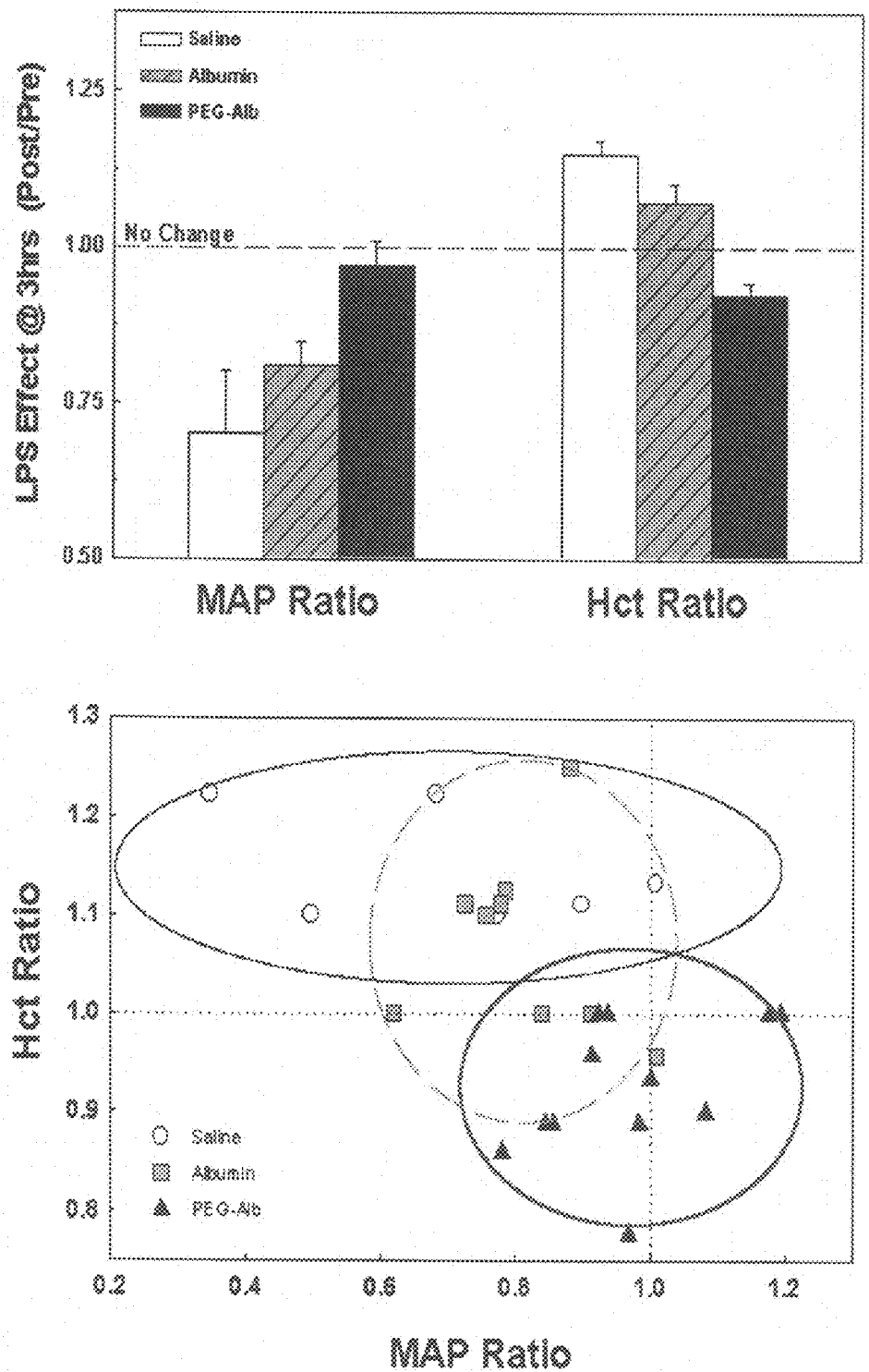
FIG. 1A is a graph showing change in hematocrit (%) for the saline, albumin and PEGA groups.
FIG. 1B shows the correlation of mean arterial pressure with hematocrit.

According to one aspect of the present invention, unlike starches, the albumin-based colloid composition retains the important physiologic functions of albumin, including roles as an osmolyte, as an antioxidant (26), and as a transporter of less soluble metabolites such as heme and bilirubin (27); the latter two features are not associated with other crystalloids and colloids. Protein unfolding studies performed on PEG-Alb indicated that albumin functionality is highly preserved).

According to the present invention, the colloid oncotic properties of the albumin-based colloid composition are superior to those of unmodified albumin with regard to plasma volume expansion during treatment of hypovolemia. The albumin-base colloid composition reduces the likelihood of end organ injury, and hence morbidity and mortality, in critically ill patients. The present invention also relates to a method for the pretreatment of septic patients to prevent or ameliorate ARDS (Acute Respiratoty Distress Syndrome) and maintain blood pressure. The albumin-based colloid composition of the present invention, with its larger averaged molecular weight (128,000 daltons) and augmented colloid osmotic function, is vastly superior to saline or albumin with regard to improving the physiological and histologic manifestations of endotoxin-induced shock.

The albumin-based colloid composition is kept in the intravascular compartment in patients, even in sepsis conditions where capillary leak occurs. In the lipopolysaccharide (LPS) induced model of sepsis in rats, there was no difference in hematocrit (HCT) pre-experiment, however after inducing sepsis, the hematocrit of the saline and albumin treated groups increased while that of the PEG-Alb group decreased. FIG. 1 shows the positive difference in the post-pre hematocrit in groups 1 and 2 while there is a negative difference in the post-pre hematocrit of group 3 (PEG-Alb group). The data also shows that albumin tends not to be different with respect to hemoconcentration as well as loss of fluid into the interstitial space.

Figure 2:
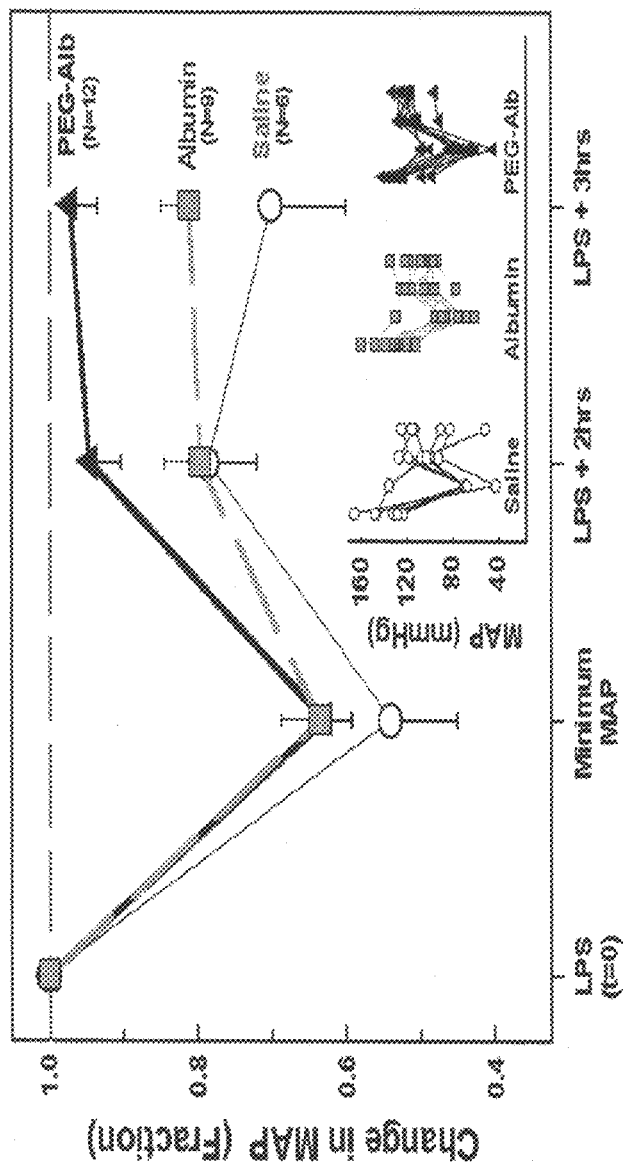
FIG. 2 is a graph showing changes in blood pressure (i.e., mean arterial pressure MAP) (Normalized $P_{art}$) immediately after injection of endotoxin (ET), two hours post injection of ET, and three hours post injection of ET.

The maintenance of blood pressures in sepsis is also important. The efficacy of PEG-Alb, saline and albumin treatments for prevention of sepsis induced hypotension are shown in FIG. 2. At 2 and 3 hours after LPS (lippopolysaccharide), MAP (mean arterial pressure) was decreased compared to baseline values in both albumin and saline treated groups. Alternatively, the average response in PEG-Alb rats was unchanged at both times. Changes in MAP after LPS showed noticeable variability even within treatment groups. Nevertheless, the increased efficacy of PEG-Alb in maintaining MAP was statistically significant (two-way repeated measures ANOVA; P=0.023).

Figure 4:
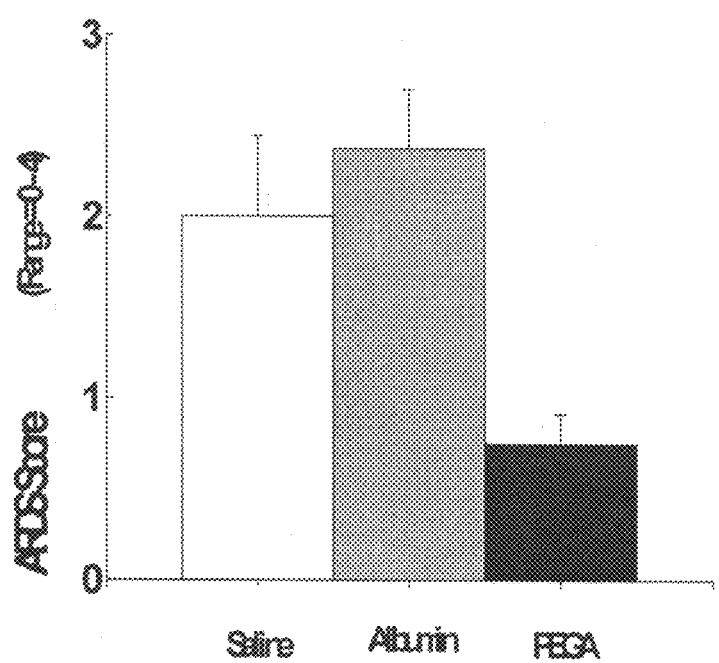
FIG. 4 shows the acute respiratory distress syndrome (ARDS) score of each treatment group.

The histopathologic findings clearly show that the PEG-Alb treated group exhibits less alveolar damage than the albumin group. (FIGS. 3A-D). Lung injury (acute respiratory distress syndrome (ARDS) was significantly less (one-way ANOVA; P-0.002) in PEGA treated rats compared to both albumin and saline treated rats, as shown in FIG. 4. Given the minimal infiltrates and hyalinization in the lung tissues of PEG-Alb rats compared to the positive controls and albumin treated rats, PEG-Alb treatment is better than albumin in LPS-induced hypovolemia.

Figure 5:
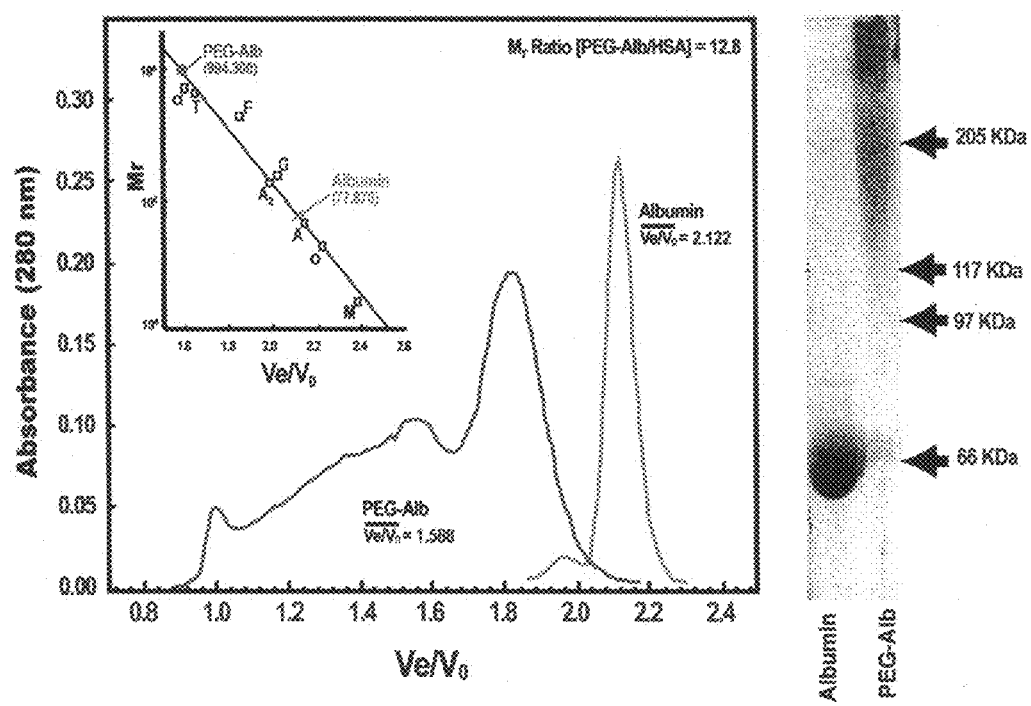
FIG. 5 (Right) shows SDS acrylamide gel electrophoreses showing that estimated MW of PEG-Alb is ≧950,000 Daltons. Analytical Gel filtration of PEG-Alb showing samples of albumin, PEG-Alb and standard proteins were chromatographed on Superose 6. The Insert shows vertical arrows with letters indicate the elution position of standard proteins: α, α2 macroglobulin (720,000); thyroglobulin (660,000 $M_r$); F, appoferritin (440,000); $A_2$, albumin dimer (133,000); G, IgG (160,000); O, ovalbumin (45,000); M, myoglobin (17,000).

FIG. 5 (Left) shows the SDS-Acrylamide gel electrophoresis of PEG-Alb.

Lanes 1 and 4 contain standard markers which are from top to bottom: 1) Myosin (MW 205 KD); 2) Phosphorylase (97 KD); and 3) Bovine serum albumin (66 KD). Lanes 2 contains human serum albumin after pegylation and its molecular weight over 200 KD. Lane 3 contains human serum albumin before pegylation.

FIG. 5 (Right) shows the gel filtration of PEG-Alb on Superdex S200-PEGA size standards was applied to Superdex equilibrated in 10 nM $KPO_4$, 150 nM NaCl. Standards indicated are thyroglobulin (Thyr), immunoglobulin (IgG), albumin (alb), ovalbumin (OVAL) and Myoglobin (My). Peg-albumin eluted as two weeks: Peak I was the void volume and Peak II eluted after thyroglobulin.

According to the present invention, pretreatment of rats with PEG-Alb prior to induction of sepsis with LPS dramatically reduces the manifestations of LPS-induced shock when compared to pretreatment of animals with saline or unmodified albumin. High dose of LPS was given because rodents are relatively resistant to LPS, and sustained hypotension is needed to simulate the severe human sepsis with MODS. PEG-Alb gives a more rapid recovery in blood pressure, a lower hematocrit—suggesting hemodilution as opposed to the hemoconcentration that characterizes CL—and significantly reduced lung injury. The larger effective size of the PEG-Alb molecule renders it less likely to extravasate in the presence of cell injury and during a loss of endothelial integrity.

The shock that follows administration of an endotoxin is characterized by a biphasic blood pressure response. In the first phase, a drop in blood pressure occurs 10-15 minutes after LPS is injected. This was evident in all of the LPS-injected animals, suggesting that PEG-Alb does not act by neutralizing the endotoxin itself. The second phase of hypotension is caused predominantly by the action of inducible nitric oxide (iNOS), which substantially reduces plasma volume (28). It is during this second phase that PEG-Alb has a superior effect when compared with albumin or saline. Although iNOS m RNA or peptide was not measured, it is very likely under these conditions employed here; i.e., intravenous administration of 20 mg/Kg LPS that iNOS was induced. While inherent limitations exist with any pretreatment model, the data show that administering PEG-Alb prior to LPS protects rats from developing ARDS.

The hematocrit, mean arterial pressure, and histology all indicate that PEG-Alb is a beneficial treatment for the LPS-induced hypovolemia. Both the hemodilution and the unchanged MAP achieved with the PEG-Alb treatments are indicative of plasma volume expansion (or at least maintenance), while the opposite effects were observed with both albumin and saline. Maintenance of intravascular volume with PEG-Alb is consistent with reduced capillary leak. Histopathologic findings (FIGS. 3A-D) show minimal interstitial infiltrates and hyalinization in the lung tissues of PEG-Alb-treated rats. Immunflourescence studies show that PEG-Alb tends to be retained in the vascular space to a greater extent than albumin during capillary leak (FIG. 3).

The improved colloidal properties of PEG-Alb result from increased hydrophilic properties, which are shown by its very large hydrodynamic radius—as reflected in its behavior on a gel filtration column and its larger molecular radius of gyration ($R_G$) and excluded volume ($\Lambda$) as inferred from its non-ideal osmotic properties. This was also demonstrated using size exclusion chromatography where the elution ratio of PEG-Alb/albumin agreed with the excluded volume of PEG-Alb/albumin (FIG. 5) using colloid osmometry. Similarly increased $R_G$ and $\Lambda$ of proteins after modification with covalent bonding with one or more PEG groups were previously reported in case of bovine hemoglobin by Winslow and colleagues (29).

The colloid oncotic properties of PEG-Alb are superior to those of unmodified albumin with regard to plasma volume expansion during treatment of hypovolemia associated with CL. PEG-Alb is useful to reduce the likelihood of end organ injury, and hence morbidity and mortality, in critically ill patients. The present invention is useful in the pretreatment of patients to prevent or ameliorate ARDS and maintain blood pressure. PEG-Alb, with its larger molecular weight and augmented colloid osmotic function, is vastly superior to saline or albumin with regard to improving the physiological and histologic manifestations of endotoxin-induced shock.

The following examples are provided merely to further illustrate the present invention. The scope of the invention shall not be construed as merely consisting of the following examples.

EXAMPLE I

Use of Polyethylene Glycol Modified Albumin (PEG-Alb) in Sepsis

Materials and Methods: Preparation of PEG-Alb. 2 gms of human albumin (Sigma, St. Louis, Mo.) was dissolved in 45 ml. of 50 MM of potassium phosphate (mixture of mono and dibasic), pH 7.4. 500 mg of methoxy polyethylene glycol (Sigma, St. Louis, Mo.) was activated with cyanuric chloride and dissolved in 4 ml. of water. 1.4 ml of methoxy polyethylene glycol solution was added to 45 ml of the human albumin solution and the mixture was stirred for two hours at room temperature. The mixture was transferred to a dialysing tube (molecular weight cut off –12500) and dialysed against 3000 ml of phosphate buffered saline at 4° C. for 72 hours. The polyethylene gylcol modified albumin (PEGA) was collected and then frozen at –20° C. until its use.

Animals. Adult male Sprague-Dawley rats (Charles River Laboratories, Portage, Mich.) weighing 400-480 grams were used. Animals were housed in an American Association for Accreditation of Laboratory Animal Care, International (AAALACI) approved facility. They were provided standard rat chow and water ad libitum. All protocols were approved by the Institutional Animal Care and Use Committee and the ABC (Hazard) Committee.

Methods:

The animals were fasted overnight, but given water ad libitum. Animals were anesthesized using Sodium pentobaribital (50 mg/kg) intraperitoneally and given additional doses as needed during the course of the experiment. An arterial cathether (Intramedic PE-50, Clay Adams) was placed on the carotid artery and hooked to the transducer/amplifier for continuous blood pressure monitoring (TestPoint, Capital Equipment Corporation, Billerica, Mass.). An intravenous line was placed on the opposite internal jugular vein using G24 cathether. A blood sample was taken from the carotid line for baseline hematocrit and albumin and replacement fluid (1 ml 0.9% saline) was infused via the intravenous line. Normal saline 5 ml was infused in group 1. Albumin 0.6 gms/kg bodyweight (BW) was given to group 2 and PEGA 0.6 gms/kg BW was given to group 3. After 30 minutes, endotoxin (LPS) (Sigma Chemicals, St. Louis, Mo.) was given to the three groups at varying doses. The rats were divided into 3 groups based on the received resuscitation fluid: Group 1 (n=9) received unmodified albumin in normal saline solution at a 0.6 gm/kg dosage; the injection concentration of albumin was 40 mg/ml, yielding an injection volume of 1.5 ml/100 g body weight (BW). Instead of albumin, Group 2 (n=12) received PEG-Alb at the same dosage, protein concentration, and injection volume as at Group 1. Group 3 (n=6) received 1.5 ml/100 gm BW of normal saline. Blood pressure monitoring was done for three hours after endotoxin infusion after which the rats were euthanized.

Post-experiment blood samples for hematocrit and albumin were taken. The right lung was put in formalin and set to pathology for hematoylin-eosin staining.

PEG-modified albumin (PEG-Alb) was examined as a potential plasma volume expander. Albumin modified at multiple sites, exhibited a larger effective molar volume and exerted greater osmotic pressure than unmodified albumin. Solutions of PEG-Alb, albumin, and saline were tested in a rat endotoxin-induced model of shock. Pretreatment with polyethylene glycol modified-human albumin (PEG-Alb) maintained mean arterial pressure (p=0.023), retained volume as evidenced by hemodilution (p=0.001) and attenuated the histologic manifestations of acute respiratory distress syndrome (ARDS) (p=0.002). Rats were pretreated with fluorescence labeled PEG-Alb and rhodamine labeled albumin, separately and in combination, followed by treatment with LPS. Fluorescence microscopy of lung sections indicated that fluorescence-labeled PEG-Alb was retained within the blood vessels rhodamine-labeled albumin was not. Compared with the use of saline or unmodified human albumin, PEG-Alb is a useful alternative plasma volume expander that may be of use in hypovolemic states.

EXAMPLE II

Use of PEG-Alb to Restore Vascular Volumes and Attenuate Acute Lung Injury in Endotoxin-induced Shock Preparation of albumin and PEGA (PEG-Alb)

Methoxypolyethylene glycol cyanuric chloride (average $M_r$ 5000) was added to human albumin (type V, Sigma Chemical Co.) dissolved in 50 mM $KP_I$ (pH 7.5) at 50 to 60 mg/ml with gentle stirring four times (0.2 mg per mg of albumin per addition) at 10-minute intervals at 22° C. The reaction was allowed to stir 40 minutes after the last addition of the reagent. Modification was rapid, being complete in less than 15 minutes at room temperature with the extent of modification depending primarily on the amount of reagent added. Prior to infusion into animals, both albumin and PEG-Alb were dialyzed against phosphate-buffered saline for 48 hours with three changes of buffer using high-molecular-weight-cutoff dialysis tubing (50 kDa molecular mass cutoff).

FITC-Albumin and FITC-PEG-Alb.

Human albumin (50 mg/ml) was incubated 1 hr in 50 mM $KP_i$ (pH 7.5), 150 mM NaCl, and 0.5 mM dithiothreitol. The dithiothreitol-treated albumin was incubated two hours with 4 mM 5-iodoacetamido fluorescein or 1.5 mM tetramethyl-rhodamine-5-iodoacetamide. The flourescein-modified albumin was dialyzed 48 hours against four changes of phosphate-buffered saline to remove free flourescein. Rhodamine-labeled albumin was chromatographed on Sephadex 50 followed by extensive dialysis against phosphate-buffered saline.

Some of the flourescein-labeled albumin was modified with methoxypolyethylene glycol cyanuric chloride and purified by gel filtration on Sephacryl S200. Fractions from Sephacryl S200 eluting with apparent molecular weights in excess of 200,000 were pooled and concentrated using an Amicon ultrafiltration cell with a PM10 membrane. Analysis of the flourescein and rhodamine-labeled albumins by gel electrophoresis revealed that the fluorescence was associated with the protein; no fluorescence was detected at the positions of free flourescein or rhodamine.

Physiological Studies

Experimental protocols were approved by the Institutional Animal Care and Use Committee (IACUC) and the Academic Chemical Hazardous Committee (ACHC) at the Medical College of Ohio. Adult male Sprague-Dawley rats (Charles River Laboratories, Portage, Mich.) weighing 400-480 grams were used. Animals were housed in an American Association for Accreditation of Laboratory Animal Care, International (AAALACI) approved facility. They were provided standard rat chow and water ad libitum. Prior to the experiment, the animals were fasted overnight, but given water ad libitum.

All rats were anesthetized using sodium pentobarbital (50 mg/kg body weight) intraperitoneally followed with additional intravenous maintenance doses at 1 hour intervals. Mean arterial pressure (MAP) was continuously measured via a catheter (Intramedic PE-50, Clay Adams) placed in the right carotid artery and attached to a blood pressure transducer and amplifier (BLPR and TBM4, World Precision Instruments, Sarasota, Fla.) and collected on a computer (TestPoint, Capital Equipment, Billerica, Mass.). An intravenous line for infusion was inserted in the left jugular vein (G24 Protectiv*Plus, Johnson and Johnson/Ethicon, Arlington, Tex.).

The rats were divided into 3 groups based on the received resuscitation fluid: Group 1 (n=9) received unmodified albumin in normal saline solution at a 0.6 gm/kg dosage; the injection concentration of albumin was 40 mg/ml, yielding an injection volume of 1.5 ml/100 g body weight (BW). Instead of albumin, Group 2 (n=12) received PEG-Alb at the same dosage, protein concentration, and injection volume as at Group 1. Group 3 (n=6) received 1.5 ml/100 gm BW of normal saline. A 1 ml baseline blood sample was taken for baseline hematocrit (Hct) measurement from the carotid line and replaced with the same volume of 0.9% saline. MAP monitoring was initiated at the start of the fluid infusion. After 30 minutes, 20 mg/kg BW of Endotoxin (*E. Coli* lipopolysaccharide [LPS] from serotype 055: B45, Sigma Chemicals, St. Louis Mo.) dissolved in 1 ml of saline was administered, and the rats were monitored for 3 hours thereafter. A blood sample was then taken for post sepsis Hct assessment, and then rats were euthanized with 150 mg/kg/BW of Pentobarbital IP and exsanguinated. Finally, one kidney and the lungs were harvested and immediately fixed in 10% formalin for subsequent histologic examination.

Histologic Studies

The lung and kidney tissues were removed from formalin solution and subjected to standard processing, including a hematoxylin and eosin stain. These coded preparations were examined with a light microscope by a blinded pathologist, who scored the inflammatory histopathologic features using the following five-point system: 0=no significant histopathologic changes; 1=minimal interstitial inflammatory infiltrates; 2=mild interstitial inflammatory infiltrates with mild hyalinization; 3=moderate interstitial inflammatory infiltrates with moderate hyalinization; 4=severe interstitial inflammatory infiltrates with severe hyalinization. In order to ensure consistency, the same pathologist examined samples on two separate occasions, and the averaged score was used.

Molecular/Biophysical Studies

SDS Gel Electrophoresis. Samples of unmodified albumin and PEGA were prepared for electrophoresis by adding SDS (1%, W/V) and beta mercaptoethanol (5%, V/V) and heating in a boiling water bath for 1 minute. Samples were subjected to electrophoresis on 7.5% or 10% acrylamide gels (30).

Size Exclusion Chromatography.

Albumin and PEGA were analyzed by size-exclusion chromatography on a 24 ml bed volume Superose 6 column (Pharmacia). Samples or a mixture of standards (in 0.5 ml) were applied to the column and eluted with 10 mM potassium phosphate (pH 7.5) and 150 mM NaCl at 0.5 ml min$^{-1}$. Absorbance at 280 nm was monitored continuously.

SELDI-TOF Protein Analysis.

Surface-enhanced laser desorption/ionization-time of flight (SELDI-TOF) mass spectrometry was used to characterize the PEG-albumin and albumin samples. One microliter of sample (at 1 to 5 mg ml$^{-1}$) was deposited and allowed to air dry directly onto a 2 mm spot of an alaphatically coated aluminum ProteinChip array (H4 ProteinChip, Ciphergen Biosystems, Palo Alto, Calif.). Twice, one half microliter of energy absorbing matrix (EAM, a saturated solution of 3,5-Dimethoxy-4-hydroxycinnamic acid in aqueous 50% acetonitrile and 0.5% triflouroacetic acid) was applied to the sample and allowed to air dry.

The ProteinChip array was transferred to a ProteinChip reader and a laser (N2 320 nm-UV) was focused on the sample in a vacuum chamber. After 2 warming laser shots, proteins absorbed to the matrix were ionized and desorbed from the array surface. Ionized proteins were detected and molecular masses were determined using TOF analysis. The TOF mass spectra were collected in the positive ion mode with a ProteinChip System (PBSII series, Ciphergen) using Ciphergen Peaks (version 2.1b) software. Real-time signal averages of 65 laser shots were averaged to generate each spectrum.

Colloid Osmotic Pressure (COP).

Both PEGA-Alb and albumin were prepared for COP measurements in similar fashion. Briefly, samples were dissolved in 10 mM potassium phosphate (pH 7.5), 150 mM NaCl at 50 mg ml$^{-1}$, treated with dithiothreitol (0.5 mM dithiothreitol) for 1 hour at 30° C., and then incubated with iodoacetamide (5 mM iodoacetamide) for 1 hour at 30° C. The acetamidated albumin (5 ml at 50 mg ml$^{-1}$) was then subjected to chromatography on Sephacryl S300 (2.8 cm×40 cm) equilibrated in 10 mM potassium phosphate (pH 7.5) and 150 mM NaCl to reduce albumin dimer and other low and high molecular weight contaminants that otherwise interfere with determination of osmotic pressure. Finally, both albumin and PEGA were dialyzed against several changes of 0.9% NaCl.

COP measurements with each colloid were repeated over a wide range of concentrations using the Wescor Model 4420 colloid osmometer (Logan, Utah). The instrument was blanked with 0.9% saline and calibrated with a 20.2 mOsm albumin standard solution. Note, the concentration of unmodified albumin was determined from absorbance at 280 nm ($\epsilon_{280\,nm,1\%}$=5.31) (31) and were confirmed by dry weight measurements. PEG-Alb concentrations were estimated from dry weight determination.

COP [π] in terms of concentration [c] were analyzed via a nonlinear least squares fit of the equation to estimate 1) estimate the weighted molecular Mass [Mr] reflected from the ideal component of the π-c relation (32) and 2) the non-ideal contributions of all other virial coefficients via the two parameters B and α:

This form of the equation is a slight modification yet more flexible form of the traditionally employed equation [π=RT (c/Mr+Bc$^2$+CC$^3$ . . . )] that avoids a priori assumptions of number of virial coefficients; R=63.364 mm Hg M$^{-1}$, c is concentration (g per dl), and T is temperature (295° K).

Statistical Analysis.

The difference between pre and post-LPS hematocrits among these three treatment groups was compared by ANOVA, whereas two-way repeated measures of ANOVA were used to compare mean arterial pressure (MAP) before LPS and at multiple time points after LPS. Individual differences between groups were assessed using a Tukey multiple-comparison test. A p<0.05 was used to indicate statistical significance.

Physiological Studies

Vascular volume contraction/expansion following LPS—induced sepsis was inferred from the changes in MAP and Hct. Both of these measures varied significantly for rats pretreated with PEG-Alb, albumin or saline. Initially, within 15-25 minutes post LPS bolus infusion, all three groups showed a similar drop of ~40% in MAP (Saline: 135±11 down to 81±30 mmHg; Albumin: 134±14 down to 85±20 mmHg; PEG-Alb: 125±12 down to 79±19 mmHg) (FIG. 2). The MAP recovery that followed was significantly better in PEG-Alb [MAP [3 hrs after LPS]=120±10 mmHg; p=0.023) treated rats compared to both saline (99±29 mmHg) and albumin (108±14 mmHg) treatments. MAP recovery was slightly greater in albumin versus saline treated rats, but this difference was not significant.

Pre-LPS hematocrit was similar in all study groups [44±2 (saline), 42±3 (albumin) and 45±2 (PEG-Alb)]. At 3 hours after LPS, hematocrit (post) was elevated relative to baseline (pre) levels for both the albumin (Hct Ratio (post/pre) =1.09±0.11) and saline (Hct Ratio=1.19±0.09) treated rats indicating a relative decrease in intravascular fluid volume or hemoconcentration (FIG. 1-A). Conversely, PEG-Alb-treated rats exhibited hemodilution after LPS administration (Hct Ratio=0.93±0.07). These trends were highly reproducible within each group, and the differences between treatment groups were highly statistically significant (one-way ANOVA; p=0.001). Most importantly, these changes in HCT were generally correlated to the extent of MAP recovery as evidenced by the clustering of the MAP Ratio vs. Hct Ratio (33). Here, PEG-Alb rats generally exhibited Hct Ratios <1 (i.e., hemodilution) and MAP Ratios at or near 1 (i.e., near complete recovery at 3 hours post-LPS). Alternatively, for saline and albumin treated rats, the post-to-pre MAP Ratios were relatively lower (incomplete MAP recovery) while Hct Ratios were generally >1 (hemoconcentration). FIG. 1(B).

Histologic Studies

Microscopic examination of lung tissue sections taken from PEG-Alb-treated and control (no-sepsis) rats did not reveal significant histopathological changes (FIG. 3.A-D). Alternatively, substantial inflammatory histopathologic changes consistent with severe acute lung injury (ALI), including hyalinization and interstitial lymphocytic infiltrates, were evident in most saline and albumin treated rats (FIG. 3). Overall, the averaged ALI scores (0=No injury; 1=minimal; 2=mild; 3=moderate; 4=severe) were significantly lower in PEG-Alb-treated rats (0.76±0.47; range: 0-1) compared to both the saline (2.0±1.0; range: 0-3) and albumin (2.4±0.9; range: 1-4) groups (One Way ANOVA; P=0.002). In all four groups, microscopic sections of the kidneys showed no significant histopathologic changes.

Results from example normal (FIG. 8.A) and septic (FIG. 8.B) rats infused with a mixture of fluorescein-labeled PEG-Alb (green) and rhodamine-labeled albumin (red) exhibited distinctly different distribution patterns of the two chromofores. Specifically, the alveolar—capillary area of the normal rats was characterized by localized yellow (i.e., red and green) compared to more diffuse distribution of the chlorofores in septic rats particularly the red rhodamine suggesting its extravasation. A consistent finding is also evident from septic rats injected with a single colloid species; i.e., either fluorescein-labeled PEG-Alb (FIG. 8.C) and fluorescein-labeled albumin (FIG. 8.D). Here too, the Albumin treated septic rats exhibited diffuse fluorescence while PEG-Alb treated rats did not.

Biophysical Properties of PEG-Alb

Figure 7:
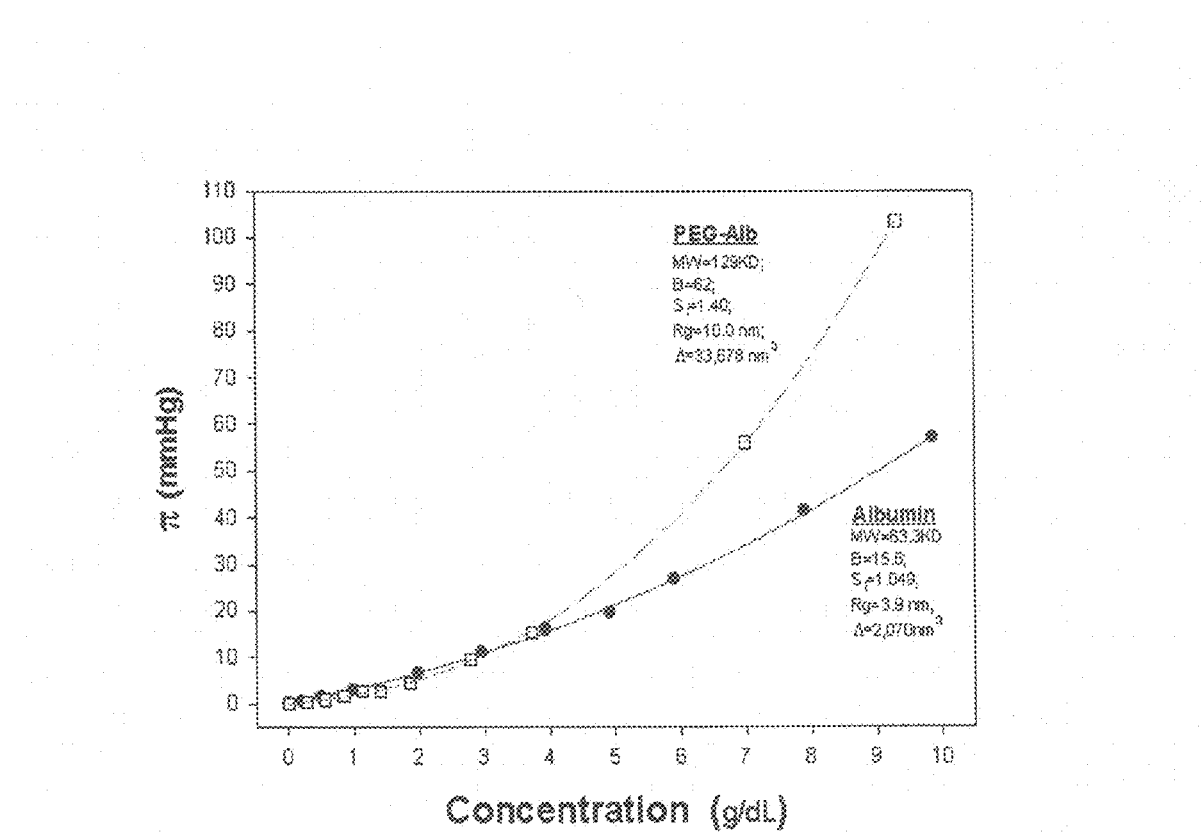
FIG. 7 shows osmotic pressure of PEG-Alb and albumin solutions. The osmotic pressure of solutions of albumin and PEG-Alb were determined as described below and plotted as osmotic pressure (in mm Hg) versus concentration. The line corresponds to a fit to a third order polynomial.
Figure 8A:
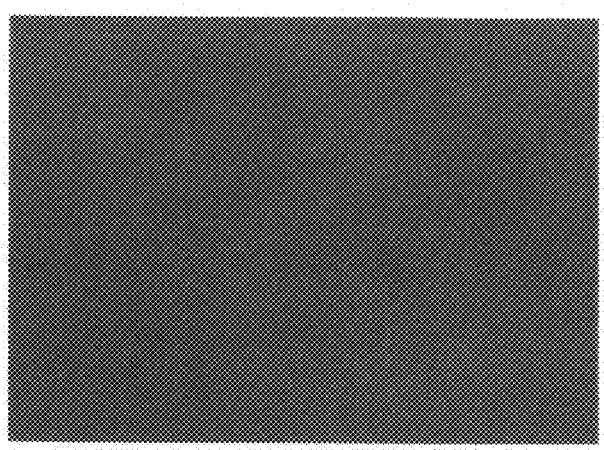
FIGS. 8A-E shows fluorescent pictures showing: A and B, normal animals, no sepsis, there is localized FI-labeled PEG-Alb within the alveolo-capillary membrane, while B, shows an overlap of the Rh-labeled Albumin and FI-labeled PEG-Alb appearing yellow (green & red). While in animals with sepsis (C, D, E), there is a diffuse distribution of the Rh-labeled albumin and there is a pattern of concentration of the PEG-Alb at the alveob-capillary membrane.
Figure 8B:
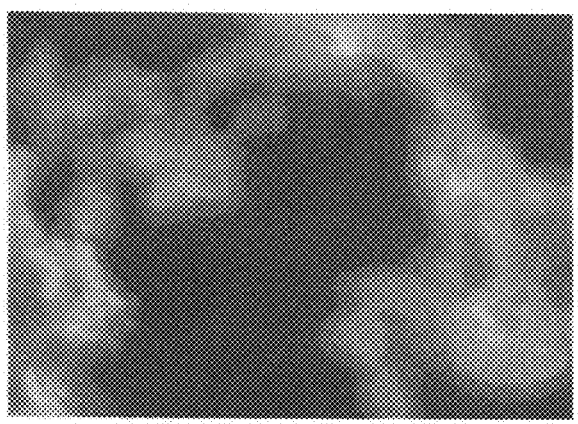
Figure 8C:
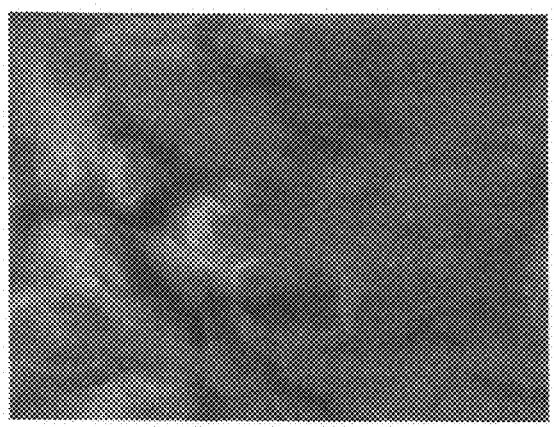
Figure 8D:
Figure 8E:
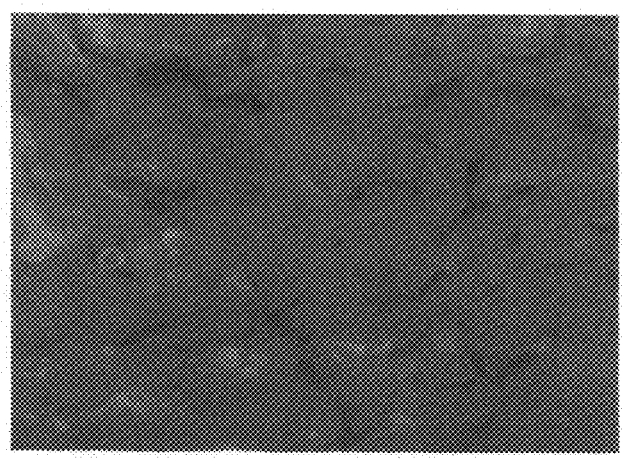

Molecular size—The results of SDS gel electrophoresis of albumin and PEG-Alb are contrasted in FIG. 5A (Right). Expectedly, albumin runs as a fairly homogeneous protein and at its known molecular weight. In contrast, while PEG-Alb ran at higher apparent molecular weights, the PEG-Alb material does not readily enter the gel. Note, in case of non-ideal proteins, the electrophoretic mobility is primarily a reflection of their extended nature rather than their molecular weight. The substantial heterogeneity of the modified protein is due to PEG modification at multiple lysyl residues. PEG-Alb was also examined by gel filtration. Consistent with its behavior on SDS gel electrophoresis, the modified protein is substantially heterogeneous, eluting from the column over an apparent $M_r$ range from 500,000 to several million FIG. 5B (Left). Its behavior on a size-exclusion chromatography (SEC) column is also a manifestation of the extended nature of attached PEG, not actual molecular weight. Using the Absorbance—$V_e/V_0$ data for both albumin and PEG-Alb in FIG. 7, we calculated the corresponding mean $V_e/V_0$ to be 2.112 and 1.588, respectively. Effective molecular weights (or size) for the albumin and PEG-Alb in the samples were determined to be about 77,670 Da and 994,300 Da, respectively, or a relative size ratio of about 12.8. The albumin estimate was greater than the known albumin size (67,000 Da) falling between its monomer and dimer weights, and this is consistent with the presence of a two Albumin absorbance peaks—a dominant monomer peak and a smaller dimer peak.

Figures 6A, 6B:
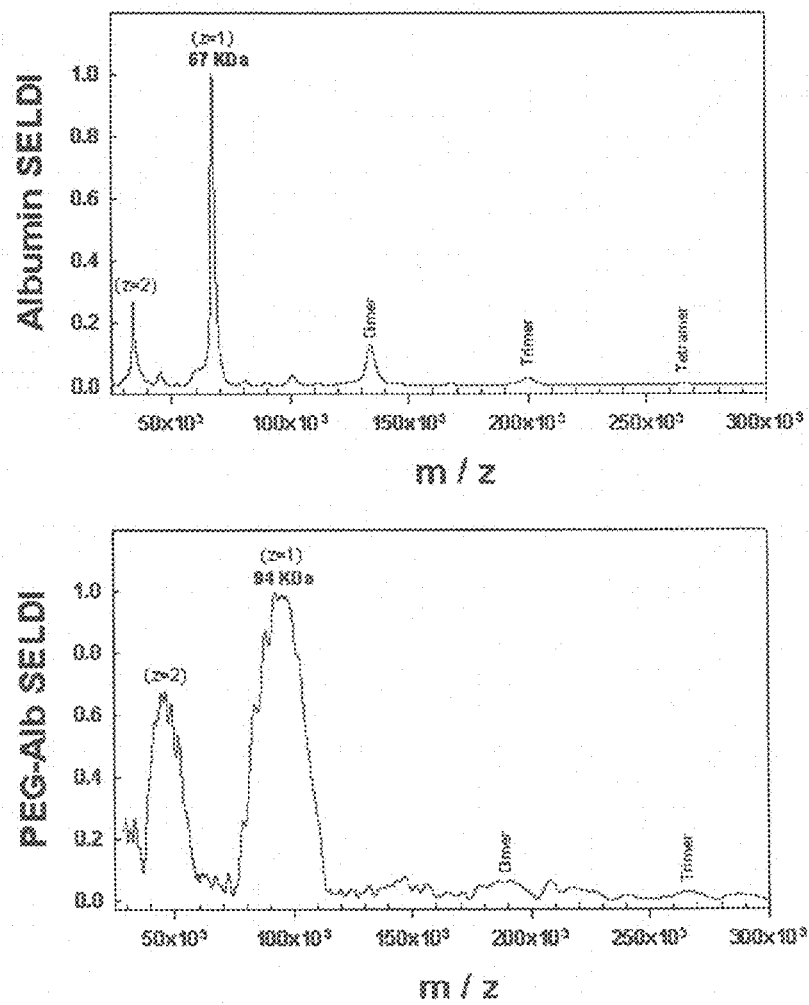
FIG. 6A shows the analysis of 16 pmoles of human albumin.
FIG. 6B shows the analysis of 15 pmoles of PEG-Alb.

To examine the extent of PEG modification by a different technique, albumin and PEGA were analyzed by SELDI-TOF mass spectrometry. Both spectra showed multiple peaks that resulted from the a) presence of monomers and multimers and, more relevantly, b) the detection of singly charged (z=1) as well as multi-charged (z≧2) species. Accounting for these effects, the dominant single-charged albumin monomer spectral peak was centered around a molecular mass of 66,880±2,800 Da (FIG. 6-A). In contrast, the corresponding PEG-Alb peak was more heterogeneous and exhibited multiple molecular mass species ranging from 77.4 to in excess of 100 kDa separated. These varying PEG-Alb components reflected the number of PEG groups attached by modifying lysyl residues per albumin molecule. Indeed, the mass separation of these PEG-Alb species was consistent with the size of the reagent (5000 $M_r$ average). The mean molecular mass of the PEG-Alb monomer predicted from SELDI-TOF was 94.000 Da±8.000 Da. This corresponded to an average of five to six PEG group attachments per albumin.

Colloid osmotic pressure ($\pi$). To evaluate the properties of PEG-Alb as an osmolyte compared to albumin, we examined their osmotic pressure ($\pi$) over a wide range of concentrations (g/dL). Both albumin and PEG-Alb, albeit differently, showed nonlinear dependence of osmotic pressure with respect to protein concentration (FIG. 7) reflecting their colligative properties, the Donnan effect, and effects arising from their molecular excluded volumes ($\Lambda$). A fit of these $\pi$-concentration data for albumin gave a value of 63,300 for the number-averaged molecular weight, a value of 15.6 for the virial coefficient B, and an $\alpha=2.0^*$. From these coefficients, the computed molecular radius of gyration (Rg) and $\Lambda$ for albumin were 3.9 nm and 2,070 nm$^3$, respectively. All these estimates are in good agreement to previously published values (34). The $\pi$—concentration data for the PEG-Alb showed greater non-ideality or increased curvature compared to albumin. The corresponding number-averaged molecular weight of PEG-Alb was 128,000 Da, B=62, $\alpha$=2.40, Rg=10.0 and $\Lambda$=33,378 nm$^3$. The latter corresponded to a 16-fold relative increase of $\Lambda$ after modification with PEG. This relative change in the extended nature of the protein with pegylation is comparable to the 13-fold increase inferred from the SEC measurements on the same proteins.

The two methods for estimating molecular weight (SELDI and colloid osmometry) provided similar estimates for albumin but not PEG-Alb. For the latter, the π-based estimate was greater than expected at 128,000 Da. Since the osmotic pressure derivation provides a number averaged molecular for all species in the solution, then an overestimate of molecular weight by this method is consistent with the presence of multimers. While not wishing to be bound by theory, it is believed this is a likely explanation of these apparent differences since the SELDI data does indeed suggest the presence of PEG-Alb multimers (FIG. 6).

Compared to saline and albumin, pre-treatment of rats with PEG-Alb prior to LPS-induced septic shock resulted in: 1) a more complete recovery in blood pressure, 2) unchanged or slightly lowered hematocrit, suggesting hemodilution as opposed to hemoconcentration that usually characterizes CL, and 3) significantly reduced lung injury.

Since rodents are fairly resistant, a relatively high dose of LPS was used in the experiments to ensure significant and sustained hypotension as a way of simulating severe human sepsis with MODS (35). The hypotension that follows LPS is characterized by a biphasic response. In the first phase, a sharp rapid drop in arterial pressure occurs within 15-25 minutes of LPS bolus infusion. This phase did not differ among the treatment groups indicating that albumin and PEG-Alb did not alter the initial effects of endotoxin relative to saline. The second phase of hypotension is caused predominantly by the action of inducible nitric oxide (iNOS), which substantially reduces plasma volume via CL (36). While iNOS mRNA or peptide was not measured, it is highly likely that iNOS was induced by the administration of a high LPS dose (20 mg/Kg)(37).

The superior effects of PEG-Alb compared to albumin or saline were manifested in this second hypotension phase of endotoxin shock. Evidence of this included the more complete blood pressure recovery and relative hemodilution. Also, minimal interstitial infiltrates and hyalinization in the lung tissues of PEG-Alb-treated rats were evident from lung histopathology while immunflourescence studies in lung tissues showed greater retention of PEG-Alb intravascularly compared to apparent albumin extravasation in the presence of CL. All these are consistent with less capillary leak and greater plasma expanding properties.

The in vitro measurements show that the substantially larger effective size and greater colloid osmotic pressures of the PEG-Alb molecule, relative to albumin renders, is less likely to extravasate in the presence of cell injury and loss of endothelial integrity. Indeed, SEC and colloid osmometry indicated a 13-16 fold increase in the extended molecular structure/excluded volume after pegylation. The improved colloidal properties of PEG-Alb resulted from increased hydrophilic properties, which are reflected by the larger hydrodynamic/gyration radius ($R_G$) and excluded volumes ($\Lambda$). In a canine model of endotoxic shock, the severity of capillary permeability was inferred by the measurment of different proteins molecular weights by electrophoresis (38). The larger molecular weights corresponded to MW of 900,000 Da and the smallest being the albumin (60,000 Da). The albumin corresponded to a radius of gyration 3.4 nm and Apopferritin dimer, the largest protein to 12.1 nm, knowing that the larger gaps are far less represented at the endothelium compared to the medium gaps (60,000-500,000 Da) (39), PEG-Alb with its 10 nm size should be retained in the vascular space in moderate to severe leak.

EXAMPLE III

The Synthesis and Purification of Maleimide-PEG Derivatives of Human Albumin were Completed Human albumin (Sigma Chemical Co. type V) at 50 mg ml-1 in 10 mM potassium phosphate (pH7.5), 150 mM NaCl, and 0.5 mM dithiothreitol was incubated for 1 hour at 30° C. Maleimide-methoxypolyethylene glycol 20,000 Mr (Shearwater Inc. cat. Number 2D2MOP01) or maleimide-methoxypolyethylene glycol 40,000 Mr (Shearwater Inc. cat number 2D2MOP01) was added to 1 mM and the reactions were incubated for 1 hour at 30° C. PEG-modified albumins were purified by ion exchange chromatography on Q-Sepharose) Pharmacia).

Figure 9:
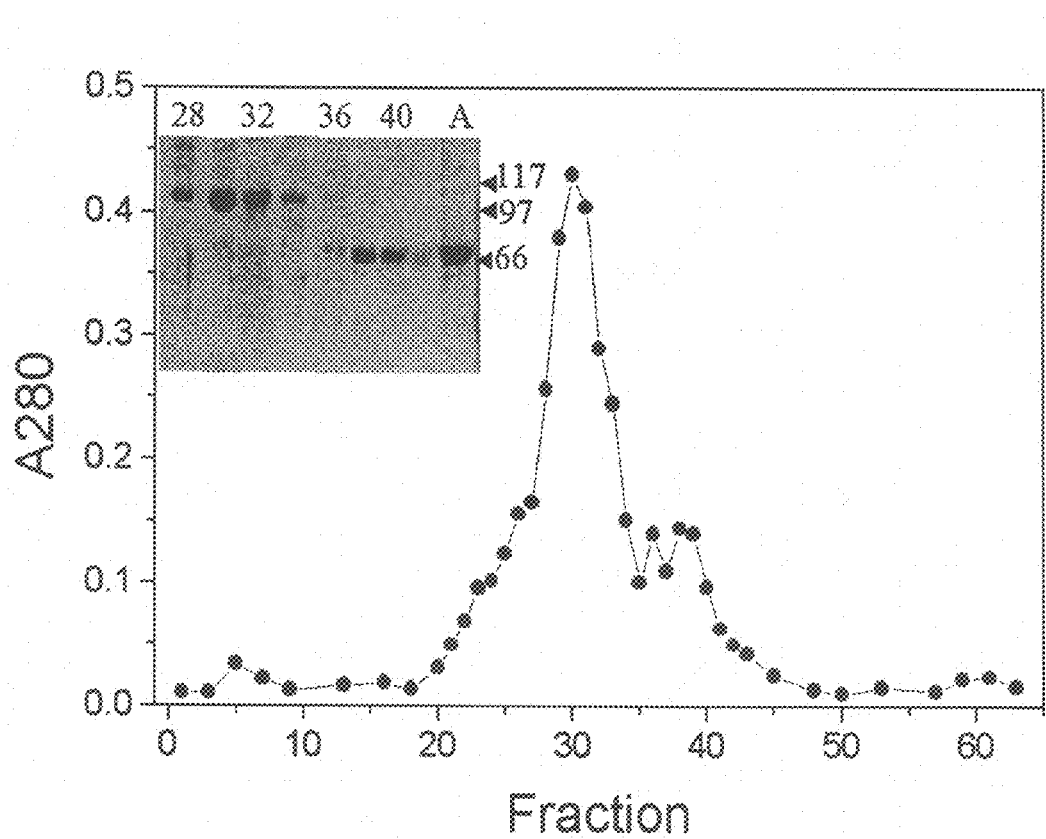
FIG. 9 shows the purification of PEG-20,000 (maleimide) modified albumin—Human albumin modified with maleimide PEG 20,000 (7 mg of protein) was applied to Q-Sepharose (1.5 cm×5 cm) equilibrated in 50 mM Tris-Cl (pH 7.5 at 25° C.).

FIG. 9 shows the purification of PEG-20,000 (maleimide) modified albumin—Human albumin modified with maleimide PEG 20,000 (7 mg of protein) was applied to Q-Sepharose (1.5 cm×5 cm) equilibrated in 50 mM Tris-Cl (pH 7.5 at 25° C.). The column was eluted at 27 ml/hr and fractions of 1.5 ml were collected. Chromatography was performed at room temperature (22° C.). The column was eluted with a gradient of NaCl from 0 to 0.5 M (100 ml total volume) starting at fraction 7. Unmodified albumin elutes between fractions 35 and 43. The inset in the Fig. shows the results of SDS gel electrophoresis (10% acrylamide gel) on alternate fractions starting with 28. The lane labeled A in the gel inset indicates unmodified albumin run as a marker and the position of molecular weight markers are indicated at the right of the gel.

Figure 10:
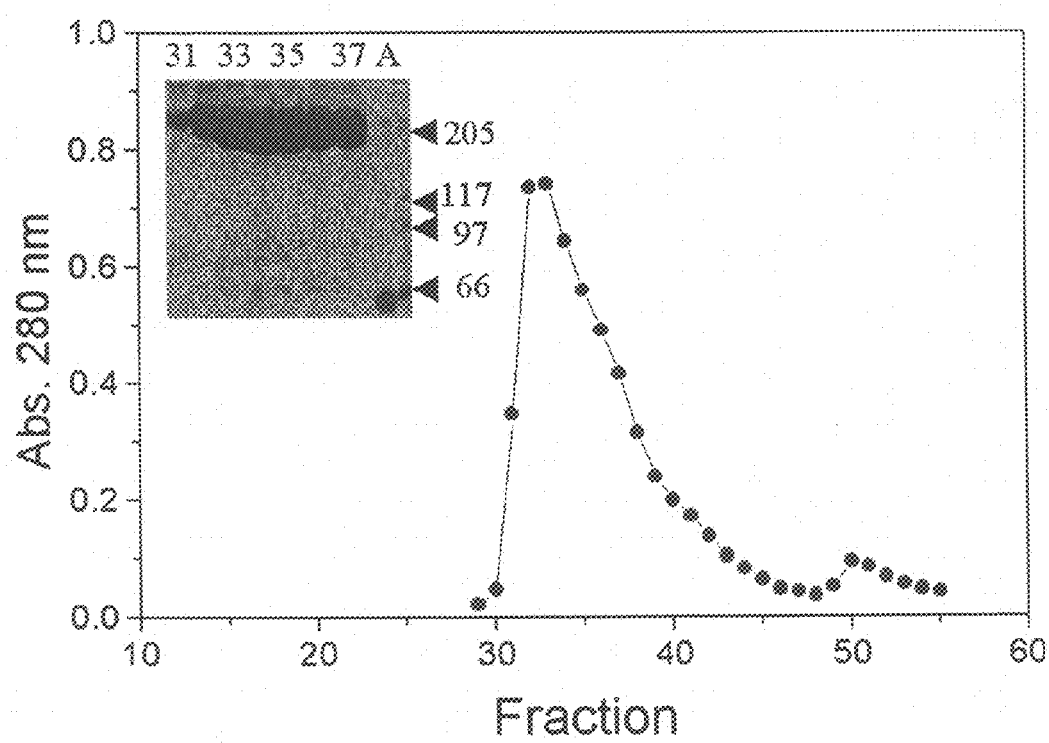
FIG. 10 shows the purification of PEG-40,000 (maleimide) modified albumin—Human albumin modified with maleimide PEG 40,000 (60 mg of protein) was applied to Q-Sepharose (1.5 cm×15 cm) equilibrated in 50 mM Tris-Cl (pH 7.5 at 25° C.

FIG. 10 shows the purification of PEG-40,000 (maleimide) modified albumin—Human albumin modified with maleimide PEG 40,000 (60 mg of protein) was applied to Q-Sepharose (1.5 cm×15 cm) equilibrated in 50 mM Tris-Cl (pH 7.5 at 25° C.). Chromatography was performed at room temperature (22° C.). The column was eluted at 27 ml/hr and fractions of 4 ml were collected. The column was eluted with a linear gradient of NaCl (250 ml total volume) from 0 to 0.3 M starting at fraction 15. Unmodified albumin elutes between fractions 45 and 55. The inset in the Fig. shows the results of SDS gel electrophoresis (10% acrylamide gel) on successive fractions starting with 31. The lane labeled A in the gel inset indicates unmodified albumin run as a marker and the position of molecular weight markers are indicated at the right of the gel.

EXAMPLE IV

Figure 11:
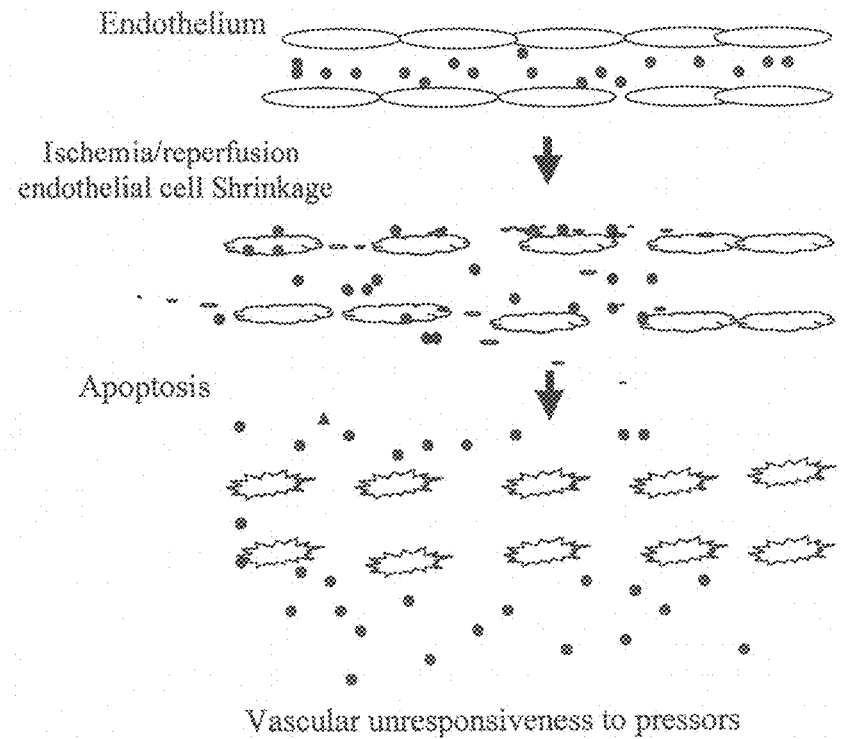
FIG. 11 is a schematic illustration if ischemia/reperfusion damage leading to apoptosis and capillary leak.
Figure 12:
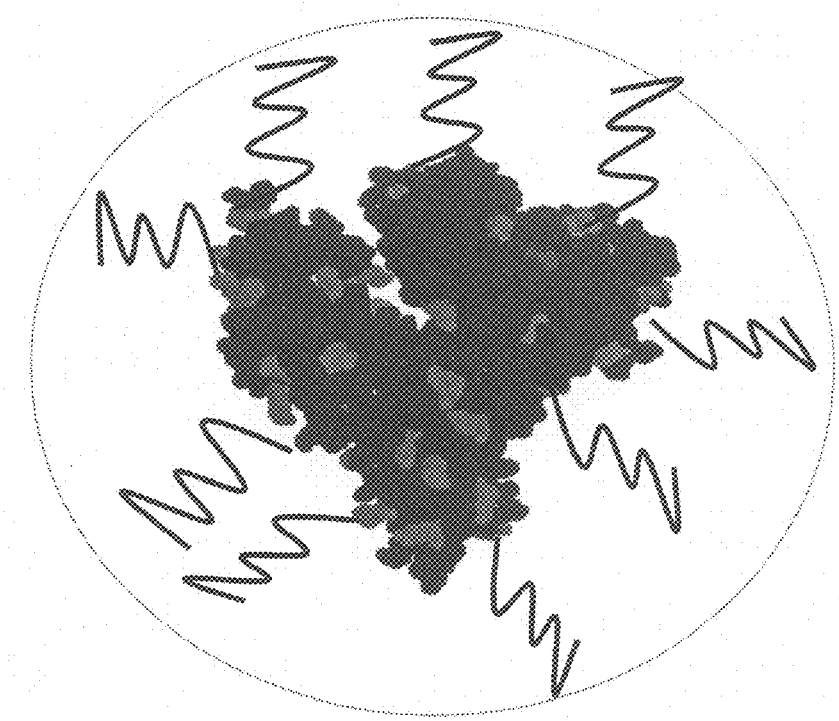
FIG. 12 shows the PEG-Alb the structure of albumin is shown with lysyl residues indicated in green, Cys 34 in red and PEG shown schematically.
Figure 13:
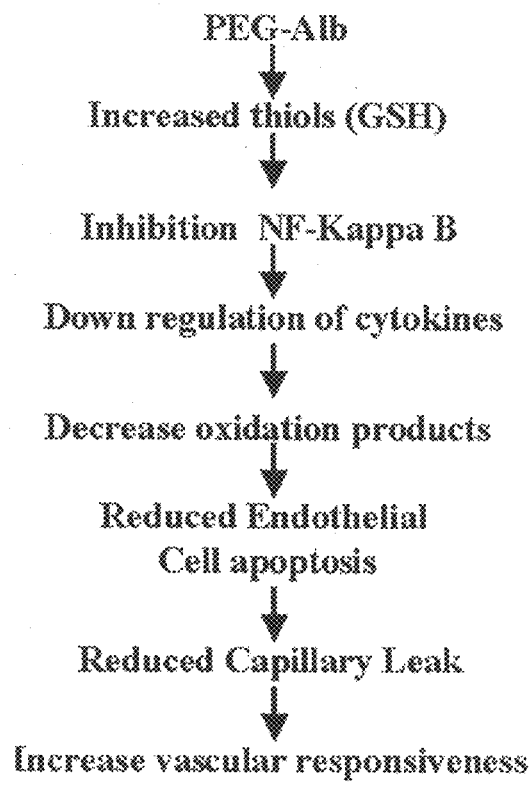
FIG. 13 shows the proposed effects of PEG-Alb on oxidation and inflammation cascades.
Figure 14:
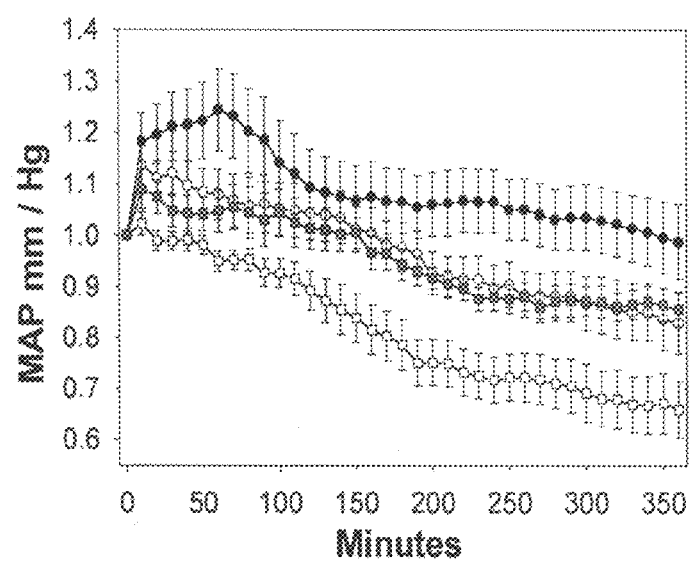
FIG. 14 shows the effect of Albumin (open circles), PEG-Alb (closed circles), saline (open squares) and PEG+albumin (closed squares) on mean arterial blood pressure (MAP) in CLP rats.

Administration of a Larger and Functionally Preserved Albumin (PEG-Alb$_{Cys-34}$) Improves Outcomes in Hemorrhagic Shock In another aspect, the present invention relates to a polyethylene glycol-modified albumin (PEG-Alb) developed by the inventors herein that is 16 times larger than albumin (42a); a representation of PEG-Alb is shown in FIG. 11. PEG-ylation, in addition to augmenting the hydrophilic properties, increases half-life (43a) of proteins in serum and decreases protein immunoginecity (44a-46a). Attaching PEG to proteins decreases the ability of the immune system (cellular or humoral) to recognize the proteins as a non-self. This stealth effect induced by PEG-ylation is secondary to the excluded volume effect resulting from the polymer attachment and to the compatibility between PEG and albumin, thus making PEG-Alb look like native albumin (47a).

Figure 31:
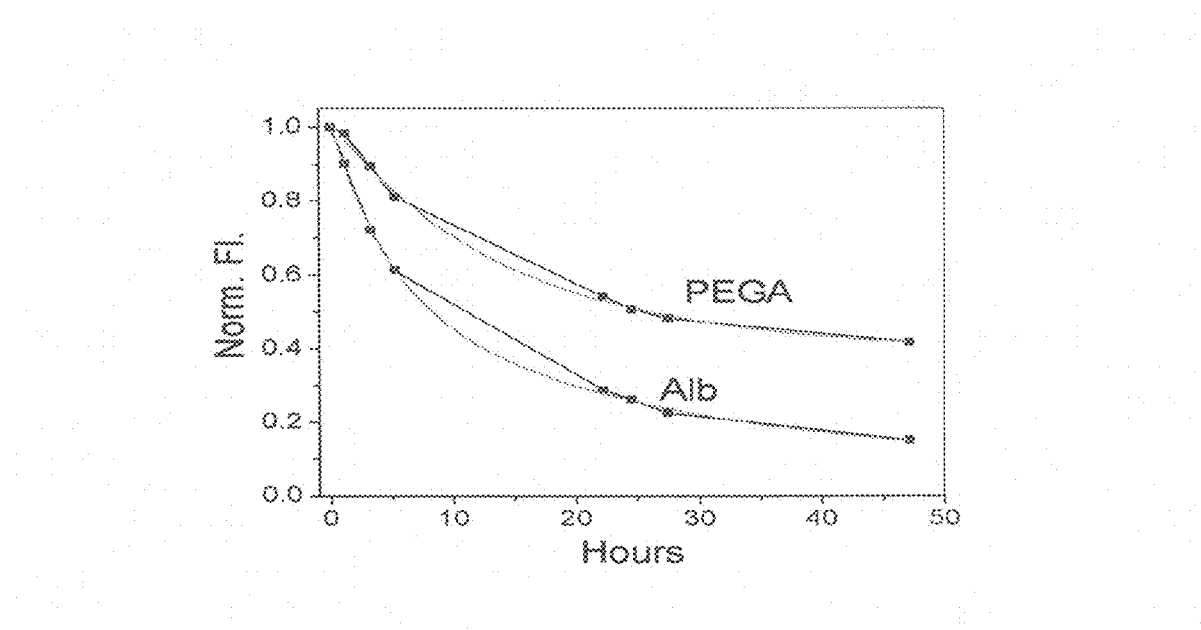
FIG. 31 shows half-life measurements of albumin and PEG-A1b in normal rats.

FIG. 31 shows half-life measurements of albumin and PEG-Alb. In normal rats. The measurements show the half-life of PEG-Alb in normal rats is at least three times that of albumin.

Unlike synthetic colloids, PEG-Alb retains important physiologic functions of albumin, including roles as an osmolyte, as an antioxidant (38a) and as a transporter of less soluble metabolites such as heme and bilirubin, features that are not associated with other crystalloids and colloids. Studies involving a variety of PEG-modified proteins demonstrate no significant toxicity (48a). The first generation (PEG-Alb$_1$) developed was more effective than albumin or saline in cecal ligation and puncture (CLP) and lipopolysaccharide (LPS) models of severe sepsis. Animals treated with PEG-Alb$_1$ exhibited more intravascular retention of the colloid, better hemodynamics, less capillary leak, and less lung injury. The increased hydrodynamic radius of PEG-Alb, reduced its extravasation and reduced end organ injury while maintaining blood pressure and organ perfusion. In addition, the biophysical characteristics of PEG-Alb$_1$ such as high colloid osmotic pressure (COP) and high viscosity allows for lowering the "transfusion trigger" point, which is defined as the hemoglobin (Hb) level below which peripheral tissues suffer from inadequate perfusion (49a).

The extravasation of albumin during capillary leak (ischemia/reperfusion) in hemorrhagic shock is critical. Specifically, this loss of albumin from the intravascular space is injurious in two major ways. First, the oncotic force of the albumin is lost, allowing for tissue edema contributing to the development of multi-organ dysfunction. Second, the antioxidant effect offered by albumin is significantly diminished, allowing for oxidant stress to continue to cause vascular injury and perpetuate the capillary leak and extravasation of more albumin. While not wishing to be held to theory, the inventors herein believe that administration of a larger (larger hydrodynamic radius) and functionally preserved (Cys-34 preserved as a thiol for its antioxidant function) albumin (PEG-Alb$_{Cys-34}$) improves outcomes in experimental hemorrhagic shock.

In one aspect, the present invention relates to PEG-Alb$_{Cys-34}$ as a resuscitation fluid for treatment of hemorrhagic shock. PEG-Alb$_{Cys-34}$, with a large effective hydrodynamic radius, will not leak from the intravascular space as is seen with unmodified albumin in capillary leak accompanying ischemia-reperfusion injury (I/R) and shock states. Retention of PEG-Alb$_{Cys-34}$ in blood vessels makes of PEG-Alb$_{Cys-34}$ more effective than unmodified albumin and other resuscitation agents, while retaining the ligand binding, antioxidant, anti-inflammatory and anti-apoptotic functions of albumin.

In another aspect, the present invention is especially useful in military applications. First, PEG-Alb maintains vascular volume as evidenced by better blood pressure recovery after resuscitation in LPS and CLP models of shock. The data also indicate that PEG-Alb is also effective in hemorrhagic shock. Second, because of its biophysical characteristics (high COP, high viscosity), PEG-Alb can lower the transfusion trigger to levels below 7 g/dl. This means that oxygen delivery to peripheral tissues is maintained at lower hemoglobin level for a longer time prior to blood transfusion. Third, PEG-Alb can be lyophilized and rehydrated so that it can be stored and reconstituted under adverse conditions.

Physiological Studies

PEG-Alb$_1$ was examined in three different models of shock, two that mimic septic shock (CLP and LPS) and one that mimics hemorrhagic shock (HS). These studies show that PEG-Alb$_{Cys-34}$ is a more effective resuscitation agent than PEG-Alb$_1$, starches and HTS.

Animal Models

Figure 15:
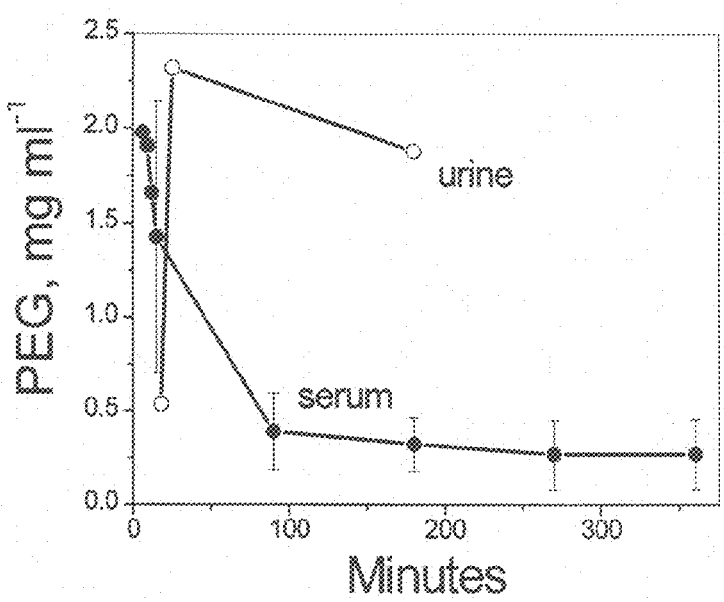
FIG. 15 shows time course of PEG appearance and elimination in serum and urine.

CLP model—Albumin modified at multiple sites with methoxy polyethylene glycol was evaluated. This material is more effective than albumin or saline in maintaining MAP. PEG-Alb$_1$ was also more effective in maintaining serum colloid osmotic pressure. A mixture of mPEG5000 and albumin was no more effective than albumin alone or saline in maintaining blood pressure, indicating that the effectiveness of PEG-Alb requires that the PEG be covalently attached to the protein. As shown in FIG. 15, blood levels of free PEG5000 drop rapidly after intravenous administration as it is passed in urine, in keeping with studies (50a) indicating that free PEG is readily excreted. When PEG-Alb$_1$ and unmodified albumin labeled with fluorescein and Texas Red respectively, were administered to CLP rats, the fluorescein label was retained within the lung vasculature while Texas Red was detected in the lung extravascular space as seen by fluorescence microscopy in FIGS. 16A and B. Both fluorescein labeled PEG-Alb$_1$ and Texas Red labeled albumin were seen only in the intravascular space of control animals. These results are consistent with the retention of PEG-Alb$_1$ in blood vessels during capillary leak due to its larger size.

Figure 17A:
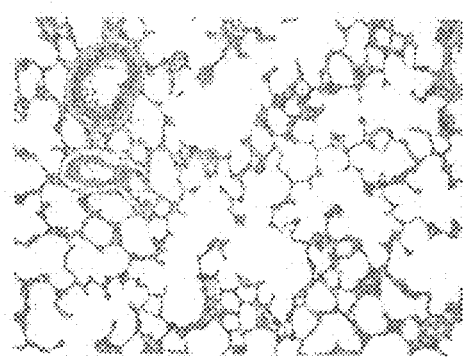
FIGS. 17A and B show 20X H&E representative lung histological sections of LPS-treated rats.
Figure 17B:
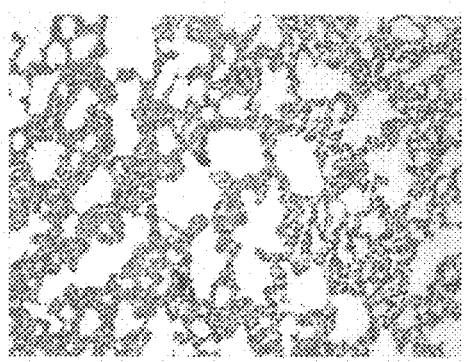
FIG. 17b, Moderate (1-2)
Figure 17C:
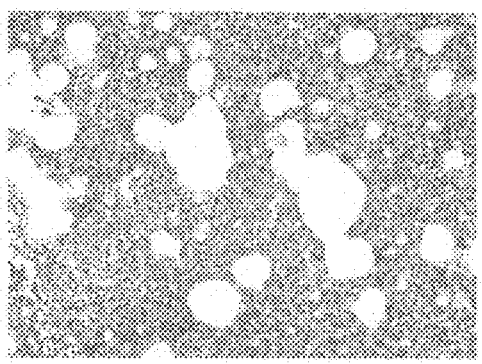
FIG. 17c Severe (3-4).

Endotoxin model—PEG-Alb$_1$ in a rat LPS model of shock was also examined. Consistent with the result in the CLP model, PEG-Alb$_1$ was more effective at maintaining MAP compared to unmodified albumin or saline. In addition, administration of PEG-Alb$_1$ before LPS treatment significantly reduced lung injury compared to saline or albumin treatment. Inflammatory histopathologic changes consistent with severe acute lung injury, including hyalinization and interstitial lymphocyte infiltrates, were detected in most rats treated with saline or albumin while these changes were less evident in rats pretreated with PEG-Alb$_1$; representative H&E sections are shown in FIG. 17 to illustrate the scoring of lung injury. Acute lung injury scores were significantly lower for PEG-Alb$_1$ (1.1±1, p<0.01) compared to saline (1.8±0.4) and albumin (2±0.63) treated animals. No significant histopathologic changes were detected in the kidney. This result indicates that PEG-Alb$_1$ maintains the integrity of the endothelium, in addition to its effects in maintaining blood pressure; however this effect was not seen when treatment of PEG-Alb$_1$ was initiated after LPS induction of shock. The absence of protective lung injury effect in the post-LPS model highlighted the importance of protecting the thiol group (Cys-34) with PEG-ylation.

Figure 18:
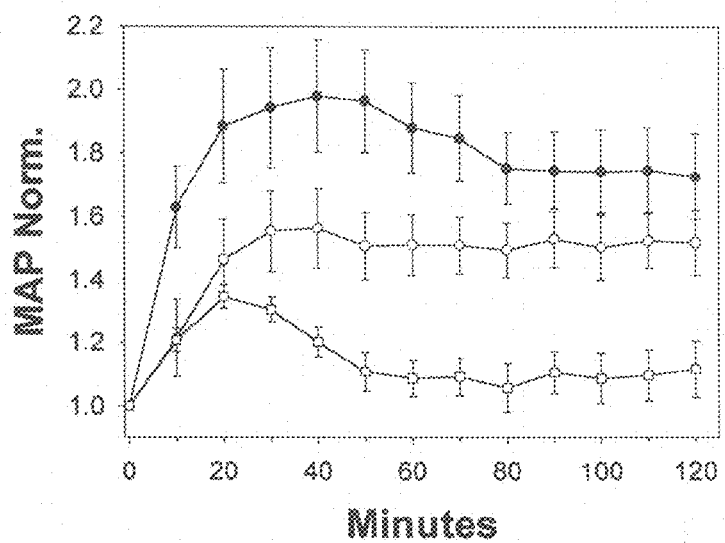
FIG. 18 shows blood pressure HS rats following treatment. Upper curve solid circles, PEG-Alb; middle curve open circles, albumin; bottom curve open squares, saline.

Hemorrhagic shock model (HS)—The effectiveness of PEG-Alb$_1$ to unmodified albumin and saline in a rat volume controlled HS model was compared. Blood (2.6 ml/100 g b.w.) was drawn over 10 minutes simulating hemorrhage; after 90 minutes, resuscitation was initiated with saline, albumin or PEG-Alb$_1$. As shown in FIG. 18, PEG-Alb$_1$ was more effective in maintaining blood pressure than albumin or saline. Groups showed similar declines in MAP 15-25 minutes after hemorrhage and similar recovery at 90 minutes. PEG-Alb treated animals exhibited significant increase in MAP at 40, 50 and 60 minutes from starting the treatment compared to saline or albumin treated animals. PEG-Alb$_1$ had a slower decline in MAP and greater plateau MAP response after treatment (p<0.01). Htc dropped after hemorrhage (table I) with a further decline following resuscitation, which was greatest for PEG-Alb$_1$ resuscitation, consistent with greater intravascular retention of PEG-Alb compared to albumin (P<0.02). COP of saline and albumin treated groups was significantly lower than PEG-Alb$_1$ group (FIG. 18a Table I). These results are consistent with the septic shock model, showing that the efficacy of PEG-Alb$_1$ is not dependent on the model of shock.

EXAMPLE IV-1

Physiological Comparison of PEG-Alb$_{Cys-34}$ to Other Resuscitation Agents

Experimental Model of Hemorrhagic Shock

PEG-Albs, including albumin in which cys 34 is retained as a thiol (PEG-Alb$_{Cys-34}$) are compared with other resuscitation agents in a well characterized rat HS model (51a-53a). a number of physiological parameters are examined that reflect the severity of different aspects of shock, including those related to lung injury, tissue perfusion (base excess, lactic acid), arterial blood gases (ABG), mean arterial pressure (MAP), heart rate (HR) and indices kidney function (creatinine). This information is used to compare PEG-Albs to established agents such as unmodified albumin, starch and hypertonic saline. PEG-Albs is also compared with different extents of PEG modification, with different size PEG, and with different protein-PEG linkages in order to optimize the performance of the PEG-Albs The experimental model mimics circumstances that occur in real life. Phase I (pre-hospital) corresponds to the initial trauma and the time required to transport an individual to location where resuscitation can be given in the field. This could correspond in practice to resuscitation given by an EMT arriving in ambulance or to resuscitation provided by a medic in a combat zone. Phase II (hospital) corresponds to treatment that would be provided after an individual has been transported to a hospital and where blood transfusion can be administered. Phase III (observation phase) is meant to correspond to the time after treatment in a hospital or a rehabilitation center.

The following protocol is used:

Phase I (Pre-hospital)—HS is initiated by volume-controlled hemorrhage (2.6 ml/100 g b.w. over 20 min (H2O). Shed blood is retained for reinfusion. At 20 min, MAP is controlled between 40-45 mm/Hg by fluid resuscitation with LR or by blood withdrawal until 80 minutes. At 80 minutes rats are randomized to treatment groups. Treatment is infused over 30 minutes until 110 minutes to simulate resuscitation that would be given in the field.

Phase II (Hospital phase)—At 110 minutes, the shed blood is infused over 10 minutes to simulate transfusion. In previous studies, using this model, some rats died early in phase II with severe hypoglycemia and metabolic acidosis; bicarbonate solution and glucose will be infused to restore MAP to >70-80 mm/Hg and glucose >150 mg/dl until H 270 minutes (53a).

Phase III (Observation phase)—Catheters are removed; anesthesia is discontinued, rats are returned to their cages with access to food and water, and observed until 72 hours. Survivors are evaluated every 24 hours using the rat overall performance score (54, 55) 1=normal, 2=moderate disability, 3=severe disability, 4=coma 5=death). Necropsies are performed on rats that die before 72 hours. Survivors are euthanized. In phases I, and II rats are anesthetized with pentobarbital (50 mg/Kg i.p) with extra doses (12.5 mg/Kg) given as needed for agitation. Incisions are treated with Bupovacaine (Marcaine 0.025%). The protocol is shown schematically in FIG. 19. Arterial blood (0.3 cc) is drawn to monitor $PO_2$, $PCO_2$, pH, $O_2$ saturation, lactate, glucose, hematocrit, base excess, and electrolytes, (Stat Profile Ultra Gas and Electrolyte Analyzer, NOVA Biomedical, Waltham, Mass.). Blood is taken at 0, 20, 45, 90, 150, and 270 minutes and replaced with RL. Blood at baseline and following euthanasia is analyzed for creatinine, PT, PTT (some synthetic colloids are associated with coagulopathy), albumin levels, viscosity (Cone-Plate Viscometer) and colloid osmotic pressure (Model 4420 colloid osmometer Wescor Inc., Logan, Utah). Blood sampling is minimized to prevent cardiac arrest resulting from profound hypotension.

Results: Data indicates that the first generation PEG-Alb (PEG-Alb$_1$) is more effective than saline or albumin.

The comparison is extended to other standard resuscitation agents. PEG-Alb with protected thiol (PEG-Alb$_{Cys-34}$) is tested. Albumin at 25% has proven to be effective in hemorrhagic shock while 5% albumin has not (40a, 56a); it is important to point out that the volume of resuscitation agent per se is significant (the same amount of albumin is given but in a more concentrated form). The reason the concentrated form is superior may be explained by the fact that threshold concentration of albumin being required to exert the antioxidant effect. Alternatively hyperosmolarity associated with the use of 25% albumin might contribute to the anti-inflammatory effect (40a). Albumin and PEG-Alb at 5% and 25%, are compared based on albumin content. Hetastrarch 6% (Hexstend$^R$) is also used in resuscitation and is compared to PEG-Albs. Hypertonic saline (7.5%) is a third resuscitation agent that is compared to PEG-Albs.

Capillary Leak Studies.

Figure 16A:
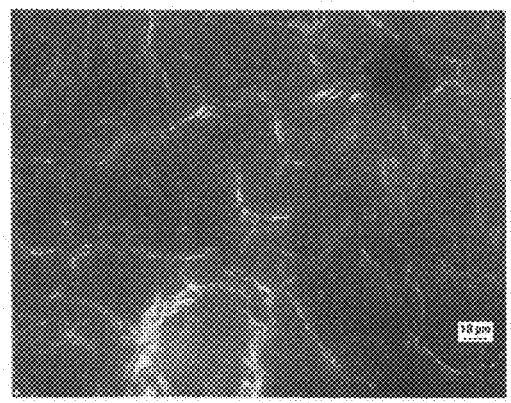
FIGS. 16A and B shows fluorescence micrographs of lung tissue from control rat (FIG. 16A) and CLP rat (FIG. 16B). Animals received fluoresein labeled PEG-Alb and Texas red labeled albumin.

While not wishing to be held to theory, the inventors here believe that PEG-Albs will be retained within blood vessels during capillary leak conditions and thus maintain the colloid-osmotic pressure of blood. We have shown that PEG-Alb$_1$, which is 16 times larger than albumin, extravasates less in capillary leak conditions associated with CLP and LPS models (42a). We determined this is also the case in hemorrhagic shock model. Using a method we developed, fluorescently labeled albumin and PEG-Alb (Texas Red, TR) and PEG-Alb (fluorescein, F) are injected into rats and a small volume of blood is taken through the tail vein for analysis at different times after injection. Preparation of the labeled albumins is described in the section of this proposal dealing with the biophysical characterization of the PEG-Alb. If albumin is lost to the extravascular space and PEG-Alb to be retained, the ratio of fluorescein to Texas Red (F/TR) will increase with time, consistent with loss of albumin and preferential retention of PEG-Alb. The excitation and emission spectra of Texas Red and fluorescein are sufficiently different that mixtures of the two dyes can be examined quantitatively in serum samples. The distribution of albumin and PEG-Alb is also examined qualitatively in frozen tissue sections of lung by fluorescence microscopy to determine if the PEG-Alb is retained within blood vessels, as observed in the models of septic shock (FIGS. 16A and B).

The labels (fluorescein albumin and Texas Red PEG-Alb) are switched to verify that the fluorophor does not alter the distribution of the protein. The bronchoalveolar lavage (BAL) is examined for the fluorescent albumin and PEG-Alb; if TR albumin leaks preferentially, one would expect the ratio of F/TR in BAL to decrease. This method is used to compare PEG-modified albumins that we have produced to determine if one is more effectively retained than others.

In an other aspect, an alternate approach is useful to study lung permeability and employs Evans Blue Dye (EBD), which is not permeable to blood vessels (57a). Rats are injected with 1% EBD solution through an internal jugular vein catheter twenty minutes before euthanasia. After allowing for complete circulation of the dye (5 minutes), blood is drawn and EBD concentration is determined in plasma. Rats are euthanized and the lungs, livers are harvested. BAL is performed on the excised lungs by instilling five milliliters of normal saline three times. The left lung lobe is tied off to prevent influx of saline to preserve this lung for the wet-to-dry weights. The lung that was not infused with saline is taken for weighing and is put in a vacuum oven for drying and subsequently measure the wet/dry as a surrogate for extravascular fluid leak. The combined BAL fluid is centrifuged to remove cells, and the supernatant is assayed for EBD. The concentration of EBD in the BAL fluid is expressed as the percentage of that present in the plasma. That is, BAL/Plasma EBD is compared between the treatment groups along with the wet/dry of the lung tissue.

Hemodynamics

A feature of PEG-Alb$_1$ compared to saline and albumin in the septic shock models is its capacity to maintain blood pressure and prevent hemoconcentration. An important issue in the hemorrhagic shock model is how well PEG-Alb$_{Cys-34}$ performs compared to standard resuscitation agents. Rats are anesthetized with sodium pentobarbital followed by maintenance sedation as needed. An arterial catheter (Intramedic PE-50, Clay Adams) is inserted into the right carotid artery, connected to a pressure transducer, amplified and continuously monitored (sampling rate 100 Hz; MP 100, BioPac Systems Inc., Santa Barbara, Calif.) and collected on a computer. An intravenous line (G24 Protective*Plus, Johnson and Johnson/Ethicon, Arlington, Tex.) is inserted in the left jugular vein for infusion of fluids. MAP and HR in animals given various fluid resuscitation agents is monitored. In the pre-hospital phase, all the rats are subjected to similar levels of ischemia for a minimum of 60 minutes, after which they are randomized to treatment groups. The crystalloid group receives three times the volume of the colloid groups, and eight times the volume of HTS group. PEG-Albs shows superior performance in MAP starting in the initial phase (pre-hospital) based on the fact that CL can occur as early as 20 minutes after hemorrhagic shock (58a). In the Hospital phase, PEG-Alb$_{Cys-34}$ group performance is superior to the other treatment groups for the following reasons: 1) Following treatment (reperfusion), capillary leak becomes even more severe and here PEG-Alb is more retained in the vascular space; 2) In contrast to crystalloids and synthetic colloids. PEG-Alb$_{Cys-34}$ improves the sensitivity of the blood vessels to the endogenous pressors by decreasing the oxidation products (10a).

Perfusion Studies:

Hypoperfusion of vital organs during hemorrhagic shock is a primary cause of organ dysfunction. A number of physiological parameters indicative of reduced blood flow are examined in order to compare PEG-Alb to other resuscitative agents.

a. Lactic Acid—Lactic acid levels correlate with subsequent organ failure in hemorrhagic shock (59a). Increased levels of epinephrine (secondary to shock) decreases ATP by stimulating the activity of Na$^+$-K$^+$ ATPase (60a), as a result lactate production increases due to mitochondrial dysfunction and anaerobic glycolysis. Improving the perfusion in PEG-Alb treated groups is expected secondary to the following factors: 1) better maintenance of systemic blood pressure and 2) better perfusion at the microcirculation level enhanced by the biophysical characteristics of PEG-Alb (increased COP and viscosity). This increases the shear stress at the capillary level stimulating the increase in nitric oxide, which results in vasodilation and improved perfusion (49a).

b. Base Excess (BE) Fencl-Stewart (61a, 62a) method. Base deficit is defined as the amount of base required to titrate one liter of whole blood to a normal pH at normal physiologic values of PaO$_2$, PaCO$_2$, and temperature (63a). BE is obtained by multiplying the deviation in standard bicarbonate from a mean of 22.9 by a factor of 1.2 (64a). Calculation of BE assumes normal water content, electrolytes, and albumin. This is relevant since significant change in plasma albumin concentration is expected. A decrease in albumin by 1 g/dl decreases the BE by 3.7 mEq/L (61a). BE corrected for changes in sodium, chloride, and albumin in a cohort of pediatric ICU patients showed a better correlation with mortality than calculated BE, anion gap and lactate (62a). Any value $\geq -5$ mEq/L is significant. Base excess corrected for unmeasured anions (Beua) is defined by:

$$Beua = BE - (Befw + Becl + Bealb)$$

The terms in this expression are:

BEua—BE corrected for unmeasured anions.

BEfw—Base excess caused by free water effect=0.3*Na−140

BEcl—Base excess caused by changes in chloride=102−Clcor, where Clcor=CL*140/N

BEalb—Base excess caused by changes in albumin=3.4*(4.5-albumin).

c. Viscosity—During treatment of hemorrhagic shock, resuscitation using large volumes of crystalloids and colloids lowers hematocrit and blood viscosity. Historically, the use of colloids and crystalloids in the correction of blood loss was considered safe up to a level called the transfusion trigger (50% Hb lost or Hb of 7 g/dl) (65a). When the hematocrit drops below 50% of baseline, the shear stress at the capillary level will be lowered, resulting in vasoconstriction and decreased oxygen delivery to the tissues. Studies by Tsai's group and others (49a, 65a, 66a) indicate that increased viscosity helps maintain oxygen delivery to tissues prior to blood transfusion or other agents for delivery of oxygen to tissues. PEG-Alb should increase viscosity as other polymerized proteins do (67a). When PEG-Alb was given at 3 g/dl to CLP rats, serum viscosity (measured with a Cone-Plate Viscometer) was at 3 cP, a level considered necessary to maintain the oxygen delivery at that degree of hemodilution (66a). As shown in FIG. 20, viscosity is linearly dependent on the concentration of PEG-Alb while colloid osmotic pressure has nonlinear concentration dependence.

EXAMPLE IV-2

Analysis of the Effectiveness of PEG-Alb$_{Cys-34}$ in Suppressing Oxidative Stress and Systemic Inflammatory Responses In vivo studies show that "maintaining PEG-Alb$_{Cys-34}$ in the vascular space following ischemia/reperfusion injury where the oxidative stress is intense and the native albumin is leaking" results in augmenting the antioxidant capacity in the vascular space, decreasing apoptosis and controlling of inflammation.

Inflammation Studies

NF-κB is activated following hemorrhagic shock, leading to overexpression and production of cytokines such as TNF-α (68a). The activation of NF-κB during ischemia (69a) or during resuscitation (70a) is considered an important step in initiating and maintaining the exaggerated inflammatory response. Importantly, the volume in which albumin is administered appears to play a significant role in inflammation. 25% Albumin, but not 5% or R/L, decreased neutrophil sequestration in the lung and prevented lung injury following shock/resuscitation (40a). This is the basis for testing albumin preparations using the two concentrations.

a. Histology—Acute lung injury (ALI) and diffuse alveolar damage (DAD) are frequent complications after hemorrhagic shock and are frequently associated with severe inflammatory response (71a). Formalin fixed lung tissues are subjected to standard hematoxylin and eosin stain processing. Coded specimens are examined by light microscopy by a blinded pathologist, who score the acute inflammatory lung injury using a five-point system: 0, no significant histopathologic changes; 1, minimal interstitial inflammatory infiltrates; 2, mild interstitial inflammatory infiltrates with mild hyalinization; 3, moderate interstitial inflammatory infiltrates with moderate hyalinization; 4, severe interstitial inflammatory infiltrates with severe hyalinization. To ensure consistency, samples are examined twice, and the scores are averaged.

b. Myeloperoxidase in lungs—The interaction between neutrophils and different cells, especially endothelial cells, plays a critical role in organ injury after resuscitation. Myeloperoxidase activity in lung extracts is measured as a measure of neutrophil sequestration, which is related to the severity of inflammation (72a).

c. Cytokines—Following reperfusion, the local inflammatory reaction involves cytokines such as TNF-$\alpha$ (73a, 74a) in addition to neutrophil recruitment. In the same HS rat model, plasma levels of TNF-$\alpha$ and TNF-$\alpha$ mRNA in liver increased significantly 20 minutes after the end of bleeding (4a). It has been shown that high concentrations of albumin decreased the production of proinflammatory cytokines such as TNF-$\alpha$ and IL-6 (39a, 75a). TNF-$\alpha$ and IL-6 is measured in lung and liver tissue during phases II and III. Standard cytokine assays is performed also in sera at baseline and following the end of phases I, II and III according to the manufacturer's protocol (Pharmingen, San Diego, A).

d. NF-kB activation—NF-kB activation occurring in the ischemic phase or following resuscitation is tied to the dysfunctional inflammatory response in hemorrhagic shock and resuscitation. Liver NF-$\kappa$B binding activity measured by electrophoretic mobility shift assays increased in the nuclear extracts 10 minutes after the end of bleeding. Western blot studies showed that the levels of inhibitory protein I$\kappa$Ba in cytoplasmic extracts decreased at 5 minutes after the end of bleeding (4a). Proinflammatory cytokines contain NF-$\kappa$B binding sites (76a); increased NF-$\kappa$B binding to their sites results in increased cytokine expression leading to increased inflammation and tissue injury. This means that down regulation of NF-$\kappa$B is expected to reduce inflammation. It had been shown in cell culture systems that albumin increased intracellular glutathione sufficiently to prevent TNF$\alpha$-induced NF-$\kappa$B translocation (77a). NF-$\kappa$B is measured in lung and liver following phases II and III. Reduction in NF-$\kappa$B is used as an indicator of a positive resuscitation effect. Electrophoretic mobility shift assays are used to measure NF-$\kappa$B and Western blot analysis to measure I$\kappa$Ba(4).

EXAMPLE IV-3

Apoptosis and Oxidation

Ischemia-reperfusion results in disrupting endothelial integrity (78a, 79a). When pulmonary artery endothelial cells (EC) were exposed to ischemic human plasma, ten minutes later they became rounded, formed gaps and then blebbed (80a, 81a). The same morphologic changes occurred in microdermal EC culture after exposure to sera from capillary leak syndrome patients (12a). Apoptosis of EC was evidenced by morphologic criteria, plasma phosphatidylserine exposure (Annexin staining), and DNA fragmentation. Increased Bax/Bcl2 in endothelial cells was detected by immunohistochemistry. The mechanism of these effects was explored by measuring intracellular reactive oxygen species (ROS) and the results suggested that oxidative injury played a role in the mechanism of EC apoptosis (12a). Oxidative stress is a well known inducer of apoptosis (11a). In addition increased apoptosis occurs after trauma and hemorrhage (15a, 78a, 79a, 82a). Inhibition of apoptosis by caspase inhibitors attenuated I/R induced inflammation (36a, 83a, 84a). In tissues exposed to ischemia-reperfusion, antioxidants minimized the damage from this injury. Albumin is the major extracellular antioxidant in plasma. It exerts this function through the enzyme gamma glutamylcysteine dipeptide, where albumin plays a significant role in glutathione synthesis (38a). Glutathione is the main low molecular weight soluble thiol present in mammalian cells, (85a) its depletion plays a role in the induction of apoptosis (86, 87). In another study looking at how albumin exerts its antioxidant activity (40), modification of the single free thiol (cys 34) was accompanied by a 45% decrease in antioxidant activity (88a). Albumin is protected against oxidation by its capacity to increase glutathione (GSH). Conversely, reduction in GSH led to a) activation of caspase 3 and poly ADP ribose polymerase (PARP) fragmentation (89a), and b) the decrease in Bcl-2/Bax ratio. The latter ratio is a strong indicator of cell survival, particularly in defense against oxidative injury (90a, 91a). As a result, albumin, through its function as antioxidant, contributes significantly to the protective effect against apoptosis. In reference to the endothelium, albumin reduced microvascular permeability (33a, 92a, 93a) and played an essential role in preventing apoptosis of endothelial cells (36a, 84a).

EXAMPLE IV-4

The Effect of PEG-Alb$_{Cys-34}$ on Cellular Injury Following I/R in Luna and Liver Tissues a. TUNEL assay—This method uses terminal deoxynucleotidyl transferase to label DNA strand breaks with fluorescein-conjugated nucleotides (94a). Apoptosis detection kit (Boehringer, Indianapolis, Ind.) will be used. Tissue samples are examined by a blinded pathologist. B. Western blot analysis of apoptosis markers—Tissue samples are quick-frozen and stored at −80° C. until extracted for Western blot analysis. Apoptosis is detected by examining a number of proteins whose presence or modification is associated with apoptosis. Rhe expression of proapoptotic protein bax and the antiapoptotic protein bcl-2 using western blot analysis are examined. Tissue extracts for cleavage products of poly ADP-ribose polymerase (PARP) are analyzed. PARP is a substrate for caspases 3 and 7 and an accepted marker for apoptosis. Full length PARP (115 Kda) is cleaved into fragments of 85 to 90 Kda and 23 to 24 Kda resulting in inactivation of its enzymatic activity (11, 95).

b. Immunohistochemical staining for bax and caspase-3—Tissues are embedded in paraffin and cut into 5-micron thick sections for immunostaining. Sections are prepared from HS animals and control animals. A polyclonal rabbit antibody specific for active caspase-3 is used. Distribution of caspase 3 in thin sections of tissue are determined by immunostaining using a fluorescent secondary antibody. For co-localizing the endothelium, CD34 and factor VIII stains are used. Negative control sections receive identical treatment except for the primary antibody. Immunostained slides from control and treated animals are coded and read at 40× magnification by blinded readers. Two separate readings are obtained for each slide and expressed as the percentage of positive cells/mm² tissue.

c. Measurement of glutathione—Oxidative stress accompanying HS is reflected in the ratio of reduced to oxidized glutathione GSH/GSSG. Accordingly, reduced and oxidized glutathione in the lung according are measured according to the procedure described by Hissin and Hilf (96). Frozen tissues are extracted with TCA, neutralized and GSH and GSSG content in the extract are determined by reaction with o-phtaldialdehyde (OPT) and the resulting fluorescence is monitored using authentic GSH and GSSG as standards. The GSH/GSSG increases following treatment with PEG-Alb$_{Cys-34}$ compared to the other groups including PEG-Alb$_1$. This correlates with less apoptotic activity as evidenced by less PARP and decreased bax/bcl-2.

d. Measurement of malondialdehyde—Malondialdehyde (MDA) in tissue extracts is also used as a marker for oxidative stress associated with HS. Malondialdehyde (MDA) (97a) and Total Antioxidant Capacity (TAOC) (98a, 99a) in the lung and liver harvested after sacrifice is determined. MDA is assayed employing an HPLC method (94a). MDA an early marker of lipid peroxidation and, along with the TAOC, increases while the GSH/GSSG ratio is expected to decrease.

EXAMPLE IV-5

Production and Biophysical Characterization of PEG-Albs

In parallel with the examples of the in vivo efficacy of the PEG-albumin, physical studies on the modified albumins are performed to identify properties that correlate with its in vivo effectiveness in treating shock.

Methods of synthesis, product size distribution, effects of modification on protein secondary structure and conformation, the effect of PEG modification on oncotic properties of albumin and effects on the binding of physiologically relevant ligands are evaluated. The example IV-5a describes preliminary studies on the preparation and properties of PEG-Albs and the example IV-5b describes the proposed studies.

EXAMPLE IV-5a

Preliminary Biophysical Studies of PEG-Albs

1. Preparation and Size Analysis of PEG-Albs

Because the mode and extent of modification and the size of mPEG (methoxypolyethylene glycol) attached to albumin may alter its biophysical properties and in vivo properties, we have examined different methods for linking PEG to albumin and have characterized the modified proteins with respect to size, stability and osmotic properties. We examined N-hydroxysuccinimide esters (mPEG5000), cyanuric chloride (mPEG5000), and thiol selective maleimide derivatives (mPEG20000 and mPEG40000).

Figure 21:
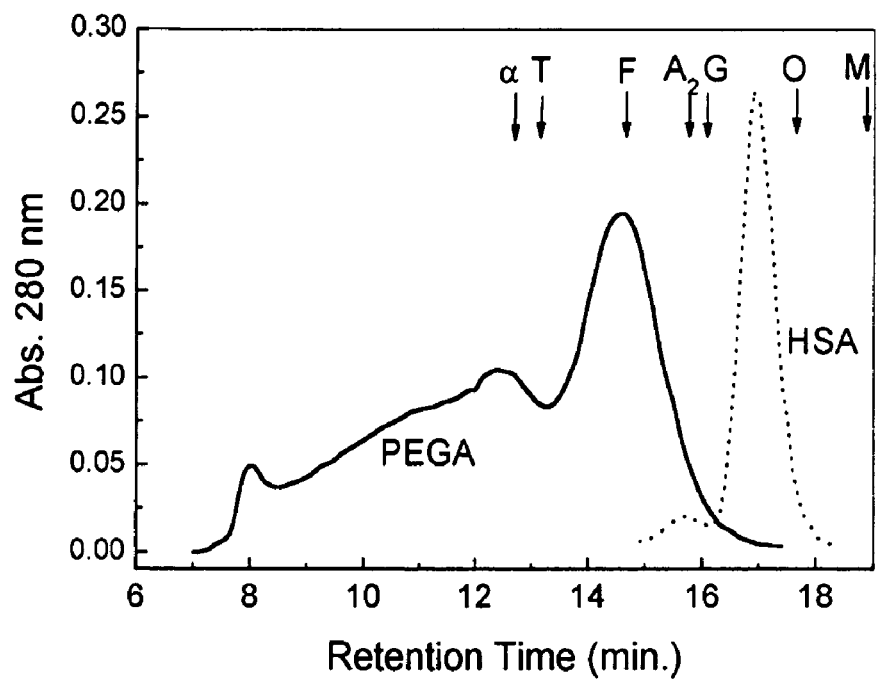
FIG. 21 shows the analysis of mPEG5000 modified albumin (PEGA, solid line) and albumin (HAS, dashed line) by Superose 6 HPLC. Standards eluting at positions indicated by arrows are: α, α-2-macroglobulin; T, thyroglobulin; F, ferritin; G, IgG; O, ovalbumin; and M, myoglobin.
Figure 22:
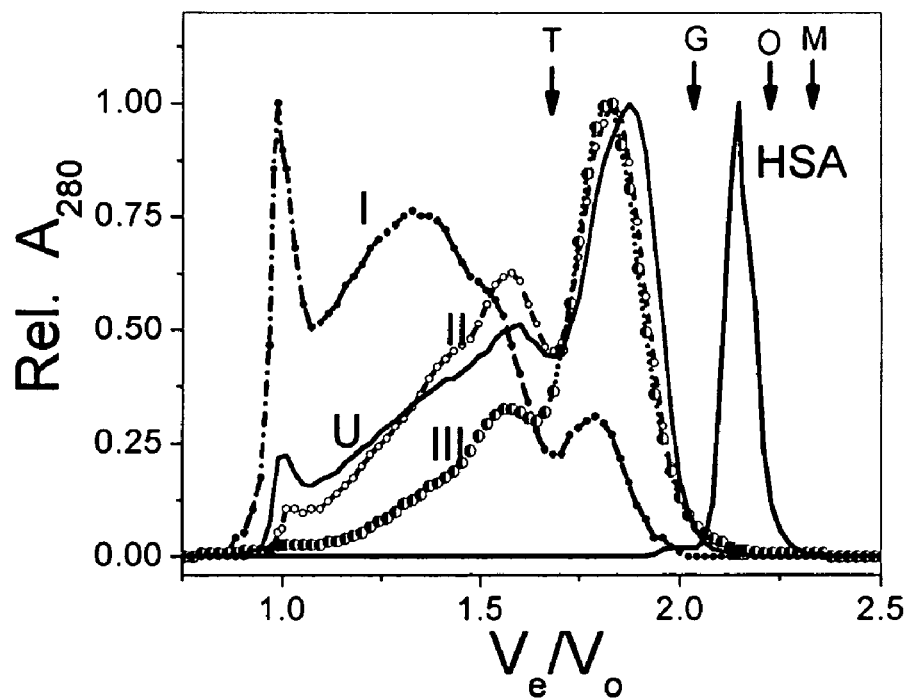
FIG. 22 shows the analysis of mPEG5000 modified albumin (PEGA) size fractions (indicated as I, II and III) and unfractionated material (indicated by U) by Superose 6 HPLC. Size standards are the same as in FIG. 11.

The cyanuric chloride (mPEG5000) derivatives have been tested in animals. These modes of modification are simple, rapid and most of the albumin is modified. Excess reagent and any unmodified albumin are removed by gel filtration or ion exchange chromatography. NHS esters and cyanuric chlorides (both selective for lysyl ε-amino groups) and maleimides (selective for cysteinyl thiols) are commercially available and react readily under mild conditions. FIG. 21 shows the results of analysis of albumin modified with cyanuric chloride mPEG5000. As expected for a reagent that modifies multiple residues, CNCl-mPEG5000 modified albumin is heterogeneous when examined by SDS gel electrophoresis ($M_{r,app}$>250,000) or by gel filtration on Superose 6 ($M_{r,app}$>450,000). The molecular weights of species seen on SDS gels are uncertain due to the extended nature of PEG and the fact that it may not bind the same mass of SDS as proteins used as standards. Albumin can be modified more extensively with this reagent by increasing the ratio of reagent to protein during modification. Product heterogeneity can be reduced by size selection by gel filtration. FIG. 22 shows the results of Superose 6 analytical gel filtration of material that was fractionated on a preparative Sephacryl S300 column (designated I, II and III) along with unmodified albumin and unfractionated material (designated U).

Figure 23:
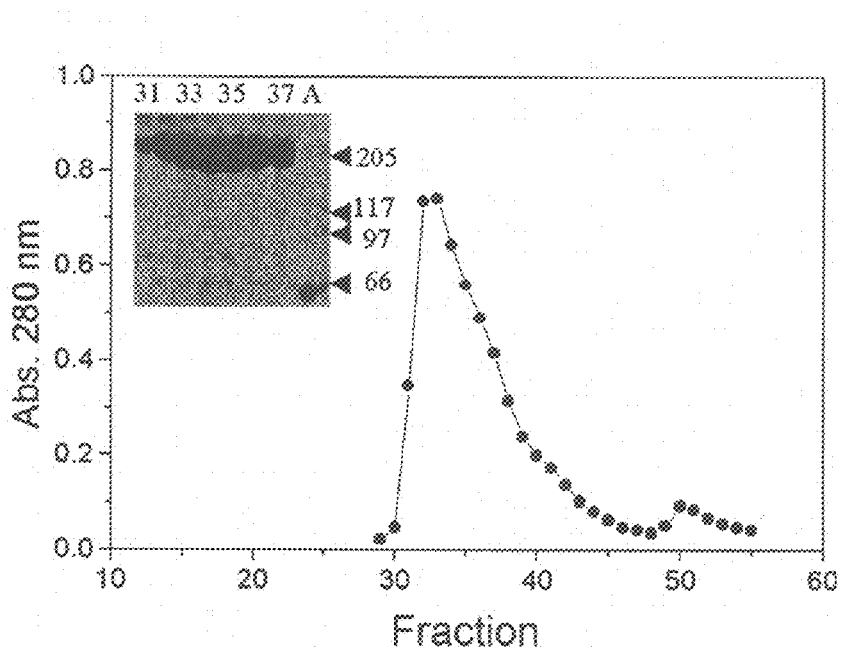
FIG. 23 shows purification of mPEG-40,000 modified albumin—HSA modified with maleimide mPEG40000 was applied to Q-Sepharose and eluted with a gradient of NaCl from 0 to 0.3 M. Inset: results of SDS gel electrophoresis on successive fractions starting with 31. Lane A in gel is unmodified albumin.
Figure 24:
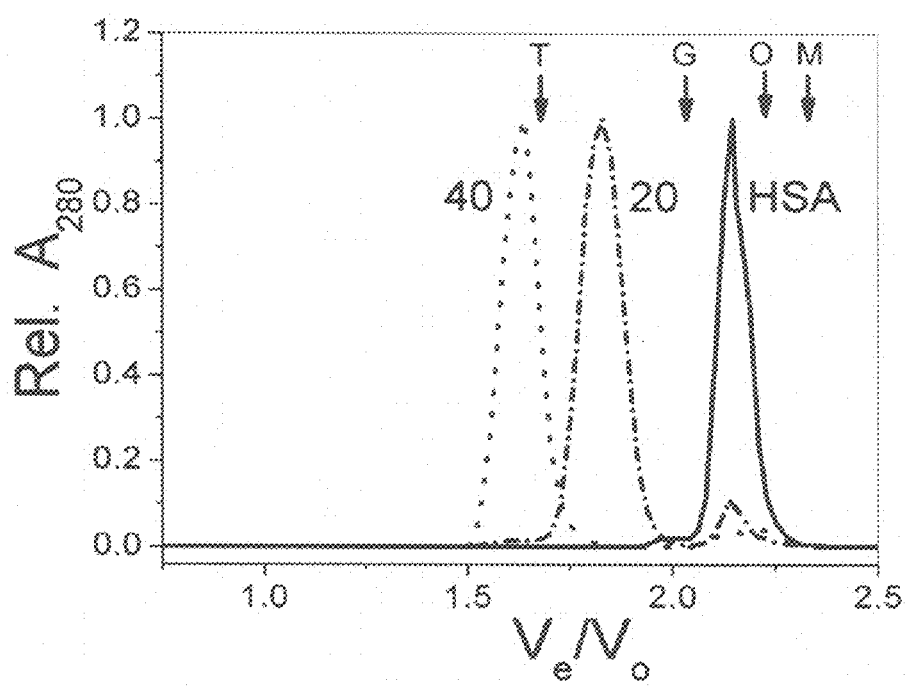
FIG. 24 shows the analysis of mPEG40000 (40) and mPEG20000 (20) modified albumin and albumin by Superose 6 HPLC. Standards are the same as in FIG. 11.

Because human albumin's single thiol (100-102) has an unusually low pKa (approximately 5.5), it is modifiable with thiol selective reagents without perturbing the disulfide structure of the protein. Acccording to one aspect of the present invention we have attached mPEGs of different sizes (a 20,000 Mr derivative and a branched 40,000 Mr derivative). Albumin is incubated with dithiothreitol and low molecular weight products linked to the albumin through cys 34 are removed by Sephadex G50 chromatography followed by modification with maleimide mPEG40000. FIG. 23 shows the results of purification of the mPEG40000 modified albumin on Q-Sepharose. Unlike the CNCl-mPEG5000 modified albumin, this material is homogenous, consistent with modification of a single cysteinyl residue. We have prepared an mPEG20000 albumin using the same approach and it also behaves as a homogenous protein. Consistent with behavior on SDS gel electrophoresis, mPEG20000 and mPEG40000 albumins elute as single symmetrical peaks when examined by gel filtration on Superose 6 as shown in FIG. 24. These modified proteins elute at sizes significantly greater than would be expected given the predicted molecular weights (87,000 for the mPEG20000 albumin and 107,000 for mPEG40000 albumin) for the singly modified species. This behavior is consistent with the extended structure of these PEGs. SELDI mass spectrometry of the PEG40000 albumin gave a single broad peak centered at 108,000 Mr indicating that it is singly modified. The behavior of these modified albumins on gel filtration shows that they have extended structures due to the extended structure of the PEG.

2. Thermodynamic Stability and Conformation of the PEG-Albs

Figure 25A:
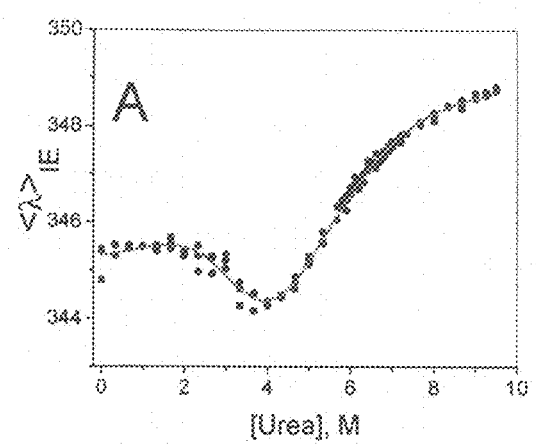
FIGS. 25A and 25B show urea unfolding of albumin (FIG. 25A), mPEG20000 albumin (FIG. 25B) and mPEG40000 albumin (FIG. 25C). Samples (0.05 mg/ml albumin in 10 mM $KP_I$ (pH 7.4), 150 mM NaCl) were incubated for 12 hours at the indicated [urea] prior to collecting emission spectra. Emission from 310 to 370 nm was measured with excitation at 295 nm and the result plotted as intensity averaged emission wavelength ($<\lambda>_{IE}$). Solid lines correspond to a fit to a three-state unfolding model.
Figure 25B:
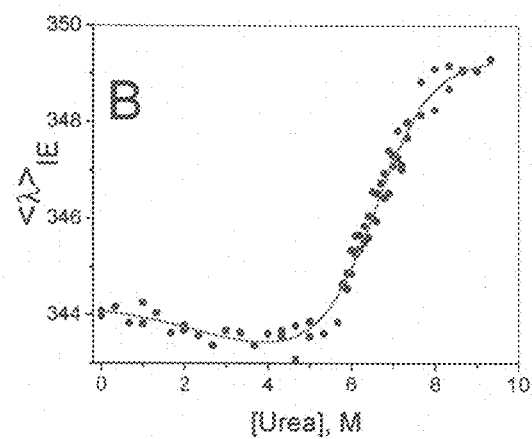
Figure 25C:
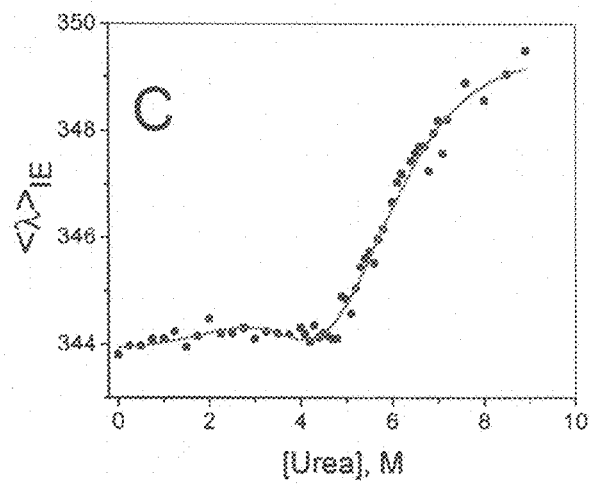

An issue in the analysis of these PEG-Albs is whether the modification alters native structure and potentially the ligand binding properties and stability of the albumin. We examined the stability of PEG-Albs by analyzing urea induced unfolding; this is a standard method for studying the thermodynamic stability of proteins which gives the free energy of unfolding and can reveal whether the protein assumes unfolded intermediates (103a-105a). The protein is incubated with increasing concentrations of denaturant and a spectroscopic signal characteristic of the native and unfolded states is examined. We used the shift in the fluorescence emission wavelength (intensity averaged emission wavelength <λ>) of the tryptophan (trp 214) as a signal since there is a significant red shift when the protein unfolds (106a). Examples of results of such studies comparing unmodified albumin (panel A), albumin modified with mPEG20000 (panel B) and albumin modified with mPEG40000 (panel C) are shown in FIG. 25. Studies by others indicate that unmodified human albumin shows a complex unfolding pathway with at least one intermediate species (106a, 107a), which our results confirm. The unfolding of the mPEG20000 and mPEG40000 modified albumin are remarkable in their similarity to unmodified albumin (FIG. 15, panel A), with the PEG-modified albumins being only slightly destabilized relative to unmodified albumin. The mPEG20000 modified albumin shows a slight blue shift at intermediate concentrations of urea suggesting the environment of the tryptophan in a partially unfolded intermediate species may be altered. With both mPEG20000 and mPEG40000 modified albumin, the midpoint of the unfolding occurs at a similar concentration to that for unmodified albumin (7M). We have performed similar unfolding studies on different size-fractionated, multiply modified mPEG5000 albumins and the results are similar to those obtained with the singly modified albumins. Overall PEG modification is not significantly destabilizing.

Figure 26:
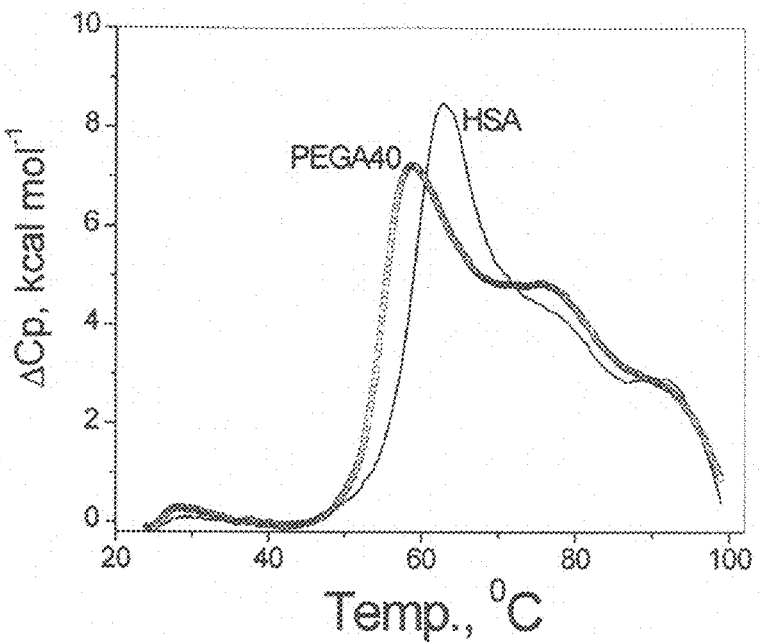
FIG. 26 shows DSC scans of PEG40-Alb (PEGA40) and unmodified albumin (HSA).

We also compared one of the PEG-Albs (PEG40-Alb) to unmodified albumin by differential scanning calorimetry (DSC). This approach gives information on the thermodynamic stability and can be employed to study the effects of ligands on conformation and stability. FIG. 26 shows the results of DSC experiments with PEG-Alb40 (PEG40) and unmodified albumin (Alb). The DSC scans are complex in part due to bound fatty acids that tend to stabilize the protein to thermally induced unfolding. The important feature is that the PEG40-Alb shows the same features as unmodified albumin. The transition temperature for the first transition seen with PEG40-Alb reflects removal of more of the fatty acids from the PEG40-Alb compared to albumin (108a-111a). The results indicate that the PEG40 modified protein retains the native structure of unmodified albumin.

To extend the studies of stability, we examined the fluorescence of the single typtophanyl residue to quenching by different agents. The tryptophan fluorescence can be used as an indicator of native structure, since subtle changes in protein conformation can alter the emission intensity and the shape of the emission spectrum (112a, 113a). Modification of albumin with mPEG5000 contributes to absorbance in the ultraviolet (between 240 nm and 280 nm), while the absorption spectra and the fluorescence emission spectra of the PEG20000 and PEG40000 modified albumins were virtually indistinguishable from unmodified albumin. Fluorescence emission spectra for the mPEG 5000, PEG20000 and PEG40000 derivatives were similar to unmodified albumin indicating that the environment of the single tryptophanyl residue has not been altered significantly.

Figure 27A:
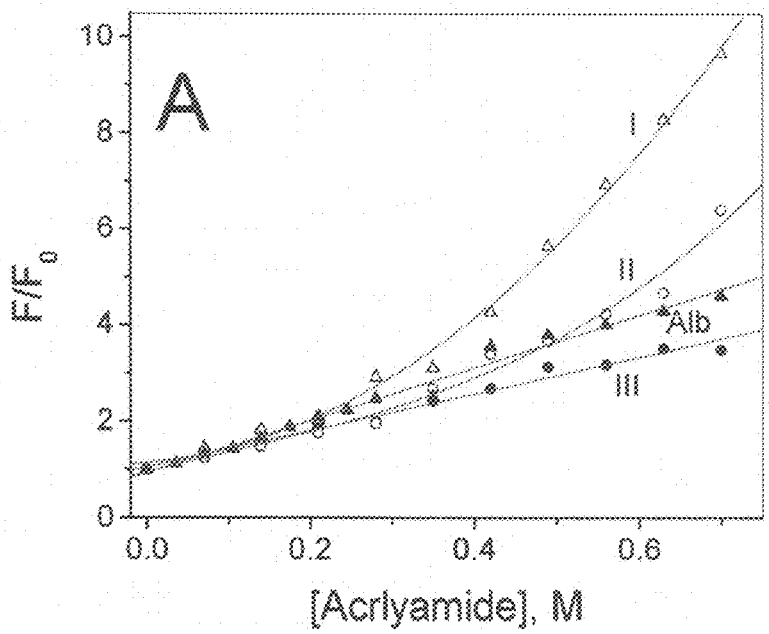
FIG. 27 shows quenching studies of PEG modified albumins. A: acrylamide quenching of albumin and size fractionated mPEG5000 albumin; B: KI quenching of albumin and size fractionated mPEG5000 albumin; C: acrylamide quenching of albumin, mPEG20000 albumin and PEG40000 albumin. Solid lines are fits of the Stern-Volmer equation with static quenching.
Figure 27B:
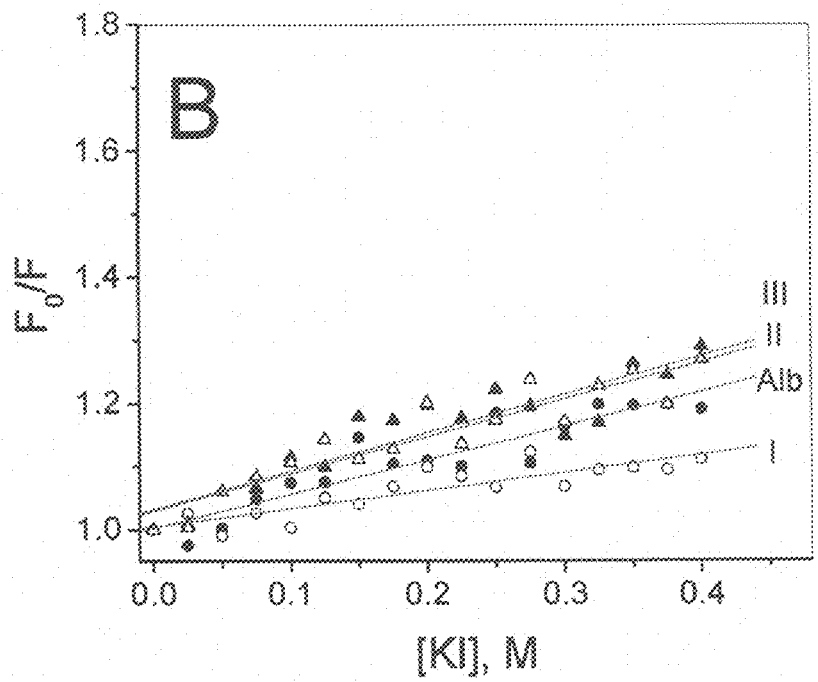
Figure 27C:
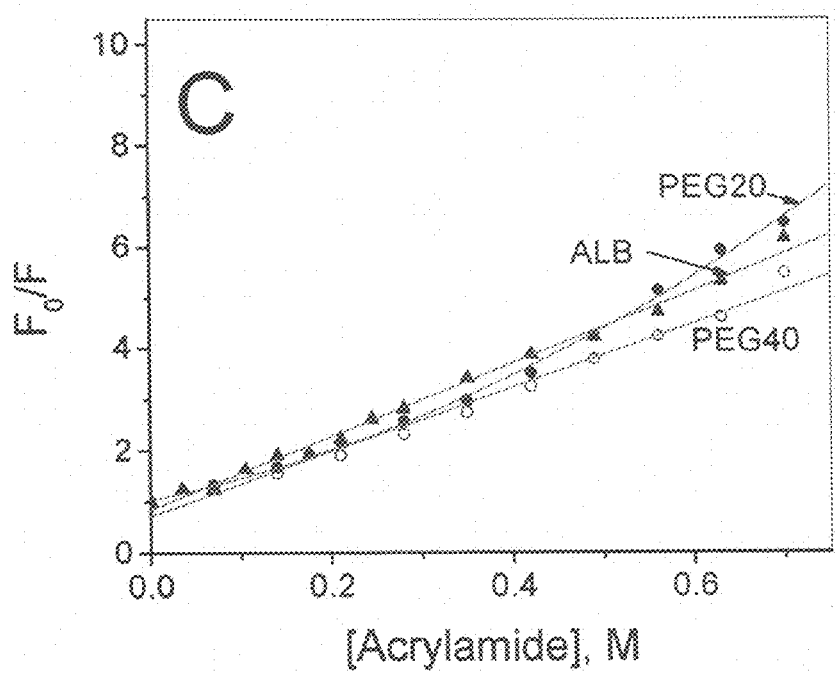

We examined the accessibility of tryptophan to the solvent by determining how readily its fluorescence could be quenched by iodide or acrylamide. FIG. 27A shows acrylamide quenching studies on mPEG5000 albumin that had been size fractionated to select for PEG-Albs with different extents of modification; the fraction designations correspond to the samples analyzed by gel filtration in FIG. 22. The least modified fraction (designated III) was similar to unmodified albumin. Fractions I and II showed greater susceptibility to quenching by acrylamide, which is manifested primarily in a static quenching component reflected in the upward curvature of the plot. This result suggests that the acrylamide, which is somewhat hydrophobic, binds to the surface of the PEG-Albs. We also examined quenching by KI, which is a charged, polar quenching agent, as shown in FIG. 27B. While the tryptophan of albumin is buried and not particularly susceptible to quenching by iodide, increasing levels of modification with PEG slightly reduced its susceptibility to quenching as seen with fractions I and II, suggesting PEG modification further shields the tryptophan from the solvent and polar solutes. In contrast, the PEG20000-Alb and PEG40000-Alb exhibited only small changes in acrylamide quenching (shown in FIG. 27C) and no change in iodide quenching (not shown). These examples show that modification of albumin at multiple sites with PEG5000 further shields the interior of the protein from the solvent and polar solutes, while modification with PEG20000 or PEG40000 do not.

3. Osmotic Properties of PEG20-Alb and PEG40-Alb

Figure 28:
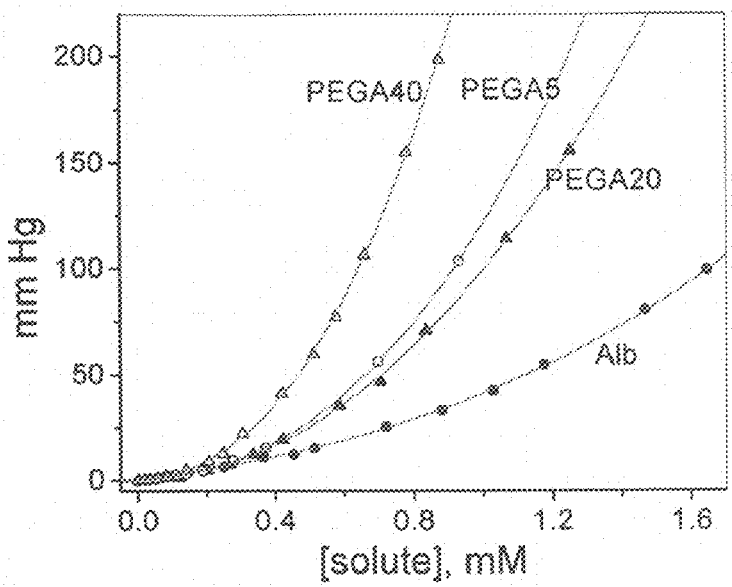
FIG. 28 shows the osmotic pressure of PEG-modified albumins—Osmotic pressure of solutions of unmodified albumin, albumin modified with mPEG20000 (PEGA20) or mPEG40000 (PEGA40) maleimides and albumin modified with unfractionated mPEG5000 (PEGA5) was measured at the indicated concentrations at 22° C. Lines are fits of a third order polynomial.

Because the osmotic properties of the modified albumins are essential for function in vivo, we examined the dependence of colloid osmotic pressure on the concentration (114a, 115a) of mPEG20000, mPEG40000, multiply modified mPEG5000 albumins and unmodified albumin as shown in FIG. 28. On a molar basis, mPEG20000-Alb, mPEG40000-Alb and mPEG5000-Alb exerted greater osmotic pressure at higher concentrations than unmodified albumin while at low concentrations the osmotic pressure was similar to that of albumin; the serum concentration of albumin is approximately 0.6 mM. The nonideal behavior seen at high concentrations with the mPEG-Albs reflects the larger excluded volume of these species and the extent of hydration. We have also examined size fractionated mPEG5000 modified albumin and the more heavily modified fractions exert greater osmotic pressure than the less heavily modified. These studies are consistent with the molecules having large excluded volumes, a property that aids in their retention within blood vessels and maintain an oncotic gradient that will reduce extravasation of fluid into the tissue interstitial space.

4. Albumins with Fluorescent Labels

We have prepared unmodified albumin and mPEG-Albs with fluorescein or Texas Red linked through cys34. These fluorescent albumin derivatives are used to examine how effectively the albumin is retained in the circulation in animals with capillary leak; disposition of these albumins can be monitored fluorometrically in body fluids or by fluorescence microscopy of tissue sections. The two fluorophors have well separated excitation and emission spectra, so samples containing a mixture of two albumins (e.g., unmodified albumin with Texas Red and PEG-albumin with fluorescein) can be examined in the same animal. When PEG is linked through cys34, we couple amine reactive versions of fluorescein or Texas Red through a lysyl $\epsilon$-amino group. Having albumin with two different fluorophors allows for the determination of how efficiently the PEG albumin with fluorescein is retained in the circulation compared to the unmodified albumin with Texas Red. These fluorescent albumins are only employed analytically for monitoring retention of unmodified versus PEG-albumin in models of shock or to monitor the in vivo half-life. We have readily detected the fluorescence of fluorescein-albumin in dilutions of serum well above the background of other fluorescent material. As necessary, measurements of intensity is corrected for the inner filter effect (112a, 113a) arising from other chromophors in serum samples; however, our studies with the fluorescent albumin indicates that any interference is negligible due to the large dilution of the serum that is required (1:1000 to 1:2000).

EXAMPLE IV-5b

Biophysical Studies

1. Preparation of PEG-Albumin

We have examined a number of reagents for linking PEG to albumin and the mPEG5000-Alb in vivo. Because the size of the PEG attached to albumin, its location and the nature of the covalent linkage results in products with significantly different stabilities, biological half-lives and ligand binding, various modes of attachment and types of mPEG (46a, 116a-120a) are examined. For the amine selective reagents that tend to modify multiple lysyl residues, specific methods are used for preparing material with a more defined size distribution so that the dependence of efficacy on size is examined. Controlling the size distribution is achieved, in part, by limiting the extent of modification in the initial reaction, by purifying the product by ion exchange or gel filtration chromatography, and by the selective modification of specific residues, as we have done with the maleimide-PEGs.

Modes of linkage—While the modes of linking the reagent to albumin that used thus far have produced a product with the desired in vivo effect, it is also within the contemplated scope of the present invention that other modes of attachment are useful to generate products with differences in stability or binding of relevant ligands. PEGs of various sizes, with different reactive groups (primarily amine and thiol selective) are available (Shearwater Corp., Huntsville Ala.); this supplier develops reagents specifically for PEGylation of biological materials. Others have emphasized the importance of attention to the quality of the mPEG reagents and biological optimization (119a). The present invention also contemplates the use of such additional method steps of modifying conditions (e.g., pH, ionic strength, temperature) and maintaining of native structure; for example, the disulfide bonding and structure of albumin may be disrupted at high pH due to protein thiol-disulfide exchange.

Figure 29:
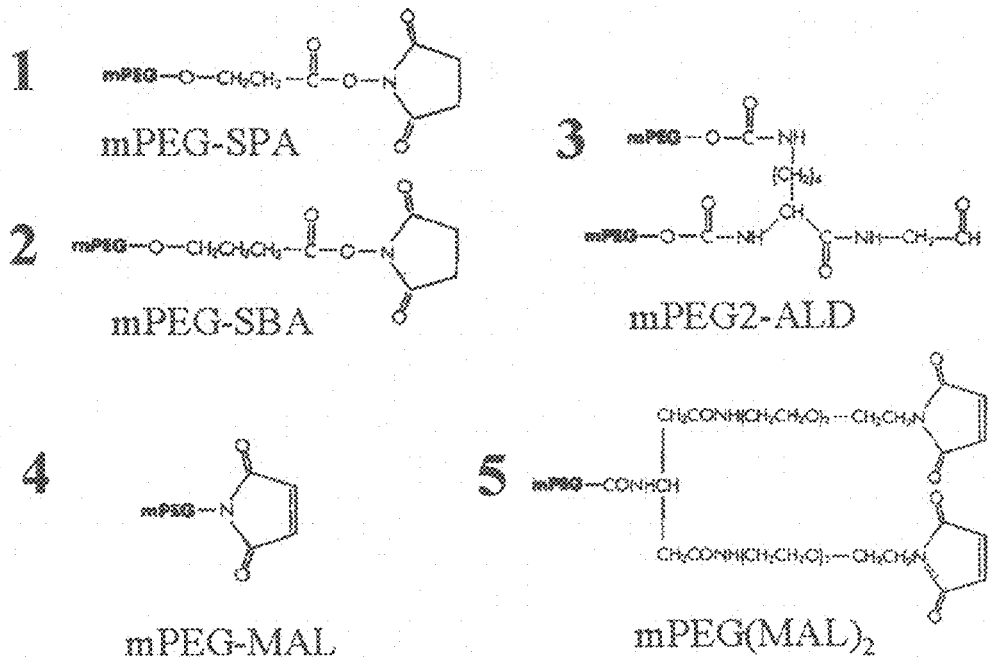
FIG. 29 shows the structures of reactive mPEG reagents.

1. Amine selective reagents—The most abundant class of nucleophiles available for modification are surface lysyl residues that are readily modified to give a highly substituted product. While mPEG-succinimidyl-succinate generates a product with an ester linkage that might be a substrate for serum esterases, other reagents such as mPEG-succinimidyl-propionate (1 in FIG. 29) and mPEG-succinimidyl-butanoate (2 in FIG. 29) are also useful to modify the same lysyl-residues, but with a more stable linkage and a longer half-life in vivo. PEG-aldehyde derivatives (e.g., 3 in FIG. 29) can be linked to lysyl residues through reduction of the resulting Schiff base with $NaCNBH_3$ (116a, 119a); this PEG reagent is more selective for lysyl residues and the modified lysyl residue retains a positive charge, which is a consideration in retaining the anion binding properties of albumin; it also does not introduce a linker. PEG can be coupled directly to a protein using tresyl chloride activation (121 a) and has been employed with albumin (122a). Linkerless methods (119a) have the advantage that they do not introduce a moiety with unknown toxicological properties. While PEG itself does is not immunogenic (123a), the element linking it to protein can be. The extent of modification is evaluated by examining the loss of reactive amines using fluorescamine (3a), qualitatively by SDS gel electrophoresis, by examining the size distribution by analytical gel filtration and by using a calorimetric assay for PEG which can be used on PEG modified proteins (124a).

Figure 16B:
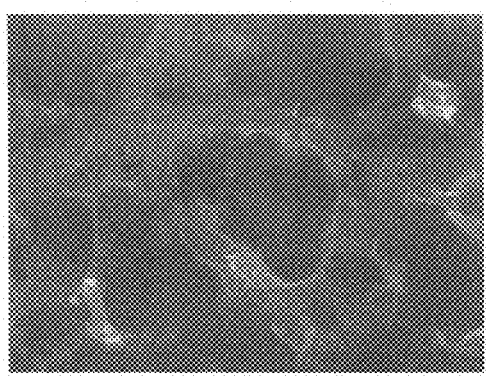

2. Thiol selective reagents—Modification through a thiol is a useful approach for human serum albumin since it has a single thiol (cys34) (100a, 101a, 125a). Human serum albumin is a mixture of protein with cys34 as a free thiol and a substantial fraction with the thiol modified with glutathione or as a disulfide dimer of two albumins. Under mild conditions, Cys34 disulfides can be reduced such that all of the cys34 is available as a free thiol without reduction of the less accessible disulfides. Cys34 is reactive with thiol selective reagents, including N-ethylmaleimide and iodoacetamide (100a, 101a, 125a). In one embodiment, albumin is modified with mPEG-maleimide derivatives (4 in FIG. 16) such that the PEG is linked to a single site on the protein. Modification at a single, unique site is less likely to perturb native structure or alter the ligand binding properties of the albumin. As indicated in the preliminary results section, we have prepared two such forms of mPEG-Alb. A potential disadvantage of thiol modification is that it may alter the antioxidant properties of the product.

PEG Derivatives of Different Sizes and Geometries

Albumins modified with different size PEGs and PEGs with branched structures are examined. Sizes available include 3,400 $M_r$, 5,000 $M_r$, 20,000 $M_r$, and 40,000 $M_r$. There are branched (3 in FIG. 29) and forked (5 in FIG. 29) versions of PEG with various chemistries for linkage to proteins (46a, 117a). Larger PEGs allow for modification at fewer sites to achieve the same effective size. The larger size distribution is particularly important for linkage through cys34 since there is only one PEG incorporated. A consideration relating to reagent size is that smaller PEG-peptides (e.g. PEG $\leq$1200 (119) are readily cleared through the kidneys, justifying analysis of multiply modified albumin. Increasing PEG chain length prolongs the half-life of the material in the circulation (117a, 126a).

Preservation of Cys 34—The activity of albumin in inhibiting apoptosis and other biological properties depend on thiols (presumably cys34). mPEG-Albs that retain cys 34 as a thiol are prepared. Albumin is treated with a slight excess of dithiothreitol followed by modification of cys 34 with 5,5'-dithiobis-2-nitrobenzoic acid. Low molecular weight products are removed by gel filtration and the protein is modified with an amine selective PEG reagent. The free thiol is regenerated by treating the protein with dithiothreitol to release the thionitrobenzoic acid (monitored spectrally at 412 nm). The mPEG albumin is purified to remove unmodified protein, excess reagent and reaction byproducts. The mPEG-albumins produced using this approach are modified at multiple sites since the reagents modify lysyl residues. However, it is also within the contemplated scope that the method can include using larger PEG reagents (e.g., PEG20000 and PEG40000) the number of residues modified can be minimized by varying reagent concentration and reaction conditions.

Size selection and analysis of PEG-albumin—The size distribution of the product is important both because the PEG-albumin must be large enough to be retained within blood vessels during capillary leak and because a product that is too extensively modified might have undesirable attributes, such as loss of ligand binding properties or toxicity. Controlling the size distribution is achieved, in part, by limiting the extent of the reaction or, in the case of modification of cys34, modification of a single residue. The modified product is purified by gel filtration or ion exchange chromatography to select for PEG-albumin of a relatively narrow size distribution. The size distribution of the preparation is determined by gel filtration using proteins of defined molecular dimensions and $M_r$ as standards and by mass spectrometry. One cannot really determine a molecular weight of the modified albumin by gel electrophoresis (127a, 128a) or by gel filtration since the PEG has an extended structure, and likely does not bind SDS the way proteins do. A more appropriate parameter is the equivalent or Stokes radius. The number average molecular weight and the effective molar volume can be obtained from the concentration dependence of colloid osmotic pressure (114a, 115a). Although the exact physical meaning of these measurements is subject to interpretation, they do provide a basis for comparing different preparations and parameters that can be correlated with in vivo effectiveness. These analyses define the extent of modification that is required for retention of PEG-albumin within blood vessels in models of shock and determine the merits of different extents of modification.

2. Effect of PEG Modification of Albumin on Protein Structure and Stability

The structure and stability of albumin are important for its physiological functions. Spectroscopic techniques are used to examine conformation and secondary structure to determine the extent to which modification of albumin with PEG alters the protein's structure and stability. Circular dichroic (CD) spectra in the near and far ultraviolet are obtained on unmodified albumin and on albumin modified with PEG. Analysis of the near ultraviolet spectra (250 to 320 nm) gives information on the extent to which modification has perturbed the microenvironment of tyrosyl and tryptophanyl residues (129a, 130a). The far ultraviolet CD spectra (180 to 250 nm) gives information on the extent to which secondary structure has been perturbed (129a, 130a). Human serum albumin is dominated by α-helix (67%) (100a-102a), and both spectra reflect this type of secondary structure. Environment of tryptophanyl residues is examined by iodide and acrylamide quenching of intrinsic tryptophan fluorescence (112a, 113a); examples of such experiments are shown in the results section. Tryptophan fluorescence, and its susceptibility to quenchers, is a sensitive probe of protein conformation. We have examined unmodified albumin and PEG modified albumin by iodide quenching and the single tryptophan is relatively inaccessible to this quencher with both proteins, consistent with PEG modification not altering its environment. In addition, the emission spectra of tryptophan for the two native proteins are essentially identical. These examples identify conditions for modification that result in PEG-albumin with minimal alterations in protein conformation and secondary structure.

Figure 30A:
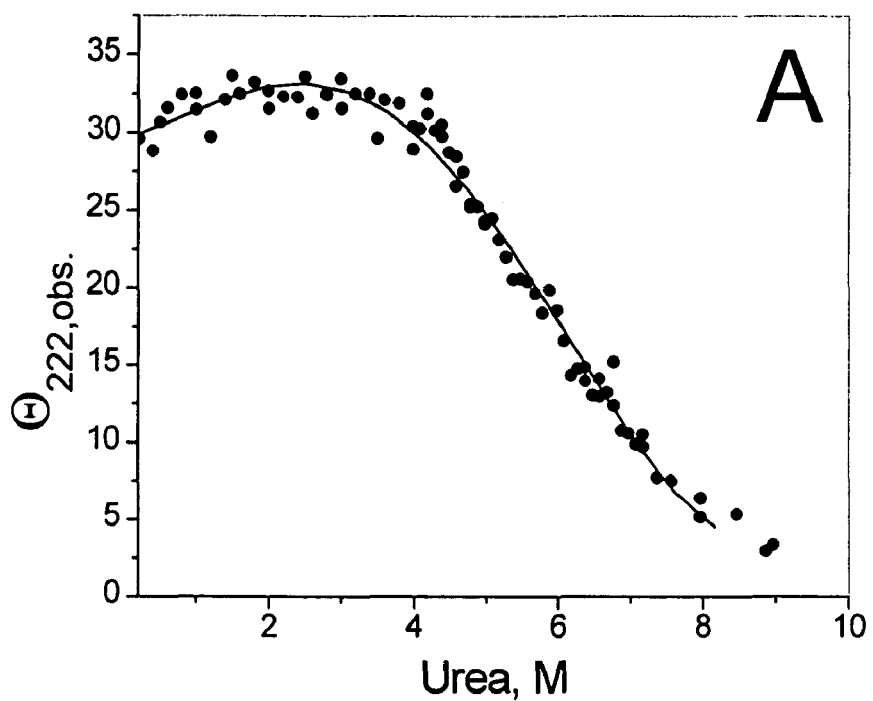
FIGS. 30A and 30B show unfolding of unmodified human albumin and mPEG5000 modified albumin.
Figure 30B:
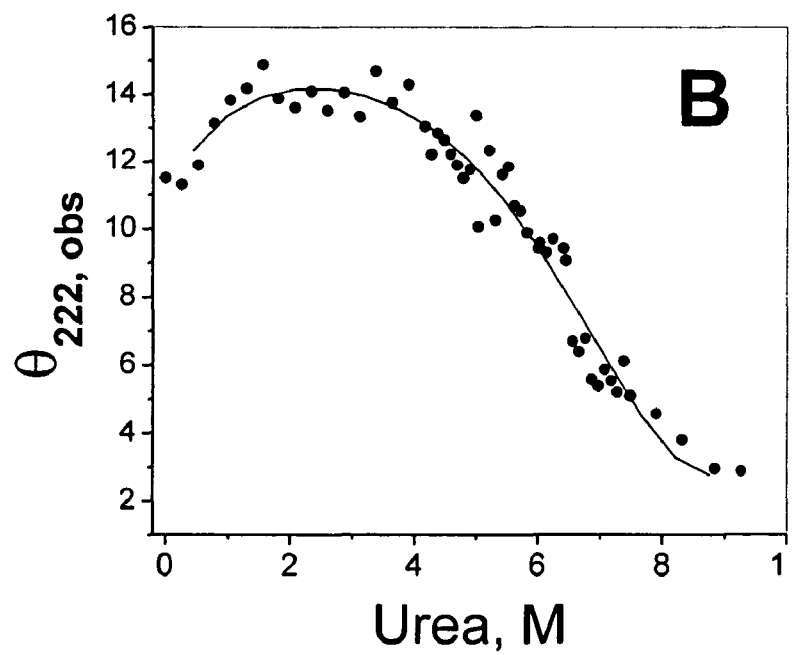

The effect of PEG modification on the stability of albumin is evaluated by examining spectroscopic signals (intrinsic tryptophan fluorescence and CD) characteristic of native structure in the presence of increasing concentrations of chaotropic solutes (guanidine-HCl or urea). Analysis of such experimental data gives the free energy of unfolding in the absence of denaturant ($\Delta G^O_{H2O}$) (103a, 105a), reflecting the thermodynamic stability of the protein. FIG. 30 shows the results of unfolding studies of unmodified serum albumin (panel A) and mPEG5000 modified albumin (panel B). The unfolding of albumin is clearly a complex, multi-state process as indicated by the lack of coincidence between the CD and tryptophan fluorescence signals, consistent with albumin being a multidomain protein (100a-102a, 131a, 132a). Unfolding monitored by CD is similar for unmodified and multiply mPEG5000 modified albumin (FIG. 30 panel B), showing that modification did not alter stability.

In another aspect, the present invention provides a method to identify conditions for modification that result in a product with the desired biological activity without altering stability. Stability of the PEG-Albs is also be examined by differential scanning calorimetry (DSC) (133a-135a). In this approach one heats a protein solution slowly and measures the excess heat capacity associated with unfolding; this approach is useful to study the effects of fatty acids and tryptophan on the stability of albumin (108a-111a). To compare both the ligand-free proteins and the ligated species, fatty acids, tryptophan and other hydrophobic ligands are removed by charcoal treatment (108a) and the effect of adding various ligands including fatty acids, heme, N-acetyltryptophan is examined. This analysis gives information about protein stability (including the enthalpy of unfolding) and the number of states involved in the unfolding process and can be used to assess the integrity of the ligand binding sites.

1. Analysis of the oncotic properties of PEG-Albumin— The concentration dependence of colloid osmotic pressure of PEG-albumins is examined to see how this property relates to in vivo effectiveness. Unmodified albumin, PEG-Albs and comparable concentrations of the corresponding unconjugated mPEGs are examined. In the simplest case, the osmotic activity of PEG-albumin is the sum of the osmotic activities of a comparable concentration of unmodified albumin and the free PEG. However, interaction of solvent and solute with proteins is not necessarily simple and results may not be a simple arithmetic sum. The present invention provides a PEG-albumin preparation with a high osmotic activity that retains overall native structure.

2. Analysis of the ligand binding properties of PEG-albumin—Albumin binds a number of important ligands, including sodium ions, bilirubin, magnesium ions, fatty acids and many drugs. Ligands bind at multiple, distinct sites on the three major domains of albumin (131a, 132a). We examined whether modification of albumin with PEG alter binding of important ligands. Representative ligands that bind to the various sites including bilirubin (137a), fatty acids (138a), heme (139a) and various drugs (125a) are examined. While binding of these ligands can be measured by spectroscopic assays (131a), the most informative and thermodynamically rigorous approach is titration calorimetry (ITC) (140a-142a). A solution of ligand is titrated into a protein solution and the heat released or absorbed during binding is measured. This approach requires no chromophor and is applicable to any ligand and acceptor. ITC experiments give the association constant, binding enthalpy, binding entropy and the stoichiometry. The only significant limitations relate to analysis of tight binding and weak ligands and ligands of limited solubility. The extent to which modification alters ligand binding is determined by examining binding isotherms for the ligand to determine the binding constant(s) and the number of binding sites. The present invention also provide examples of ligands that are useful to evaluate the functional integrity of the three binding sites in the modified albumins compared to unmodified albumin.

EXAMPLE IV-5c

Determination of the In Vivo Half-Life and Toxicological Evaluation of PEG-Albumin 1. Determination of the Half-Life of PEG-Albumin—The half-life of PEG-albumin is a consideration both in its efficacy and possible side effects. PEG modification of proteins in general (116a, 119a) and albumin specifically increases the half-life, reduces antigenicity, and reduces their susceptibility to proteolysis. PEG modification has a profound effect on the half-life of interferon α (from 6 hrs to 75 h) and its therapeutic effectiveness in treating hepatitis c (143a, 144a); with bovine albumin the change in half-life in rabbits is modest (143a). The latter result with albumin is not unexpected as it is a relatively long-lived protein (20 days in humans) even without PEG modification. As such, PEG albumin and normal albumin modified with fluorescein or Texas Red is administered; these fluorophors provide a signal for monitoring clearance from the circulation. Use of the two chromophors, one on unmodified albumin and the other on the PEG modified albumin allows for the two types of albumin to be monitored in the same animal so that the extent of preferentially retention in the circulation can be assessed. We have prepared both of these dye-albumin conjugates. The dye-albumin conjugates are administered to animals essentially as tracers and small blood samples (~100 to 200 µl) are taken through the tail vein over one to two weeks for analysis. Clearance if followed by qualitatively by examining the protein by Western blot analysis using a commercially available monoclonal antibody specific for human albumin; this approach avoids any effects that addition of a fluorophor to the protein might have. PEG-albs have dramatically different migrations on SDS gels compared to unmodified albumin and the monoclonal antibody discriminates between human and rat albumin. Using antibody specific for the human albumin, clearance is monitored quantitatively using an enzyme-linked immunoassay (ELISA); use of an antibody requires verification that that it still binds to albumin after PEG modification.

2. Analysis of the Toxicological Properties of PEG-Albumin—For PEG modified albumin to be effective in treating capillary leak syndrome it must be administered at relatively high doses compared to other PEG modified proteins that have been used therapeutically, such as interferon. An obvious difference is that a gram or more of PEG modified albumin must be given compared to micrograms of interferon. It is essential that PEG albumin not be significantly toxic at these doses. Relatively large doses of higher molecular weight PEGs (4000 to 6000 $M_r$) show little toxicity in a number of animals (rats, rabbits and dogs)(45a, 143a, 145a-147a) while some evidence suggests that the lower molecular weight PEGs (e.g., 400 $M_r$) exhibit toxicity (45a, 148a, 149a). A large fraction of blood volume of dogs (30 to 50%) can be replaced with PEGylated hemoglobin without significant toxicity over two weeks (149a). In some studies where large amounts were administered, inclusions in cells of the liver and kidney were observed, indicative of phagacytosis. In most studies of toxicity, free PEG was examined and not PEG coupled to a relatively long-lived protein. Daily intravenous doses of PEG 4000 administered to dogs at up to 90 mg/Kg for one year elicited no toxic effects (150a); there were no gross anatomical, microscopic or biochemical abnormalities. In experiments that would probably not be approved by an IRB committee if they were proposed today, PEG 6000 was administered intravenously to six human volunteers with no apparent ill effect (146a); 94 to 99% of the PEG 6000 was excreted in the urine within 12 hours. PEGs in the 1000 to 10,000 $M_r$ range are toxic in rats (147a) ($LD_{50}$ 10 to 20 gm/Kg), but only at doses that are approximately 50 to 100-fold higher than those given in the studies involving humans and dogs; the equivalent dose for a 75 Kg human extrapolated from these studies would be 0.75 to 1.5 Kg. We have seen no overt toxicity in the studies we have performed, but since all of our work has examined short term effects that are evident in less than 4 hours, toxicity arising from catabolism of PEG-albumin and release of PEG-peptides would not be observed.

Toxicological Evaluation

The most promising PEG-albumin conjugates are evaluated for toxicity by administering them at doses in a range that starts with an anticipated therapeutic dose and going to much higher doses; animals are monitored over periods of up to four weeks. Both single doses and multiple doses are tested. Data collected prior to sacrifice of the animals includes body weight, food consumption, water consumption, production of feces and urine production. Also, the animals are observed for signs of behavioral changes. Small amounts of blood are withdrawn periodically and enzyme assays are performed on serum for markers characteristic of hepatotoxicity. At the end of the experiment, the animals are sacrificed and tissues and organs are examined for macroscopic evidence of damage. A number of tissues are examined microscopically for evidence of toxicity, including liver, kidney, lung, brain, heart and skeletal muscle. Control animals that are given the vehicle are also examined in the same fashion.

While this invention has been described with emphasis upon preferred embodiments, it would be obvious to those of ordinary skill in the art that preferred embodiments may be varied. It is intended that the invention may be practiced otherwise than as specifically described herein. Accordingly, this invention includes all modifications and claims spirit and scope of the appended claims.

REFERENCES

1. Angus, D. C. Wax, R. S. 2001 Epidemiology Of Sepsis-An Update. Critical Care Medicine. 29 (7) S109-S116,
2. Baue, A. E., Durham, R, Faist, E. 1998 Systemic Inflammatory Response Syndrome (SIRS) Multiple Organ Dysfunction Syndrome (MODS), Multiple Organ Failure (MOF) Are We Winning The Battle?. Shock. 10 (2) 79-89.
3. Roberts, J. S., Bratton, S. L. 1998. Colloid volume expanders: problems, pitfalls and possibilities. Drugs. 55(5): 621-630.
4. Berger, A. 1998. Why albumin may not work (editor's commentary). BMJ. 317: 240.
5. Doweiko, J. P., and Nompleggi, D. J. 1991, Use of albumin as a volume expander, J Parenter. Enteral. Nutr. 15, 212-214.
6. 13. Emerson, T. E. 1989. Unique features of albumin: a brief review. Crit Care Med. 17(7): 690-694.
7. Margarson M. P., Soni. N. 1998. Serum Albumin: touchstone ortotem? Anaesthesia, 53:789-803.
8. McClelland. 1998. Human albumin administration in critically ill patients. BMJ. 317: 882-886.
9. Wilkes, M., and Navickis, R. J. 2001. Patient survival after human albumin administration. Ann Intern Med. 135:149-164
10. Cochrane Injuries Group Albumin Reviewers. 1998. Human albumin administration in critically ill patients: systematic review of randomized controlled trials. BMJ. 317: 235-40.
11. Delgado, C., Francis, G. E. and Fisher, D. 1992. The uses and properties of PEG-linked proteins. Critical Reviews in Therapeutic Drug Carrier Systems. 9(3,4): 249-304.
12. Abuchowski, A., van Es, T., Palozuk, N. C., and Davis, F. 1977, Alteration of immunological properties of bovine serum albumin by covalent attachment of polyethylene glycol. J Biol Chen. 252(11): 3578-3581.
13. Kozlowski A; Charles S A; Harris J M, 2001, Development of pegylated interferons for the treatment of chronic hepatitis C. BioDrugs 15, 419-29
14. Conover, C., Malatesta, P., Lejeune, Chang, C. L., and Shorr, R. G. L. 1996. The effects of hemodilution with polyethylene glycol bovine hemoglobin (Peg-Hb) in a conscious porcine model. J Inves Med. 44(5): 238-246.
15. Conover, C. D., Lejuene, L., Shum, K., Gilbert, C., and Shorr, R. G. 1997. Physiological effect of polyethylene glycol conjugation of stroma-free bovine hemoglobin in the conscious dog after partial exchange transfusion. Artif Organs. 21(5): 369-78.
16. Conover, C. D., Linberg, R., Lejuene, L., Nagy, M., and Shum, K. L. 1999. PEG-hemoglobin as a resuscitation solution in the treatment of hypovolemic shock in the anesthetized rat. Artif Organs. 23(12):1088-1098.
17. Yeh, T., Parmar, J. M., Rebeyka, I. M., Lofland, G. K., Allen, E. L., Dignan, R. J., et al. 1992. Limiting edema in 18. Axon, R. N., Baird, M. S., Lang, J. D., Brix, A. E., Nielson, V. G., 1998. Pentalyte Decreases Lung Injury After Aortic Occlusion-Reperfusion. Am J Respir. Crit. Care Med. 157-1982-1990
19. Heneka M. T. Loschmann, P. A., Osswald H. 1997. Polymerized Hemoglobin Restores Cardiovascular and Kidney Function in Endotoxin—induced Shock in the Rat. J. Clin. Invest. 99; 47-54.
20. Zoellner, H., Hofler, M., Beckmann, R., Hufnagl, Vanyek, E., Blelek E, et al. 1996. Serum albumin is a specific inhibitor of apoptosis in human endothelial cells. *J Cell Science.* 109: 2571-2580.
21. Cantin, A. M., Paquette, B., Richter, M., and Larivee, P. 2000. Albumin-mediated regulation of cellular glutathione and nuclear factor Kappa B activation. *Am J Respir Crit Care Med,* 162: 1539-1546.
22. Assaly, R., Olson, D., Hammersely, J., Fan, P. S., Liu J., Shapiro J., Kahaleh, B., 2001. Initial Evidence of Endothelial Cell Apoptosis as a Mechanism of Systemic Capillary Leak Syndrome. Chest: 120:1301-1308.
23. Quinlan, G. J., Margarson, M. P., Mumby, S., Evans, T. W., Gutteridge, J. M. C. 1998. Administration of albumin to patients with sepsis syndrome: a possible beneficial role in plasma thiol repletion. *Clin Sci.* 95: 459465.
24. Filep, J. G., Delalandre, A., Beauchamp, M. 1997. Dual role for nitric oxide in the regulation of plasma volume and albumin escape during endotoxin shock in conscious rats. *Circ Res.* 81: 840-847. problems and solutions. Biomaterials 22,405-417.
25. Vandegriff, K. D., McCarthy, M., Rohifs, R. J., and Winslow, R. M. (1997) Colloid osmotic properties of modified hemoglobins: chemically cross-linked versus polyethylene glycol surface-conjugated. Biophys. Chem. 69, 23-30.
26. Laemmli, U. K. 1970. Cleavage of structural proteins during the assembly of the head of bacteriophage T4. *Nature.* 227:6980-6985.
27. Peters, T. 1996, All About Albumin, Academic Press,
28. Tanford, C., 1961, Physical Chemistry of Macromolecules, John Wiley and Sons, New York, p 217.
29. Johnson, D. E. 1998, Applied Multivariate Methods for Data Analysis. Duxbury Press. Page 319-121.
30. Bullock, J., 1996, Characterization of Polyethylene glycol—Modified Superoxide Dismutase: Comparison of Capillary Electrophoresis and Matrix-Assisted Laser Desorption/Ionization Mass Spectrometry. Anal. Chem. 68, 3258-3264.
31. Veronese F. M. 2001. Peptide and protein PEGylation: a review of problems and solutions. Biomaterials. 22. 405-417.
32. Nathan, C. 1997. Inducible Nitric Oxide Synthase: What Difference Does It Make? J. Clin. Invest. 100(10):2417-2423.
33. Hubbard, J. D., Janssen, H. F. 1988. Increased microvascular permeability in canine endotoxic shock: protective effects of ibuprofen. *Circ Shock.* 26: 169-183.
34. Taylor, A E, Granger D N, :1984. Exchange of macromolecules across the microcirculation. Handbook of Physiology. The Cardiovascular System IV, Am. Physiol. Soc, 4(1): 11,467-520.

ADDITIONAL REFERENCES

1a. Baker C C. Hemorrhagic shock and interleukin-2 production. Crit Care Med 1988; 16(4): 358-9.
2a. Bellamy R F, Maningas P A, Wenger B A. Current shock models and clinical correlations. Ann Emerg Med 1986; 15(12): 1392-5.
3a. Heckbert S R, Vedder N B, Hoffman W, Winn R K, Hudson L D, Jurkovich G J, et al. Outcome after hemorrhagic shock in trauma patients. J Trauma 1998; 45(3): 545-9.
4a. Altavilla D, Saitta A, Guarini S, Galeano M, Squadrito G, Santamaria L B, et al. Nuclear factor-kappa as a target of cyclosporine in acute hypovolemic hemorrhagic shock. Cardiovasc Res 2001; 52(1): 143-52.
5a. Abraham E, Bursten S, Shenkar R, Allbee J, Tuder R, Woodson P, et al. Phosphatidic acid signaling mediates lung cytokine expression and lung inflammatory injury after hemorrhage in mice. J Exp Med 1995; 181(2): 569-75.
6a. Abraham E, Jesmok G, Tuder R, Allbee J, Chang Y H. Contribution of tumor necrosis factor-alpha to pulmonary cytokine expression and lung injury after hemorrhage and resuscitation. Crit Care Med 1995; 23(6): 1319-26.
7a. Bunnel I L, Greene D G, Kunz W W. Influence of tetraethylammonium chloride on the circulatory responses to the Valsalva maneuver. J. Appl. Physiol. 1951; 4(5): 345-50.
8a. Goode H F, Webster N R, Howdle P D, Leek J P, Lodge J P, Sadek S A, et al. Reperfusion injury, antioxidants and hemodynamics during orthotopic liver transplantation. Hepatology 1994; 19(2): 354-9.
9a. Rhee P, Wang D, Ruff P, Austin B, DeBraux S, Wolcott K, et al. Human neutrophil activation and increased adhesion by various resuscitation fluids. Crit Care Med 2000; 28(1): 74-8.
10a. Szabo C. The pathophysiological role of peroxynitrite in shock, inflammation, and ischemia-reperfusion injury. Shock 1996; 6(2): 79-88.
11a. Thompson C B. Apoptosis in the pathogenesis and treatment of disease. Science 1995; 267(5203): 1456-62.
12a. Assaly R, Olson D, Hammersley J, Fan P S, Liu J, Shapiro J I, et al. Initial evidence of endothelial cell apoptosis as a mechanism of systemic capillary leak syndrome. Chest 2001; 120(4): 1301-8.
13a. Pieber D, Horina G, Sandner-Kiesling A, Pieber T R, Heinemann A. Pressor and mesenteric arterial hyporesponsiveness to angiotensin II is an early event in hemorrhagic hypotension in anaesthetized rats. Cardiovasc Res 1999; 44(1): 166-75.
14a. Tabrizchi R. Cardiovascular effects of noradrenaline in hypovolemic haemorrhage: role of inducible nitric oxide synthase. Eur J Pharmacol 1998; 361(2-3): 227-34.
15a. Deb S, Sun L, Martin B, Talens E, Burris D, Kaufmann C, et al. Lactated ringer's solution and hetastarch but not plasma resuscitation after rat hemorrhagic shock is associated with immediate lung apoptosis by the up-regulation of the Bax protein. J Trauma 2000; 49(1): 47-53; discussion 53-5.
16a. Deb S, Martin B, Sun L, Ruff P, Burris D, Rich N, et al. Resuscitation with lactated Ringer's solution in rats with hemorrhagic shock induces immediate apoptosis. J Trauma 1999; 46(4): 582-8; discussion 588-9.
17a. Selby J B, Mathis J E, Berry C F, Hagedorn F N, Illner H P, Shires G T. Effects of isotonic saline solution resuscitation on blood coagulation in uncontrolled hemorrhage. Surgery 1996; 119(5): 528-33.
18a. Scheingraber S, Rehm M, Sehmisch C, Finsterer U. Rapid saline infusion produces hyperchloremic acidosis in patients undergoing gynecologic surgery. Anesthesiology 1999; 90(5): 1265-70.

19a. Laxenaire M C. [What is the real risk of drug hypersensitivity in anesthesia? Incidence. Clinical aspects. Morbidity-mortality. Substances responsible]. Ann Fr Anesth Reanim 2002; 21 Suppl 1:38s-54s.

20a. Koustova E, Rhee P, Hancock T, Chen H, Inocencio R, Jaskille A, et al. Ketone and pyruvate Ringer's solutions decrease pulmonary apoptosis in a rat model of severe hemorrhagic shock and resuscitation. Surgery 2003; 134 (2): 267-74.

21a. Tawadrous Z S, Delude R L, Fink M P. Resuscitation from hemorrhagic shock with Ringer's ethyl pyruvate solution improves survival and ameliorates intestinal mucosal hyperpermeability in rats. Shock2002; 17(6): 473-7.

22a. Berger A. Why albumin may not work. Bmj 1998; 31.7 (7153): 240.

23a. Roberts J S, Bratton S L. Colloid volume expanders. Problems, pitfalls and possibilities. Drugs 1998; 55(5): 621-30.

24a. Yeh T, Jr., Parmar J M, Rebeyka I M, Lofland G K, Allen E L, Dignan R J, et al. Limiting edema in neonatal cardiopulmonary bypass with narrow-range molecular weight hydroxyethyl starch. J Thorac Cardiovasc Surg 1992; 104 (3): 659-65.

25a. Rhee P, Koustova E, Alam H B. Searching for the optimal resuscitation method: recommendations for the initial fluid resuscitation of combat casualties. J Trauma 2003; 54(5 Suppl): S52-62.

26a. Fan J, Marshall J C, Jimenez M, Shek P N, Zagorski J, Rotstein O D. Hemorrhagic shock primes for increased expression of cytokine-induced neutrophil chemoattractant in the lung: role in pulmonary inflammation following lipopolysaccharide. J Immunol 1998; 161(1): 440-7.

27a. Emerson T E, Jr. Unique features of albumin: a brief review. Crit Care Med 1989; 17(7): 690-4.

28a. Margarson M P, Soni N. Serum albumin: touchstone or totem? Anaesthesia 1998; 53(8): 789-803.

29a. Wilkes M M, Navickis R J, Sibbald W J. Albumin versus hydroxyethyl starch in cardiopulmonary bypass surgery: a meta-analysis of postoperative bleeding. Ann Thorac Surg 2001; 72(2): 527-33; discussion 534.

30a. Cochrane Injuries Group Albumin Reviewers. Human albumin administration in critically ill patients: systematic review of randomised controlled trials. Bmj 1998; 317 (7153): 235-40.

31a. Finfer S, Bellomo R, Boyce N, French J, Myburgh J, Norton R. A comparison of albumin and saline for fluid resuscitation in the intensive care unit. N Engl J Med 2004; 350(22): 2247-56.

32a. Huxley V H, Curry F E. Albumin modulation of capillary permeability: test of an adsorption mechanism. Am J Physiol 1985; 248(2 Pt 2): H264-73.

33a. Michel C C, Phillips M E, Turner M R. The effects of native and modified bovine serum albumin on the permeability of frog mesenteric capillaries. J Physiol 1985; 360: 333-46.

34a. Michel C C. The Malpighi lecture. Vascular permeability—the consequence of Malpighi's hypothesis. Int J Microcirc Clin Exp 1985; 4(3): 265-84.

35a. Pries A R, Secomb T W, Jacobs H, Sperandio M, Osterloh K, Gaehtgens P. Microvascular blood flow resistance: role of endothelial surface layer. Am J Physiol 1997; 273(5 Pt 2): H2272-9.

36a. Zoellner H, Hou J Y, Lovery M, Kingham J, Srivastava M, Bielek E, et al. Inhibition of microvascular endothelial apoptosis in tissue explants by serum albumin. Microvasc Res 1999; 57(2): 162-73.

37a. Meeson A, Palmer M, Calfon M, Lang R. A relationship between apoptosis and flow during programmed capillary regression is revealed by vital analysis. Development 1996; 122(12): 3929-38.

38a. Quinlan G J, Margarson M P, Mumby S, Evans T W, Gutteridge J M. Administration of albumin to patients with sepsis syndrome: a possible beneficial role in plasma thiol repletion. Clin Sci (Lond) 1998; 95(4): 459-65.

39a. Zhang W J, Frei B. Albumin selectively inhibits TNF alpha-induced expression of vascular cell adhesion molecule-1 in human aortic endothelial cells. Cardiovasc Res 2002; 55(4): 820-9.

40a. Powers K A, Kapus A, Khadaroo R G, He R, Marshall J C, Lindsay T F, et al. Twenty-five percent albumin prevents lung injury following shock/resuscitation. Crit Care Med 2003; 31(9): 2355-63.

41a. Doweiko J P, Nompleggi D J. Role of albumin in human physiology and pathophysiology. JPEN J Parenter Enteral Nutr 1991; 15(2): 207-11.

42a. Assaly R A, Azizi M, Kennedy D J, Amauro C, Zaher A, Houts F W, et al. Plasma expansion by polyethylene glycol modified albumin. Clin Sci (Lond) 2004.

43a. Zeuzem S. Hepatitis C virus: kinetics and quasispecies evolution during anti-viral therapy. Forum (Genova) 2000; 10(1): 32-42.

44a. Chang T M, Lister C, Nishiya, Varma R. Immunological effects of hemoglobin, encapsulated hemoglobin, polyhemoglobin and conjugated hemoglobin using different immunization schedules. Biomater Artif Cells Immobilization Biotechnol 1992; 20(2-4): 611-8.

45a. Abuchowski A, van Es T, Palczuk N C, Davis F F. Alteration of immunological properties of bovine serum albumin by covalent attachment of polyethylene glycol. J Biol Chem 1977; 252(11): 3578-81.

46a. Harris J M, Martin N E, Modi M. Pegylation: a novel process for modifying pharmacokinetics. Clin Pharmacokinet 2001; 40(7): 539-51.

47a. Vert M, Domurado D. Poly(ethylene glycol): protein-repulsive or albumin-compatible? J Biomater Sci Polym Ed 2000; 11 (12): 1307-17.

48a. Shum K L, Leon A, Viau A T, Pilon D, Nucci M, Shorr R G. The physiological and histopathological response of dogs to exchange transfusion with polyethylene glycol-modified bovine hemoglobin (PEG-Hb). Artif Cells Blood Substit Immobil Biotechnol 1996; 24(6): 655-83.

49a. Tsai A G, Intaglietta M. High viscosity plasma expanders: Volume restitution fluids for lowering the transfusion trigger. Biorheology 2001; 38(2-3): 229-37.

50a. Ameno H, Tani T, Hanasawa K, Kodama M. New method for the detection of bacterial translocation using intestinal permeability with polyethylene glycol 4000. Eur Surg Res 2000; 32(1): 23-9.

51a. Capone A, Safar P, Stezoski S W, Peitzman A, Tisherman S. Uncontrolled hemorrhagic shock outcome model in rats. Resuscitation 1995; 29(2): 143-52.

52a. Capone A C, Safar P, Stenos W, Tisherman S, Peitzman A B. Improved outcome with fluid restriction in treatment of uncontrolled hemorrhagic shock. J Am Coll Surg 1995; 180(1): 49-56.

53a. Kentner R, Safar P, Behringer W, Wu X, Kagan V E, Tyurina Y Y et al. Early antioxidant therapy with Tempol during hemorrhagic shock increases survival in rats. J Trauma 2002; 53(5): 968-77.

54a. Katz N M, Hannan R L, Hopkins R A, Wallace R B. Cardiac operations in patients aged 70 years and over: mortality, length of stay, and hospital charge. Ann Thorac Surg 1995; 60(1): 96-100; discussion 100-1.

55a. Katz L, Ebmeyer U, Safar P, Radovsky A, Neumar R. Outcome model of asphyxial cardiac arrest in rats. J Cereb Blood Flow Metab 1995; 15(6): 1032-9.

56a. Powers K A, Kapus A, Khadaroo R G, Papia G, Rotstein O D. 25% Albumin modulates adhesive interactions between neutrophils and the endothelium following shock/resuscitation. Surgery 2002; 132(2): 391-8.

57a. Choi W I, Quinn D A, Park K M, Moufarrej R K, Jafari B, Syrkina O. et al. Systemic microvascular leak in an in vivo rat model of ventilator-induced lung injury. Am J Respir Crit Care Med 2003; 167(12): 1627-32.

58a. Schumacher J, Binkowski K, Dendorfer A, Klotz K F. Organ-specific extravasation of albumin-bound evans blue during nonresuscitated hemorrhagic shock in rats. Shock 2003; 20(6): 565-8.

59a. Bakker J, Gris P, Coffernils M, Kahn R J, Vincent J L. Serial blood lactate levels can predict the development of multiple organ failure following septic shock. Am J Surg 1996; 171(2): 221-6?

60a. McCarter F D, James J H, Luchette F A, Wang L, Friend L A, King J K, et al. Adrenergic blockade reduces skeletal muscle glycolysis and Na(+), K(+)-ATPase activity during hemorrhage. J Surg Res 2001; 99(2): 235-44.

61a. Story D A, Morimatsu H, Bellomo R. Strong ions, weak acids and base excess: a simplified Fencl-Stewart approach to clinical acid-base disorders. Br J Anaesth 2004; 92(1): 54-60.

62a. Balasubramanyan N, Havens P L, Hoffman G M. Unmeasured anions identified by the Fencl-Stewart method predict mortality better than base excess, anion gap, and lactate in patients in the pediatric intensive care unit. Crit Care Med 1999; 27(8): 1577-81.

63a. Astrup P, Jorgensen K, Andersen O S, Engel K. The acid-base metabolism. A new approach. Lancet 1960; 1:1035-9.

64a. Siggaard-Andersen O. The acid-base status of the blood. Scand J Clin Lab Invest 1963; 15(Suppl 70): 1-134.

65a. Mazzoni M C, Tsai A G, Intaglietta M. Blood and plasma viscosity and microvascular function in hemodilution. A perspective from La Jolla, Calif. Eur Surg Res 2002; 34(1-2): 101-5.

66a. Chen R Y, Carlin R D, Simchon S, Jan K M, Chien S. Effects of dextran-induced hyperviscosity on regional blood flow and hemodynamics in dogs. Am J Physiol 1989; 256(3 Pt 2): H898-905.

67a. Jiang W H, Han S J. Viscosity of Nonionic Polymer/Anionic Surfactant Complexes in Water. J Colloid Interface Sci 2000; 229(1): 1-5.

68a. Molina P E. Noradrenergic inhibition of TNF upregulation in hemorrhagic shock. Neuroimmunomodulation 2001; 9(3): 125-33.

69a. Guarini S, Altavilla D, Cainazzo MM, Giuliani D, Bigiani A, Marini H, et al. Efferent vagal fibre stimulation blunts nuclear factor-kappaB activation and protects against hypovolemic hemorrhagic shock. Circulation 2003; 107(8): 1189-94.

70a. Hierholzer C, Billiar T R, Tweardy D J. Requirements for NF-kappaB activation in hemorrhagic shock. Arch Orthop Trauma Surg 2002; 122(1): 44-7.

71a. Repine J E. Scientific perspectives on adult respiratory distress syndrome. Lancet 1992; 339(8791): 466-9.

72a. Gaines G C, Welborn M B, 3rd, Moldawer L L, Huber T S, Harward T R, Seeger J M. Attenuation of skeletal muscle ischemia/reperfusion injury by inhibition of tumor necrosis factor. J Vasc Surg 1999; 29(2): 370-6.

73a. Ayala A, Wang P, Bad Z F, Perrin M M, Retell W, Chaudry I H. Differential alterations in plasma IL-6 and TNF levels after trauma and hemorrhage. Am J Physiol 1991; 260(1 Pt 2): R167-71.

74a. Song Y, Ao L, Raeburn C D, Calkins C M, Abraham E, Harken A H, et al. A low level of TNF-alpha mediates hemorrhage-induced acute lung injury via p55 TNF receptor. Am J Physiol Lung Cell Mol Physiol 2001; 281(3): L677-84.

75a. Zhang H, Voglis S, Kim C H, Slutsky A S. Effects of albumin and Ringer's lactate on production of lung cytokines and hydrogen peroxide after resuscitated hemorrhage and endotoxemia in rats. Crit Care Med 2003; 31(5): 1515-22.

76a. Matsui H, Ihara Y, Fujio Y, Kunisada K, Akira S, Kishimoto T, et al. Induction of interleukin (IL)-6 by hypoxia is mediated by nuclear factor (NF)-kappa B and NF-IL6 in cardiac myocytes. Cardiovasc Res 1999; 42(1): 104-12.

77a. Cantin A M, Paquette B, Richter M, Larivee P. Albumin-mediated regulation of cellular glutathione and nuclear factor kappa B activation. Am J Respir Crit Care Med 2000; 162(4 Pt 1): 1539-46.

78a. Holman R G, Maier R V. Oxidant-induced endothelial leak correlates with decreased cellular energy levels. Am Rev Respir Dis 1990; 141(1): 134-40.

79a. Holman R G, Maier R V. Superoxide production by neutrophils in a model of adult respiratory distress syndrome. Arch Surg 1988; 123(12): 1491-5.

80a. Gilmont R R, Dardano A, Young M, Engle J S, Adamson B S, Smith D J, Jr., et al. Effects of glutathione depletion on oxidant-induced endothelial cell injury. J Surg Res 1998; 80(1): 62-8.

81a. Gilmont R R, Dardano A, Engle J S, Adamson B S, Welsh M J, Li T, et al. TNF-alpha potentiates oxidant and reperfusion-induced endothelial cell injury. J Surg Res 1996; 61(1): 175-82.

82a. Xu Y X, Wichmann M W, Ayala A, Cioffi W G, Chaudry I H. Trauma-hemorrhage induces increased thymic apoptosis while decreasing IL-3 release and increasing GM-CSF. J Surg Res 1997; 68(1): 24-30.

83a. Daemen M A, van't Veer C, Denecker G, Heemskerk V H, Wolfs T G, Clauss M, et al. Inhibition of apoptosis induced by ischemia-reperfusion prevents inflammation. J Clin Invest 1999; 104(5): 541-9.

84a. Zoellner H, Hofler M, Beckmann R, Hufnagl P, Vanyek E, Bielek E, et al. Serum albumin is a specific inhibitor of apoptosis in human endothelial cells. J Cell Sci 1996; 109 (Pt 10): 2571-80.

85a. Meister A, Anderson M E. Glutathione. Annul Rev Biochem 1983; 52:711-60.

86a Higuchi Y, Matsukawa S. Glutathione depletion induces giant DNA and high-molecular-weight DNA fragmentation associated with apoptosis through lipid peroxidation and protein kinase C activation in C6 glioma cells. Arch Biochem Biophys 1999; 363(1): 33-42.

87a Aoshiba K, Yasui S, Nishimura K, Nagai A. Thiol depletion induces apoptosis in cultured lung fibroblasts. Am J Respir Cell Mol Biol 1999; 21 (1): 54-64.

88a. Bourdon E, Bache D. The importance of proteins in defense against oxidation. Antioxid Redox Signal 2001; 3(2): 293-311.

89. Wang T G, Gotoh Y, Jennings M H, Rhoads C A, Aw T Y. Lipid hydroperoxide-induced apoptosis in human colonic CaCo-2 cells is associated with an early loss of cellular redox balance. Faseb J 2000; 14(11): 1567-76.

90a. Motyl T, Grzelkowska K, Zimowska W, Skierski J, Wareski P, Ploszaj T, et al. Expression of bcl-2 and bax in 90a. TGF-beta 1-induced apoptosis of L1210 leukemic cells. Eur J Cell Biol 1998; 75(4): 367-74.
91a. Kang C D, Jang J H, Kim K W, Lee H J, Jeong C S, Kim C M, et al. Activation of c-jun N-terminal kinase/stress-activated protein kinase and the decreased ratio of Bcl-2 to Bax are associated with the auto-oxidized dopamine-induced apoptosis in PC12 cells. Neurosci Lett 1998; 256(1): 37-40.
92a. Margarson M P, Soni N C. Effects of albumin supplementation on microvascular permeability in septic patients. J Appl Physiol 2002; 92(5): 2139-45.
93a. Osterloh K, Ewert U, Pries A R. Interaction of albumin with the endothelial cell surface. Am J Physiol Heart Circ Physiol 2002; 283(1): H398-405.
94a. Gavrieli Y, Sherman Y, Ben-Sasson S A. Identification of programmed cell death in situ via specific labeling of nuclear DNA fragmentation. J Cell Biol 1992; 119(3): 493-501.
95a. Thornberry N A. Caspases: key mediators of apoptosis. Chem Biol 1998; 5(5): R97-103.
96a. Hissin P J, Hilf R. A fluorometric method for determination of oxidized and reduced glutathione in tissues. Anal Biochem 1976; 74(1): 214-26.
97a. Young I S, Trimble E R. Measurement of malondialdehyde in plasma by high performance liquid chromatography with fluorimetric detection. Ann Clin Biochem 1991; 28 (Pt 5): 504-8.
98a. Rice-Evans C, Miller N J. Total antioxidant status in plasma and body fluids. Methods Enzyme 1994; 234:279-93.
99a. Miller N J, Rice-Evans C, Davies M J, Gopinathan V, Milner A. A novel method for measuring antioxidant capacity and its application to monitoring the antioxidant status in premature neonates. Clin Sci (Lond) 1993; 84(4): 407-12.
100a. Carter D C, He X M, Munson S H, Twigg P D, Gernert K M, Broom M B, et al. Three-dimensional structure of human serum albumin. Science 1989; 244(4909): 1195-8.
101a. Carter J M, Vanalbert S, Lee J, Lyon J, Deal C. Shedding light on peptide synthesis. Biotechnology (NY) 1992; 10(5): 509-13.
102a. Peters T. All about Albumin: Academic Press, Orlando Fla.; 1996.
103a. Eftink M R, Shastry M C. Fluorescence methods for studying kinetics of protein-folding reactions. Methods Enzymol 1997; 278:258-86.
104a. Muzammil S, Kumar Y, Tayyab S. Anion-induced stabilization of human serum albumin prevents the formation of intermediate during urea denaturation. Proteins 2000; 40(1): 29-38.
105a. Pace C N. Determination and analysis of urea and guanidine hydrochloride denaturation curves. Methods Enzymol 1986; 131:266-80.
106a. Krishnakumar S S, Panda D. Spatial relationship between the prodan site, Trp-214, and Cys-34 residues in human serum albumin and loss of structure through incremental unfolding. Biochemistry 2002; 41 (23): 7443-52.
107a. Flora K, Brennan J D, Baker G A, Doody M A, Bright F V. Unfolding of acrylodan-labeled human serum albumin probed by steady-state and time-resolved fluorescence methods. Biophys J 1998; 75(2): 1084-96.
108a. Chen R F. Removal of fatty acids from albumin by charcoal treatment. J. Biol. Chem (1967); 242:173-181.
109a. Shrake AaSR. Biphasic denaturation of human albumin due to ligand redistribution during unfolding. J. Biol. Chem (1988); 263:15392-15299.
110a. Schrake A, J. S. Finalayson, P. D. Ross Thermal stability of Human albumin measured by differential scanning calorimetry: I. Effects of capyrlate and N-acetyltryptophan. Thermal stability of Human albumin measured by differential scanning calorimetry: I. Effects of capyrlate and N-acetyltryptophan. Vox. Sang 1984; 47:7-18.
111 a. Schrake A, J. S. Finalayson, P. D. Ross. Thermal stability of Human albumin measured by differential scanning calorimetry: I. Effects of isomers of N-acetyltryptophanate and tryptophanate, pH, reheating and dimerization. Vox. Sang. 1984; 47:19-27.
112a. Eftink M R, Ghiron C A. Fluorescence quenching studies with proteins. Anal Biochem 1981; 114(2): 199-227.
113a. Lakowicz J R. Principles of frequency-domain fluorescence spectroscopy and applications to cell membranes. Subcell Biochem 1988; 13:89-126.
114a. K. E. van Holde W C JaPSH. Physical biochemistry. Prentice Hall, N.J.; 1998.
115a. Castellino F J, Barker R. The denaturing effectiveness of guanidinium, carbamoylguanidinium, and guanylguanidinium salts. Biochemistry 1968; 7(11): 4135-8.
116a. Delgado C, Francis G E, Fisher D. The uses and properties of PEG-linked proteins. Crit Rev Ther Drug Carrier Syst 1992; 9(3-4): 249-304.
117a. Monfardini C, Schiavon O, Caliceti P, Morpurgo M, Harris J M, Veronese F M. A branched monomethoxypoly (ethylene glycol) for protein modification. Bioconjug Chem 1995; 6(1): 62-9.
118a. Karr L J, Donnelly D L, Kozlowski A, Harris J M. Use of poly (ethylene glycol)-modified antibody in cell extraction. Methods Enzymol 1994; 228:377-90.
119a. Francis G E, Fisher D, Delgado C, Malik F, Gardiner A, Neale D. PEGylation of cytokines and other therapeutic proteins and peptides: the importance of biological optimisation of coupling techniques. Int J Hematol 1998; 68(1): 1-18.
120a. M. L. Nucci R S, and Abuchowski A, The therapeutic value of poly(ethyleneglycol)-modified proteins. Adv. Drug Del. Rev 1991:133-.
121a. Nilsson K, Mosbach K. Immobilization of enzymes and affinity ligands to various hydroxyl group carrying supports using highly reactive sulfonyl chlorides. Biochem Biophys Res Commun 1981; 102(1): 449-57.
122a. Delgado C, Patel J N, Francis G E, Fisher D. Coupling of poly(ethylene glycol) to albumin under very mild conditions by activation with tresyl chloride: characterization of the conjugate by partitioning in aqueous two-phase systems. Biotechnol Appl Biochem 1990; 12(2): 119-28.
123a. Richter A W, Akerblom E. Antibodies against polyethylene glycol produced in animals by immunization with monomethoxy polyethylene glycol modified proteins. Int Arch Allergy Appl Immunol 1983; 70(2): 124-31.
124a. Nag A, Mitra G, Ghosh P C. A colorimetric assay for estimation of polyethylene glycol and polyethylene glycolated protein using ammonium ferrothiocyanate. Anal Biochem 1996; 237(2): 224-31.
125a. Peters T. All about Albumin; 1996.
126a. Saifer M G, Somack R, Williams L D. Plasma clearance and immunologic properties of long-acting superoxide dismutase prepared using 35,000 to 120,000 dalton polyethylene glycol. Adv Exp Med Biol 1994; 366:377-87.
127a. Snider J, Neville C, Yuan L C, Bullock J. Characterization of the heterogeneity of polyethylene glycol-modified superoxide dismutase by chromatographic and electrophoretic techniques. J Chromatogr 1992; 599(1-2): 141-55.

128a. McGoff P, Baziotis A C, Maskiewicz R. Analysis of polyethylene glycol modified superoxide dismutase by chromatographic, electrophoretic, light scattering, chemical and enzymatic methods. Chem Pharm Bull (Tokyo) 1988; 36(8): 3079-91.

129a. Greenfield N J. Methods to estimate the conformation of proteins and polypeptides from circular dichroism data. Anal Brioche 1996; 235(1): 1-10.

130a. Johnson W C, Jr. Protein secondary structure and circular dichroism: a practical guide. Proteins 1990; 7(3): 205-14.

131a. Dockal M, Carter D C, Ruker F. The three recombinant domains of human serum albumin. Structural characterization and ligand binding properties. J Biol Chem 1999; 274(41): 29303-10.

132a. Curry S, Mandelkow H, Brick P, Franks N. Crystal structure of human serum albumin complexed with fatty acid reveals an asymmetric distribution of binding sites. Nat Struct Biol 1998; 5(9): 827-35.

133a. Dignam J D, Nada, S., and Chaires, J. B. T., hermodynamic Characterization of the Binding of Nucleotides to Glycyl-tRNA Synthetase. Biochem Biophys Res Commun 2003; 42:5333-5340.

134a. Freire E, Mayorga, O. L., and Straume, MIsothermal titration calorimetry. Anal. Chem 1990; 62:950A-959A.

135a. Peirce MMRCSaBTN. Isothermal Titration calorimetry of protein-protein interactions. Methods Enzymol 1999; 19:213-221.

136a. Dina J D N, S., and Chaires, J. B. T. hermodynamic Characterization of the Binding of Nucleotides to Glycyl-tRNA Synthetase. Biochem Biophys Res Commun 2003; 42:5333-5340.

137a. Jacobsen J. Studies of the affinity of human serum albumin for binding of bilirubin at different temperatures and ionic strength. Int J Pept Protein Res 1977; 9(3): 235-9.

138a. A. A. Specter and J. E. Fletcher in (J. M. Dietschy A M G, Jr., and J. A. Ontko, eds), Disturbances in lipid and lipoprotein metabolism, Rockville, Md.; 1978.

139a. Adams P A, Berman M C. Kinetics and mechanism of the interaction between human serum albumin and monomeric haemin. Biochem J 1980; 191(1): 95-102.

140a. 39. Freire E. Differential scanning calorimetry Meth. Mol. Biol. 1995; 40:191-218.

141a. Jelesarov I, and Bosshard, H. R. Isothermal titration calorimetry and differential scanning calorimetry as complementary tools to investigate the energetics of biomolecular recognition. J. Mol. Recog 1999; 12:3-18.

142a. P. C. Weber and F. R. Salemme. Applications of clorimetric methods to drug discovery and the study of protein interactions. Curr. Opin Struct. Boil (2003); 13:115-121.

143a. Pockros P J, M. Shiffman, G. Everson, R. Reindollar, M. W. Fried, P. P. Purdum, D. Jensen, C. Smith, W. M. Lee, T. D. Boyer, A. Lin, S. Pedder, T. L. DePamphilis. K. R. Reddy and J. Wright. Efficacy and safety of pegylated (40-kd) interferon alpha-2a compared with interferon alpha-2a in noncirrhotic patients with chronic hepatitis. Hepatology (2001); 33: 433-8.

144a. Algranati N E, S. Sy, M. Modi. Hepatology. In; 1999. p. 190A.

145a. V. K. Rowe M A W. "Glycols". N.Y: G. D. Clayton and F. E Clayton, Eds, John Willey and Sons; 1982.

146a. Carpenter C P, Woodside M D, Kinkead E R, King J M, Sullivan L J. Response of dogs to repeated intravenous injection of polyethylene glycol 4000 with notes on excretion and sensitization. Toxicol Appl Pharmacol 1971; 18(1): 3540.

147a. Shaffer CBaFHC, The absorption and excretion of the solid polyethylene glycols ("carbowax" compounds). In: J. Am. Pham. Ass. 1947. P. 36,152-157.

148a. Smyth H F, Jr., Carpenter C P, Weil C S. Range-finding toxicity data: List IV. An M A Arch Ind Hyg Occup Med 1951; 4(2): 119-22.

149a. Smyth J, H. f., C. P. Carpenter and C. S. Weil, The Toxicology of the polyethylene glycols. J. Am. Pharm. Ass. 1950; 39,349-354.

150a. Rowe V K, M. A. Wolf, G. D. Clayton and F. E. Clayton, Eds, "Glycols". N.Y: John Willey and Sons; 1982.

We claim:

1. A method for augmenting hydrophilic properties and increasing half-life of at least one albumin protein of interest in serum and decreasing the immunogenicity of at least one albumin protein comprising administering to a patient in need thereof, a composition comprising a polyethylene glycol-albumin-based colloid composition having at least one protected thiol region wherein the composition comprises PEG-$Alb_{Cys-34}$ having a large hydrodynamic radius with Cys-34 preserved as a thiol, wherein the polyethylene glycol-albumin based colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons.

2. A method for maintaining vascular volume in a patient in need thereof, comprising administering a composition comprising a polyethylene glycol-albumin based colloid composition having at least one protected thiol region wherein the composition comprises PEG-$Alb_{Cys-34}$ having a large hydrodynamic radius with Cys-34 preserved as a thiol, wherein the polyethylene glycol-albumin base colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons.

3. A method for treating hemorrhagic shock in a patient in need thereof, comprising administering a composition comprising a polyethylene glycol-albumin based colloid composition having at least one protected thiol region wherein the composition comprises PEG-$Alb_{Cys-34}$ having a large hydrodynamic radius with Cys-34 preserved as a thiol, wherein the polyethylene glycol-albumin base colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons.

4. A method for lowering a transfusion trigger to levels below 7 g/dl whereby oxygen delivery to peripheral tissues is maintained at lower hemoglobin level for a longer time prior to blood transfusion in a patient in need thereof, comprising administering a composition comprising a polyethylene glycol-albumin based colloid composition having at least one protected thiol region wherein the composition comprises PEG-$Alb_{Cys-34}$ having a large hydrodynamic radius with Cys-34 preserved as a thiol, wherein the polyethylene glycol-albumin base colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons.

5. A method for maintaining an oncotic gradient that reduces extravasation of fluid into the tissue interstitial space in a patient in need thereof, comprising administering a composition comprising a polyethylene glycol-albumin based colloid composition having at least one protected thiol region wherein the composition comprises PEG-Alb$_{Cys-34}$ having a large hydrodynamic radius with Cys-34 preserved as a thiol, wherein the polyethylene glycol-albumin base colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons.

6. A method for increasing glutathione and increasing GSH/GSSG in a patient in need thereof, comprising administering a composition comprising a polyethylene glycol-albumin based colloid composition having at least one protected thiol region wherein the composition comprises PEG-Alb$_{Cys-34}$ having a large hydrodynamic radius with Cys-34 preserved as a thiol, wherein the polyethylene glycol-albumin base colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons.

7. The method of claim 1 wherein the composition is capable of being lyophilized, rehydrated, restored and reconstituted due to sepsis, shock, burn, trauma, surgery, predisposition to capillary leak, hyperviscosity states, hypoalbuminemia, leukopheresis, nutritional albumin deficiency, nephrotic syndrome, liver failure or anoxia.

8. The method of claim 1, wherein the PEG-Alb$_{Cys-34}$ has an ability to bind ligands.

9. The method of claim 8, wherein the ligands comprise sodium ions, fatty acids, bilirubin and therapeutic drugs.

10. An in vivo method of treating hypovolemic conditions in a patient in danger of developing the hypovolemic conditions and/or multiorgan dysfunction comprising administering a therapeutic amount of a composition comprising a polyethylene glycol-albumin based colloid composition having at least one protected thiol region wherein the composition comprises PEG-Alb$_{Cys-34}$ having a large hydrodynamic radius with Cys-34 preserved as a thiol, wherein the polyethylene glycol-albumin base colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons.

11. A method for the pretreatment of mammalian tissue injury from at least one hypovolemic condition comprising the administration of a therapeutic amount to a mammal of a composition comprising a polyethylene glycol-albumin based colloid composition having at least one protected thiol region wherein the composition comprises PEG-Alb$_{Cys-34}$ having a large hydrodynamic radius with Cys-34 preserved as a thiol, wherein the polyethylene glycol-albumin base colloid composition, has a molecular excluded volume and a hydrodynamic radius sufficiently large to preclude the composition from leaking through a patient's capillaries and wherein the albumin is human albumin or bovine serum albumin; and wherein the polyethylene glycol-albumin based colloid composition has an average molecular weight of at least 128,000 daltons, the composition being incapable of leaking through the mammal's capillaries and being present in an amount sufficient to protect said tissue from injury.

12. The method of claim 11, where the injury is due to sepsis, shock, burn, trauma, surgery, predisposition to capillary leak, hyperviscosity states, hypoalbuminemia, leukopheresis, nutritional albumin deficiency, nephritic syndrome, liver failure, and/or anoxia.

* * * * *